US006492378B1

(12) United States Patent
Harling et al.

(10) Patent No.: US 6,492,378 B1
(45) Date of Patent: Dec. 10, 2002

(54) SUBSTITUTED ISOQUINOLINE DERIVATIVES AND THEIR USE AS ANTICONVULSIVANTS

(75) Inventors: John David Harling, Sawbridgeworth; Jag Paul Heer; Mervyn Thompson, both of Harlow, all of (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/762,613

(22) PCT Filed: Aug. 6, 1999

(86) PCT No.: PCT/EP99/05762

§ 371 (c)(1),
(2), (4) Date: Feb. 9, 2001

(87) PCT Pub. No.: WO00/09486

PCT Pub. Date: Feb. 24, 2000

(30) Foreign Application Priority Data

Aug. 11, 1998 (GB) ............................................. 9817424

(51) Int. Cl.$^7$ ..................... A61K 31/438; A61K 31/472; A61K 31/473; C07D 215/04; C07D 215/12
(52) U.S. Cl. ....................... 514/278; 514/307; 514/311; 546/18; 546/112; 546/159
(58) Field of Search ........................... 546/18, 112, 134, 546/139, 152, 159; 514/278, 307, 311

(56) References Cited

U.S. PATENT DOCUMENTS 3,674,791 A * 7/1972 William ........................ 546/143
4,022,900 A 5/1977 Mathison ...................... 424/258

FOREIGN PATENT DOCUMENTS

| DE | 19 00 948 A | 5/1977 |
| GB | 1 164 192 A | 9/1969 |
| WO | WO 97/48683 | 12/1997 |
| WO | WO 98/41507 | 9/1998 |
| WO | WO 98/41508 | 9/1998 |

OTHER PUBLICATIONS

Mathison, et al., "Synthesis and Hypotensive Properties of Tetrahydroisoquinolines", (1973), Journal of Medicinal Chemistry, vol. 16, No. 4, XP002040786, pp. 332–336.

* cited by examiner

Primary Examiner—Alan L. Rotman
Assistant Examiner—Rita Desai
(74) Attorney, Agent, or Firm—Linda E. Hall; Stephen A. Venetianer; Charles M. Kinzig

(57) ABSTRACT

This invention relates to novel substituted isoquinoline derivatives and their use as anticonvulsants.

8 Claims, No Drawings

SUBSTITUTED ISOQUINOLINE DERIVATIVES AND THEIR USE AS ANTICONVULSIVANTS

This invention relates to novel compounds, to processes for preparing them, and to their use as therapeutic agents.

U.S. Pat. No. 4,022,900 (Marion) discloses benzamido-tetrahydroisoquinolines having anti-hypertensive and vasodilator properties.

PCT/GB98/00781 (SmithKline Beecham), unpublished at the filing date of this application, discloses that benzamide compounds of formula (A) below possess anti-convulsant activity and are therefore believed to be useful in the treatment and/or prevention of anxiety, mania, and related depression disorders.

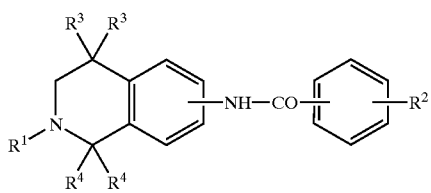

(A)

where;

R$^1$ is hydrogen, C$_{1-6}$ alkyl (optionally substituted by hydroxy or C$_{1-4}$alkoxy), C$_{1-6}$alkenyl, C$_{1-6}$alkynyl, C$_{1-6}$alkylCO—, formyl, CF$_3$CO— or C$_{1-6}$alkylSO$_2$—, R$^2$ is hydrogen or up to three substituents selected from halogen, NO$_2$, CN, N$_3$, CF$_3$O—, CF$_3$S—, CF$_3$CO—, trifluoromethyldiazirinyl, C$_{1-6}$alkyl, C$_{1-6}$alkenyl, C$_{1-6}$alkynyl, C$_{1-6}$perfluoroalkyl, C$_{3-6}$cycloalkyl, C$_{3-6}$cycloalkyl-C$_{1-4}$alkyl-, C$_{1-6}$alkylO—, C$_{1-6}$alkylCO—, C$_{3-6}$cycloalkylO—, C$_{3-6}$cycloalkylCO—, C$_{3-6}$cycloalkyl-C$_{1-4}$alkylO—, C$_{3-6}$cycloalkyl-C$_{1-4}$alkylCO—, phenyl, phenoxy, benzyloxy, benzoyl, phenyl-C$_{1-4}$alkyl-, C$_{1-6}$alkylS—, C$_{1-6}$alkylSO$_2$—, (C$_{1-4}$alkyl)$_2$NSO$_2$—, (C$_{1-4}$alkyl)NHSO$_2$—, (C$_{1-4}$alkyl)$_2$NCO—, (C$_{1-4}$alkyl)NHCO— or CONH$_2$;

or —NR$^5$R$^6$ where R$^5$ is hydrogen or C$_{1-4}$ alkyl, and R$^6$ is hydrogen, C$_{1-4}$alkyl, formyl, —CO$_2$C$_{1-4}$alkyl or —COC$_{1-4}$alkyl;

or two R$^2$ groups together form a carbocyclic ring that is saturated or unsaturated and unsubstituted or substituted by —OH or =O; and the two R$^3$ groups and the two R$^4$ groups are each independently hydrogen or C$_{1-6}$ alkyl or the two R$^3$ groups and/or the two R$^4$ groups together form a C$_{3-6}$ spiroalkyl group provided that at least one R$^3$ and R$^4$ group is not hydrogen.

It has now been surprisingly found that carboxamide compounds of formula (I) below possess anti-convulsant activity and are therefore believed to be useful in the treatment and/or prevention of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, and amyotrophic lateral sclerosis (ALS).

Accordingly, the present invention provides a compound of formula (I) or salts thereof or solvates thereof:

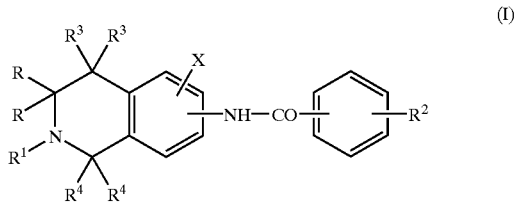

(I)

wherein:

R$^1$ is hydrogen, C$_{1-6}$ alkyl (optionally substituted by hydroxy or C$_{1-4}$alkoxy), C$_{1-6}$alkenyl, C$_{1-6}$alkynyl, C$_{1-6}$alkylCO—, formyl, CF$_3$CO— or C$_{1-6}$alkylSO$_2$—;

R$^2$ is hydrogen or up to three substituents selected from halogen, NO$_2$, CN, N$_3$, CF$_3$O—, CF$_3$S—, CF$_3$CO—, CF$_3$SO$_2$, trifluoromethyldiazirinyl, C$_{1-6}$alkyl, C$_{1-6}$alkenyl, C$_{1-6}$alkynyl, C$_{1-6}$perfluoroalkyl, C$_{3-6}$cycloalkyl, C$_{3-6}$cycloalkyl-C$_{1-4}$alkyl-, C$_{1-6}$alkylO—, C$_{1-6}$alkylCO—, C$_{3-6}$cycloalkylO—, C$_{3-6}$cycloalkylCO—, C$_{3-6}$cycloalkyl-C$_{1-4}$alkylO—, C$_{3-6}$cycloalkyl-C$_{1-4}$alkylCO—, phenyl, phenoxy, benzyloxy, benzoyl, phenyl-C$_{1-4}$alkyl-, C$_{1-6}$alkylS—, C$_{1-6}$alkylSO$_2$—, (C$_{1-4}$alkyl)$_2$NSO$_2$—,(C$_{1-4}$alkyl) NHSO$_2$—, (C$_{1-4}$alkyl)$_2$NCO—, (C$_{1-4}$alkyl)NHCO— and CONH$_2$; or —NR$^5$R$^6$ where R$^5$ is hydrogen or C$_{1-4}$ alkyl, and R$^6$ is hydrogen, C$_{1-4}$alkyl, formyl, —CO$_2$C$_{1-4}$alkyl or —COC$_{1-4}$alkyl; or two R$^2$ groups together form a carbocyclic ring that is saturated or unsaturated and unsubstituted or substituted by —OH or =O;

the two R groups, the two R$^3$ groups and the two R$^4$ groups are each independently hydrogen, C$_{1-6}$ alkyl, C$_{1-6}$ alkenyl, benzyl, or phenyl, or the two R groups and/or the two R$^3$ groups and/or the two R$^4$ groups together form a C$_{3-6}$ spiroalkyl group, provided that at least one R, R$^3$ or R$^4$ group is other than hydrogen; and X is selected from the group consisting of hydrogen, halogen, cyano, CF$_3$, alkyl and alkoxy;

provided that when X is hydrogen, the two R groups are not both hydrogen.

The compounds of this invention are typically isoquinolinyl-carboxamides, especially (tetrahydroisoquinolin-5-yl) and (tetrahydroisoquinolin-7-yl)carboxamides. The carboxamide moiety may be a benzamide. When two R$^2$ groups form a carbocyclic ring, this is typically a 5–7 membered ring, and the carboxamide moiety may be a naphthalene carboxamide or an indane or indanone carboxamide.

In the formula (I), alkyl groups, including alkyl groups that are part of other moieties, such as alkoxy or acyl, may be straight chain or branched. Phenyl groups, including phenyl groups that are part of other moieties, in R$^2$ may optionally be substituted with one or more independently selected halogen or C$_{1-6}$ alkyl, C$_{1-6}$ alkoxy or C$_{1-6}$ alkyl-carbonyl.

Suitable $C_{3-6}$ cycloalkyl groups include cyclopropyl, cyclobutyl, cyclopentyl, and cyclohexyl. Suitable halo substituents include fluoro, chloro, iodo and bromo.

It should be appreciated that compounds of the present invention possess chiral centres and as such may exist in different enantiomeric forms, the present invention extends to each enantiomeric form and mixtures thereof including diastereoisomers and racemates.

A preferred group of compounds of formula (I) have;

R as methyl or hydrogen; and/or $R^1$ as hydrogen or methyl; and/or $R^2$ as methyl, ethyl, iso-propyl, methoxy, ethoxy, iso-propoxy, bromo, chloro, fluoro, iodo, cyano, acetyl, $CF_3$, or $C_2F_5$; and/or $R^3$ as hydrogen, methyl, or spirocyclobutyl; and/or $R^4$ as hydrogen, methyl, benzyl, allyl, phenyl, iso-butyl, or iso-propyl; and/or X as hydrogen, chloro, bromo, methyl, or ethyl.

A further aspect of the invention provides a compound selected from the group consisting of;

N-(3,3-Dimethyl-1,2,3,4-tetrahydro-2-trifluoroacetyl-isoquinolin-7-yl)-4-methoxy-3-trifluoromethylbenzamide;

N-(3,3-Dimethyl-1,2,3,4-tetrahydro-2-trifluoroacetyl-isoquinolin-7-yl)-3-cyano-4-iso-propylbenzamide;

N-(3,3-Dimethyl-1,2,3,4-tetrahydro-2-trifluoroacetylisoquinolin-7-yl)-3-chloro-4-iso-propyloxybenzamide;

N-(3,3-Dimethyl-1,2,3,4-tetrahydro-2-trifluoroacetylisoquinolin-7-yl)-3-bromo-4-ethoxybenzamide;

N-(3,3-Dimethyl-1,2,3,4-tetrahydro-2-trifluoroacetylisoquinolin-7-yl)-3-bromo-4-iso-propyloxybenzamide;

N-(3,3-Dimethyl-1,2,3,4-tetrahydroisoquinolin-7-yl)-4-methoxy-3-trifluoromethylbenzamide;

N-(3,3-Dimethyl-1,2,3,4-tetrahydroisoquinolin-7-yl)-3-cyano-4-iso-propylbenzamide;

N-(3,3-Dimethyl-1,2,3,4-tetrahydroisoquinolin-7-yl)-3-chloro-4-iso-propyloxy-benzamide;

N-(3,3-Dimethyl-1,2,3,4-tetrahydroisoquinolin-7-yl)-3-bromo-4-ethoxybenzamide;

N-(3,3-Dimethyl-1,2,3,4-tetrahydroisoquinolin-7-yl)-3-bromo-4-iso-propyloxybenzamide;

N-(2,4,4-Trimethyl-1,2,3,4-tetrahydroisoquinolin-7-yl)-3-cyano-4-iso-propyloxybenzamide;

N-(2,4,4-Trimethyl-1,2,3,4-tetrahydroisoquinolin-7-yl)-3-bromo-4-iso-propyloxybenzamide;

N-(2,4,4-Trimethyl-1,2,3,4-tetrahydroisoquinolin-7-yl)-5-bromo-4-ethoxy-2-methoxybenzamide;

N-(2,4,4-Trimethyl-1,2,3,4-tetrahydroisoquinolin-7-yl)-3-acetyl-4-iso-propyloxybenzamide;

N-(2,4,4-Trimethyl-1,2,3,4-tetrahydroisoquinolin-7-yl)-3-bromo-4-methoxybenzamide;

N-(2,4,4-Trimethyl-1,2,3,4-tetrahydroisoquinolin-7-yl)-3-chloro4-methoxybenzamide;

N-(2,4,4-Trimethyl-1,2,3,4-tetrahydroisoquinolin-7-yl)-3-iodo-4-methoxybenzamide;

N-(2,4,4-Trimethyl-1,2,3,4-tetrahydroisoquinolin-7-yl)-3-fluoro-4-methoxybenzamide;

N-(2,4,4-Trimethyl-1,2,3,4-tetrahydroisoquinolin-7-yl)-3-cyano-4-methoxybenzamide:

N-(2,4,4-Trimethyl-1,2,3,4-tetrahydroisoquinolin-7-yl)-4-methoxy-3-pentafluoroethylbenzamide;

N-(2,4,4-Trimethyl-1,2,3,4-tetrahydroisoquinolin-7-yl)-3-chloro-4-ethoxybenzamide;

N-(2,4,4-Trimethyl-1,2,3,4-tetrahydroisoquinolin-7-yl)-3-cyano-4-ethoxybenzamide;

N-(2,4,4-Trimethyl-1,2,3,4-tetrahydroisoquinolin-7-y )-2,4-dimethoxy-5-trifluoromethylbenzamide;

N-(2,4,4-Trimethyl-1,2,3,4-tetrahydroisoquinolin-7-yl)-3-bromo-4-methylbenzamide;

N-(2,4,4-Trimethyl-1,2,3,4-tetrahydroisoquinolin-$^7$-yl)-3-cyano-4-ethylbenzamide;

N-(2,4,4-Trimethyl-1,2,3,4-tetrahydroisoquinolin-7-yl)-3,5-dichloro-4-ethoxybenzamide;

N-(2,4,4-Trimethyl-1,2,3,4-tetrahydroisoquinolin-5-yl)-5-bromo-4-ethoxy-2-methoxybenzamide;

N-(2,4,4-Trimethyl-1,2,3,4-tetrahydroisoquinolin-5-yl)-5-cyano-2-ethoxy-4-iso-propylbenzamide;

N-(2,4,4-Trimethyl-1,2,3,4-tetrahydroisoquinolin-5-yl)-5-chloro-2-methoxy-4-iso-propyloxybenzamide;

N-(2,4,4-Trimethyl-1,2,3,4-tetrahydroisoquinolin-5-yl)-5-bromo-2-methoxy-4-iso-propylbenzamide;

N-(2,4,4-Trimethyl-1,2,3,4-tetrahydroisoquinolin-5-yl)-4-ethoxy-2-methoxy-5-trifluoromethylbenzamide;

N-(2,4,4-Trimethyl-1,2,3,4-tetrahydroisoquinolin-5-yl)-5-cyano-2,4-diethoxy-benzamide;

N-(2,4,4-Trimethyl-1,2,3,4-tetrahydroisoquinolin-5-yl)-2,4-diethoxy-5-trifluoromethylbenzamide;

N-(2,4,4-Trimethyl-1,2,3,4-tetrahydroisoquinolin-$^5$-yl)-2-methoxy-4-iso-propyl-5-trifluoromethylbenzamide;

N-(4,4-Dimethyl-1,2,3,4-tetrahydroisoquinolin-5-yl)-5-chloro-2-methoxy-4-iso-propoxybenzamide;

N-(4,4-Spirocyclopentyl-2-methyl-1,2,3,4-tetrahydroisoquin-7-yl)-3-bromo-4-ethoxybenzamide;

N-(4,4-Spirocyclopentyl-2-methyl-1,2,3,4-tetrahydroisoquinolin-7-yl)-4-methoxy-3-trifluoromethyl benzamide;

N-(4,4-Spirocyclopentyl-2-methyl-1,2,3,4-tetrahydroisoquinolin-7-yl)-3-cyano-4-iso-propyl benzamide;

N-(4,4-Spirocyclopentyl-2-methyl-1,2,3,4-tetrahydroisoquinolin-7-yl)-3-chloro-4-iso-propyloxybenzamide:

N-(4,4-Spirocyclopentyl-2-methyl-1,2,3,4-tetrahydroisoquinolin-7-yl)-3-bromo-4-ethylbenzamide;

N-(2,4,4-Trimethyl-1,2,3,4-tetrahydroisoquinolin-7-yl)-4-ethoxy-3-trifluoromethyl-benzamide;

N-(2,4,4-Trimethyl-1,2,3,4-tetrahydroisoquinolin-7-yl)-4-iso-propyl-3-trifluoromethylsulfonylbenzamide;

N-(4,4-Dimethyl-1,2,3,4-tetrahydroisoquinolin-7-yl)-3-bromo-4-ethoxybenzamide;

N-(8-Ethyl-2,4,4-trimethyl-1,2,3,4-tetrahydroisoquinolin-7-yl)-3-bromo-4-ethoxybenzamide;

N-(8-Ethyl-2,4,4-trimethyl-1,2,3,4-tetrahydroisoquinolin-7-yl )-4-methoxy-3-trifluoromethylbenzamide;

N-(8-Ethyl-2,4,4-trimethyl-1,2,3,4-tetrahydroisoquinolin-7-yl )-3-bromo-4-iso-propyloxybenzamide;

N-(8-Ethyl-2,4,4-trimethyl-1,2,3,4-tetrahydroisoquinolin-7-yl)-3-cyano-4-iso-propylbenzamide;

N-(8-Ethyl-2,4,4-trimethyl-1,2,3,4-tetrahydroisoquinolin-7-yl)-3-acetyl-4-iso-propyloxybenzamide;
N-(5-Chloro-1,1,2-trimethyl-1,2,3,4-tetrahydroisoquinolin-7-yl)-3-3-bromo-4-ethyl benzamide;
N-(5-Chloro-1,1,2-trimethyl-1,2,3,4-tetrahydroisoquinolin-7-yl)-3-cyano-4-iso-propylbenzamide;
N-(5-Chloro-1,1,2-trimethyl-1,2,3,4-tetrahydroisoquinolin-7-yl)-4-methoxy-3-trifluoromethylbenzamide;
N-(5-Chloro-1,1,2-trimethyl-1,2,3,4-tetrahydroisoquinolin-7-yl)-3-bromo-4-ethoxybenzamide;
N-(1,2-Dimethyl-1,2,3,4-tetrahydroisoquinoline-7-yl)-4-methoxy-3-trifluoromethylbenzamide;
N-(1-Phenyl-2-methyl-1,2,3,4-tetrahydroisoquinolin-7-yl)-4-methoxy-3-trifluoromethylbenzamide;
N-(1-Benzyl-2-methyl-1,2,3,4-tetrahydroisoquinolin-7-yl)-4-methoxy-3-trifluoromethylbenzamide;
N-(1-Iso-propenyl-2-methyl-1,2,3,4-tetrahydroisoquinolin-7-yl)-4-methoxy-3-trifluoromethylbenzamide;
N-(1-Allyl-2-methyl-1,2,3,4-tetrahydroisoquinolin-7-yl)-4-methoxy-3-trifluoromethylbenzamide;
N-(1-Iso-butyl-2-methyl-1,2,3,4-tetrahydroisoquinolin-7-yl)-4-methoxy-3-trifluoromethylbenzamide;
N-(1-Iso-propenyl-2-methyl-1,2,3,4-tetrahydroisoquinolin-7-yl)-3-cyano-4-iso-propylbenzamide;
N-(1-Iso-propenyl-2-methyl-1,2,3,4-tetrahydroisoquinolin-7-yl)-3-cyano-4-iso-propoxybenzamide;
N-(1-Iso-propenyl-2-methyl-1,2,3,4-tetrahydroisoquinolin-7-yl)-3-bromo-4-ethoxybenzamide;
N-(1-Iso-propenyl-2-methyl-1,2,3,4-tetrahydroisoquinolin-7-yl)-3-bromo-4-ethyl benzamide;
N-(1-Iso-propenyl-2-methyl-1,2,3,4-tetrahydroisoquinolin-7-yl)-3-chloro-4-iso-propoxybenzamide;
N-(1-Iso-propyl-2-methyl-1,2,3,4-tetrahydroisoquinolin-7-yl)-4-methoxy-3-trifluoromethylbenzamide;
N-(1,1,2-Trimethyl-1,2,3,4-tetrahydroisoquinolin-7-yl)-3-cyano-4-iso-propyl-benzamide;
N-(1,1,2-Trimethyl-1,2,3,4-tetrahydroisoquinolin-7-yl)-3-bromo-4-ethylbenzamide;
N-(1,1,2-Trimethyl-1,2,3,4-tetrahydroisoquinolin-7-yl)-3-bromo-4-ethoxybenzamide;
N-(1,1,2-Trimethyl-1,2,3,4-tetrahydroisoquinolin-7-yl)-3-chloro-4-iso-propoxybenzamide;
N-(2,3,3-Trimethyl-1,2,3,4-tetrahydroisoquinolin-7-yl)-4-methoxy-3-trifluoromethylbenzamide;
N-(2,3,3-Trimethyl-1,2,3,4-tetrahydroisoquinolin-7-yl)-3-cyano-4-iso-propylbenzamide;
N-(2,3,3-Trimethyl-1,2,3,4-tetrahydroisoquinolin-7-yl)-3-bromo-4-ethylbenzamide;
N-(2,3,3-Trimethyl-1,2,3,4-tetrahydroisoquinolin-7-yl)-3-bromo-4-ethoxybenzamide;
N-(2,3,3-Trimethyl-1,2,3,4-tetrahydroisoquinolin-7-yl)-3-chloro-4-iso-propoxybenzamide;
N-(4,4-Spirocyclobutyl-2-methyl-1,2,3,4-tetrahydroisoquinolin-7-yl)-3-cyano-4-iso-propylbenzamide;
N-(4,4-Spirocyclobutyl-2-methyl-1,2,3,4-tetrahydroisoquinolin-7-yl)-3-bromo-4-ethoxybenzamide;
N-(4,4-Spirocyclobutyl-2-methyl-1,2,3,4-tetrahydroisoquinolin-7-yl)-3-chloro-4-iso-propoxybenzamide;
N-(4,4-Spirocyclobutyl-2-methyl-1,2,3,4-tetrahydroisoquinolin-7-yl)-4-methoxy-3-trifluoromethylbenzamide;
N-(4,4-Spirocyclobutyl-2-methyl-1,2,3,4-tetrahydroisoquinolin-7-yl)-4-ethoxy-3-trifluoromethylbenzamide;
N-(1,2,4,4-Tetramethyl-1,2,3,4-tetrahydroisoquinolin-7-yl)-4-methoxy-3-trifluoromethylbenzamide;
N-(1,2,4,4-Tetramethyl-1,2,3,4-tetrahydroisoquinolin-7-yl)-3-cyano-4-iso-propoxybenzamide;
N-(1,2,4,4-Tetramethyl-1,2,3,4-tetrahydroisoquinolin-7-yl)-3-cyano-4-iso-propylbenzamide;
N-(1,2,4,4-Tetramethyl-1,2,3,4-tetrahydroisoquinolin-7-yl)-3-chloro-4-iso-propoxybenzamide;
N-(1,2,4,4-Tetramethyl-1,2,3,4-tetrahydroisoquinolin-7-yl)-3-bromo-4-ethylbenzamide;
N-(1,2,4,4-Tetramethyl-1,2,3,4-tetrahydroisoquinolin-7-yl)-3-bromo-4-ethoxybenzamide;
N-(1,1,2,5-Tetramethyl-1,2,3,4-tetrahydroisoquinolin-7-yl)-3-bromo-4-ethylbenzamide;
N-(1,1,2,5-Tetramethyl-1,2,3,4-tetrahydroisoquinolin-7-yl)-3-cyano-4-iso-propylbenzamide;
N-(1,1,2,5-Tetramethyl-1,2,3,4-tetrahydroisoquinolin-7-yl)-4-methoxy-3-trifluoromethylbenzamide;
N-(1,1,2-Trimethyl-5-trifluoromethyl-1,2,3,4-tetrahydroisoquinolin-7-yl)-4-methoxy-3-trifluoromethylbenzamide;
N-(1,1,2-Trimethyl-5-trifluoromethyl-1,2,3,4-tetrahydroisoquinolin-7-yl)-3-bromo-4-ethoxybenzamide;
N-(1,1,2-Trimethyl-5-trifluoromethyl-1,2,3,4-tetrahydroisoquinolin-7-yl)-3-cyano-4-ethoxybenzamide;
N-(2,4,4-Trimethyl-1,2,3,4-tetrahydroisoquinolin-7-yl)-4-ethyl-3-trifluoromethyl-benzamide;
N-(2,4,4-Trimethyl-1,2,3,4-tetrahydroisoquinolin-7-yl)-3-acetyl4-iso-propyl-benzamide;
N-(2,4,4-Trimethyl-1,2,3,4-tetrahydroisoquinolin-7-yl)-3-acetyl-4-ethoxybenzamide;
N-[4,4-Dimethyl-2-(2-methoxyethyl)-1,2,3,4-tetrahydroisoquinolin-7-yl]-3-cyano-4-iso-propoxybenzamide;
N-[4,4-Dimethyl-2-(2-methoxyethyl)-1,2,3,4-tetrahydroisoquinolin-7-yl]-3-cyano-4-iso-propylbenzamide;
N-[4,4-Dimethyl-2-(2-methoxyethyl)-1,2,3,4-tetrahydroisoquinolin-7-yl]-4-methoxy-3-trifluoromethylbenzamide;
N-(8-Chloro-2,4,4-trimethyl-1,2,3,4-tetrahydroisoquinolin-7-yl)-3-bromo-4-iso-propoxybenzamide;
N-(8-Chloro-2,4,4-trimethyl-1,2,3,4-tetrahydroisoquinolin-7-yl)-4-ethyl-3-trifluoromethylbenzamide;

N-(8-Chloro-2,4,4-trimethyl-1,2,3,4-tetrahydroisoquinolin-7-yl)-3-acetyl-4-iso-propylbenzamide;

N-(8-Chloro-2,4,4-trimethyl-1,2,3,4-tetrahydroisoquinolin-7-yl)-3-cyano-4-methoxybenzamide;

N-(8-Chloro-2,4,4-trimethyl-1,2,3,4-tetrahydroisoquinolin-7-yl)-4-methoxy-3-trifluoromethylbenzamide;

N-(8-Chloro-2,4,4-trimethyl-1,2,3,4-tetrahydroisoquinolin-7-yl)-3-chloro-4-ethoxybenzamide;

N-(8-Chloro-2,4,4-trimethyl-1,2,3,4-tetrahydroisoquinolin-7-yl)-3-bromo-4-ethoxybenzamide;

N-(8-Chloro-2,4,4-trimethyl-1,2,3,4-tetrahydroisoquinolin-7-yl)-3-bromo-4-iso-propylbenzamide;

N-(8-Chloro-2,4,4-trimethyl-1,2,3,4-tetrahydroisoquinolin-7-yl)-3-cyano-4-ethylbenzamide;

N-(2,4,4-Trimethyl-1,2,3,4-tetrahydroisoquinolin-7-yl)-4-iso-propoxy-3-trifluoromethylbenzamide;

N-(8-Ethyl-2,4,4-trimethyl-1,2,3,4-tetrahydroisoquinolin-7-yl)-3-bromo-4-methoxybenzamide;

N-(8-Ethyl-2,4,4-trimethyl-1,2,3,4-tetrahydroisoquinolin-7-yl)-3-chloro4-methoxybenzamide;

N-(8-Ethyl-2,4,4-trimethyl-1,2,3,4-tetrahydroisoquinolin-7-yl)-3-chloro-4-ethoxybenzamide;

N-(8-Ethyl-2,4,4-trimethyl-1,2,3,4-tetrahydroisoquinolin-7-yl)-3-bromo-4-ethylbenzamide;

N-(8-Methyl-2,4,4-trimethyl-1,2,3,4-tetrahydroisoquinolin-7-yl)-3-bromo-4-ethoxybenzamide;

N-(8-Methyl-2,4,4-trimethyl-1,2,3,4-tetrahydroisoquinolin-7-yl)-4-methoxy-3-trifluoromethylbenzamide;

N-(8-Methyl-2,4,4-trimethyl-1,2,3,4-tetrahydroisoquinolin-7-yl)-3-chloro-4-ethoxybenzamide;

N-(8-Methyl-2,4,4-trimethyl-1,2,3,4-tetrahydroisoquinolin-7-yl)-3-cyano-4-ethylbenzamide;

N-(8-Bromo-2,4,4-trimethyl-1,2,3,4-tetrahydroisoquinolin-7-yl)-3-bromo-4-methoxybenzamide;

N-(8-Bromo-2,4,4-trimethyl-1,2,3,4-tetrahydroisoquinolin-7-yl)-4-methoxy-3-trifluoromethylbenzamide;

N-(2,4,4-Trimethyl-1,2,3,4-tetrahydroisoquinolin-7-yl)-3-acetyl-4-ethylbenzamide;

N-(2,4,4-Trimethyl-1,2,3,4-tetrahydroisoquinolin-7-yl)-4-ethoxy-3-propionylbenzamide;

N-(2,4,4-Trimethyl-1,2,3,4-tetrahydroisoquinolin-7-yl)-4-iso-propoxy-3-propionylbenzamide;

N-(2,4,4-Trimethyl-1,2,3,4-tetrahydroisoquinolin-7-yl)-3-iso-butyroyl-4-methoxybenzamide;

N-(2,4,4-Trimethyl-1,2,3,4-tetrahydroisoquinolin-7-yl)-4-ethoxy-3-iso-butyroyl benzamide;

N-(2,4,4-Trimethyl-1,2,3,4-tetrahydroisoquinolin-7-yl )-3-iso-butyroyl-4-iso-propoxybenzamide;

N-(2,4,4-Trimethyl-1,2,3,4-tetrahydroisoquinolin-7-yl)-3-iso-butyroyl-4-n-propoxybenzamide;

N-(4,4-Dimethyl-1,2,3,4-tetrahydroisoquinolin-7-yl )-3-acetyl-4-ethoxybenzamide;

N-(8-Bromo-4,4-dimethyl-1,2,3,4-tetrahydroisoquinolin-7-yl)-4-methoxy-3-trifluoromethylbenzamide;

N-(4,4,8-Trimethyl-1,2,3,4-tetrahydroisoquinolin-7-yl)-4-methoxy-3-trifluoromethylbenzamide;

N-(4,4,8-Trimethyl-1,2,3,4-tetrahydroisoquinolin-7-yl)-3-bromo-4-ethoxybenzamide;

N-(4,4-Dimethyl-8-ethyl-1,2,3,4-tetrahydroisoquinolin-7-yl)-4-methoxy-3-trifluoromethylbenzamide;

N-(4,4-Dimethyl-8-ethyl-1,2,3,4-tetrahydroisoquinolin-7-yl)-3-bromo-4-ethoxybenzamide;

N-(4,4-Dimethyl-8-ethyl-1,2,3,4-tetrahydroisoquinolin-7-yl)-3-chloro-4-ethoxybenzamide;

N-(8-Cyano-2,4,4-trimethyl-1,2,3,4-tetrahydroisoquinolin-7-yl)-4-methoxy-3-trifluoromethylbenzamide;

N-(4,4-Dimethyl-1,2,3,4-tetrahydroisoquinolin-7-yl)-3-chloro-4-methoxybenzamide;

N-(4,4,8-Trimethyl-1,2,3,4-tetrahydroisoquinolin-7-yl)-3-acetyl-4-ethoxybenzamide;

N-(4,4-Dimethyl-8-ethyl-1,2,3,4-tetrahydroisoquinolin-7-yl)-3-acetyl-4-ethoxybenzamide;

N-(4,4-Dimethyl-8-ethyl-1,2,3,4-tetrahydroisoquinolin-7-yl)-3-acetyl-4-methoxybenzamide;

N-(4,4-Dimethyl-8-ethyl-1,2,3,4-tetrahydroisoquinolin-7-yl)-4-methoxy-3-propionyl benzamide;

N-(8-Chloro-4,4-dimethyl-1,2,3,4-tetrahydroisoquinolin-7-yl)-4-methoxy-3-trifluoromethylbenzamide;

N-(8-Bromo-2,3,3-trimethyl-1,2,3,4-tetrahydroisoquinolin-7-yl)-4-methoxy-3-trifluoromethyl benzamide;

N-(8-Chloro-2,3,3-trimethyl-1,2,3,4-tetrahydroisoquinolin-7-yl)-3-chloro-4-ethoxy benzamide;

N-(8-Chloro-2,3,3-trimethyl-1,2,3,4-tetrahydroisoquinolin-7-yl)-3-chloro-4-methoxy benzamide;

N-(8-Chloro-2,3,3-trimethyl-1,2,3,4-tetrahydroisoquinolin-7-yl)-3-fluoro-4-methoxy benzamide;

N-(8-Chloro-3,3-dimethyl-1,2,3,4-tetrahydroisoquinolin-7-yl)-4-methoxy-3-trifluoromethyl benzamide;

N-(5-Iodo-1,1,2-trimethyl-1,2,3,4-tetrahydroisoquinolin-7-yl)-4-methoxy-3-trifluoromethyl benzamide;

N-(5-Cyano-1,1,2-trimethyl-1,2,3,4-tetrahydroisoquinolin-7-yl)-4-methoxy-3-trifluoromethyl benzamide;

N-(8-Bromo-3,3-dimethyl-1,2,3,4-tetrahydroisoquinolin-7-yl )-4-methoxy-3-trifluoromethylbenzamide;

N-(1,1,2,5-Tetramethyl-1,2,3,4-tetrahydroisoquinolin-7-yl)-3-bromo-4-ethoxybenzamide;

N-[4,4-Dimethyl-2-(2-methoxyethyl)-1,2,3,4-tetrahydroisoquinolin-7-yl]-3-bromo-4-iso-propoxybenzamide, and;

N-(6-Bromo-2,4,4-trimethyl-1,2,3,4-tetrahydroisoquinolin-7-yl)-3-bromo-4-ethoxybenzamide.

When synthesised, these compounds are often in salt form, such as the hydrochloride or trifluoroacetate, and such salts also form part of this invention. Such salts may be used in preparing pharmaceutically acceptable salts. The compounds and their salts may be obtained as solvates, such as hydrates, and these also form part of this invention.

The above compounds and pharmaceutically acceptable salts thereof, especially the hydrochloride, and pharmaceutically acceptable solvates, especially hydrates, form a preferred aspect of the present invention.

The administration of such compounds to a mammal may be by way of oral, parenteral, sub-lingual, nasal, rectal, topical or transdermal administration.

An amount effective to treat the disorders hereinbefore described depends on the usual factors such as the nature and severity of the disorders being treated and the weight of the mammal. However, a unit dose will normally contain 1 to 1000 mg, suitably 1 to 500 mg, for example an amount in the range of from 2 to 400 mg such as 2, 5, 10, 20, 30, 40, 50, 100, 200, 300 and 400 mg of the active compound. Unit doses will normally be administered once or more than once per day, for example 1, 2, 3, 4, 5 or 6 times a day, more usually 1 to 4 times a day, such that the total daily dose is normally in the range, for a 70 kg adult of 1 to 1000 mg, for example 1 to 500 mg, that is in the range of approximately 0.01 to 15 mg/kg/day, more usually 0.1to 6 mg/kg/day, for example 1 to 6 mg/kg/day.

It is greatly preferred that the compound of the invention is administered in the form of a unit-dose composition, such as a unit dose oral, including sub-lingual, rectal, topical or parenteral (especially intravenous) composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents. tabletting agents, lubricants, disintegrants, colorants, flavourings, and wetting agents. The tablets may be coated according to well known methods in the art. Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents. Oral formulations also include conventional sustained release formulations, such as tablets or granules having an enteric coating.

For parenteral administration, fluid unit dose forms are prepared containing the compound and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the.

As is common practice, the compositions will usually be accompanied by written or printed directions for use in the medical treatment concerned.

Accordingly, the present invention further provides a pharmaceutical composition for use in the treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, and amyotrophic lateral sclerosis (ALS) which comprises a compound of formula (I), or a pharmaceutically acceptable salt or solvate thereof, and a pharmaceutically acceptable carrier.

The present invention also provides a method of treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, and amyotrophic lateral sclerosis (ALS) comprising administering to the sufferer in need thereof an effective or prophylactic amount of a compound of formula (I), or a pharmaceutically acceptable salt or solvate thereof.

In a further aspect the invention provides the use of a compound of formula (I), or a pharmaceutically acceptable salt or solvate thereof, for the manufacture of a medicament for the treatment and/or prophylaxis of anxiety, mania, depression, panic disorders and/or aggression, disorders associated with a subarachnoid haemorrhage or neural shock. the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, and amyotrophic lateral sclerosis (ALS).

In a further aspect the invention provides the use of a compound of formula (I), or a pharmaceutically acceptable salt or solvate, thereof as a therapeutic agent, in particular for the treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, multiple sclerosis (MS) and motor neurone disease, ataxias, muscular rigidity (spasticity), temporomandibular joint dysfunction, and amyotrophic lateral sclerosis (ALS).

Another aspect of the invention is a process for the preparation of compounds of formula (I) as herein before described or salts thereof or solvates thereof which comprises reacting a compound of formula (II)

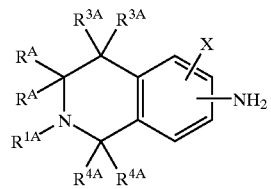

(II)

where $R^A$, $R^{1A}$, $R^{3A}$, $R^{4A}$ are R, $R^1$, $R^3$, $R^4$ as defined for formula (I) or a group or groups convertible to R, $R^1$, $R^3$, $R^4$ with a compound of formula (III)

(III)

where Y is Cl or OH, and $R^{2A}$ groups are independently $R^2$ as defined for formula (I) or a group or groups convertible to $R^2$, and where required converting an $R^A$, $R^{1A}$, $R^{2A}$, $R^{3A}$, $R^{4A}$ group to a R, $R^1$, $R^2$, $R^3$, $R^4$ group, converting one R, $R^1$, $R^2$, $R^3$, $R^4$ group to another R, $R^1$, $R^2$, $R^3$, $R^4$ group, or converting a salt product to the free base or another pharmaceutically acceptable salt, or separating any enantiomers, or converting a free base product to a pharmaceutically acceptable salt.

Reaction of a compound of formula (III) which is a benzoyl chloride derivative (Y=Cl) will lead directly to the hydrochloride salt. Suitable solvents include ethyl acetate or dichloromethane, optionally in the presence of a base such as triethylamine. When the compound of formula (III) is a benzoic acid derivative (Y=OH), conventional conditions for condensation of aromatic acids with amines may be used, for example reacting the components in a mixture of ethyl-(dimethylaminopropyl)-carbodiimide/hydroxybenzotriazole in a suitable inert solvent such as dimethyl formamide.

Conversions of an $R^A$, $R^{1A}$, $R^{2A}$, $R^{3A}$, $R^{4A}$ group to a R, $R^1$, $R^2$, $R^3$, $R^4$ group typically arise when a protecting group is needed during the above coupling reaction or during the preparation of the reactants by the procedures described below. Interconversion of one R, $R^1$, $R^2$, $R^3$, $R^4$ group to another typically arises when one compound of the invention is used as the immediate precursor of another compound of the invention or when it is easier to introduce a more complex or reactive substituent at the end of a synthetic sequence.

Compounds of formula (II) when $R^4$=H or alkyl may be prepared from the corresponding isoquinoline of formula (IV)

(IV)

by reaction with a compound $R^{1A}Z$ where Z is a leaving group such as halogen, especially iodo, or tosylate to obtain an intermediate of formula (V)

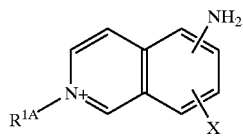

(V)

which is reacted with an $R^{4A}$ containing Grignard reagent under conventional conditions to obtain a dihydroisoquinoline of formula (VI)

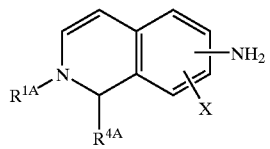

(VI)

which can be hydrogenated, for example using hydrogen and a palladium/activated carbon catalyst, to obtain a tetrahydroisoquinoline of formula (II). Alternatively the compound of formula (IV) may be a nitro-isoquinoline, and the nitro group is converted to an amino group in the hydrogenation step.

When the intended $R^1$ is hydrogen, the N of the isoquinoline is preferably protected conventionally, for example by making $R^{1A}$ benzyl, or 4-methoxybenzyl during introduction of the $R^4$ group via the Grignard reagent. Again protection is preferably provided prior to formation of the benzamide, for example by tert.-butoxycarbonyl and then deprotected under standard conditions, for example using trifluoroacetic acid/methylene chloride.

Amino/nitro-isoquinolines of formulae (IV) and the reagents used are commercially available, or can be prepared from commercially available materials using conventional procedures described in the literature (eg. I. W. Matheson et al, J. Med. Chem. 1973, 16, 332).

Compounds of formula (II) with di-$R^3$ substitution and X is hydrogen may be prepared from the corresponding nitro-isoquinoline dione of formula (VII), by converting the nitro group to amino by catalytic hydrogenation as above and subsequently removing the dione groups by reduction with diborane. The nitro-dione may be obtained by treating a di-$R^3$ isoquinoline dione [prepared using the procedure of H. Takechi et al., Synthesis. 1992, 778] with fuming nitric acid. $R^{1A}$ groups may be introduced as described above.

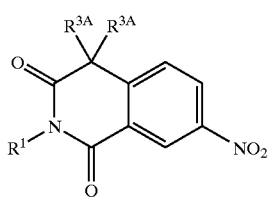

(VII)

Compounds of formula (II) where both $R^4$ are alkyl may be prepared from the corresponding 1-alkyl-3,4-dihydroisoquinoline by nitration [using procedures by R. D. Larsen et al, J. Org. Chem., 1991 56 6034 and A. P. Venkov and S. S. Abeghe, Syn. Commun., 1996 26 127] followed by quaternisation and treatment with an $R^4$ Grignard reagent as described above.

Compounds of formula (II) where R is alkyl may be prepared from the corresponding phenylethylamines using the modified Pictet-Spengler procedure of T. J. N. Watson J. Org. Chem., 1998, 63, 406.

When the substituent X is other than hydrogen it may be introduced during any of the procedures above, or may be present on commercially available starting materials usable in the above described procedures. Most suitably the substituent X is introduced into an amino/nitro compound of formula (II) in which X is hydrogen. For example X as halogen may be incorporated directly by halogenation or via an amino group using Sandmeyer chemistry as illustrated in the descriptions below. Interconversions of X=halogen to X=alkyl or trifluoroacetyl may be carried out using Pd(0) or Cu(I) chemistry respectively as detailed below.

Compounds of formula (III) may be prepared by further substitution of commercially available benzoic acid derivatives using conventional procedures, or by oxidation of corresponding substituted benzyl alcohols. Alternatively benzoic acids can be prepared from correpondingly substituted phenols, for example by formation of the acetate, conversion to an acetophenone and then to the desired acid.

Where the above described intermediates are novel compounds, they also form part of this invention.

The preparation of compounds of this invention is further illustrated by the following Preparations, Descriptions and Examples. The utility of compounds of this invention is shown by the Pharmacological Data that follow the Examples.

DESCRIPTION 1

7-Nitro-2,4-trimethyl-4H-isoquinoline-1,3-dione 2,4,4-Trimethyl-4H-isoquinoline-1,3-dione (5 g, 24.6 mmol) [prepared according to H. Takechi et al., Synthesis. 1992, 778] was dissolved in concentrated sulfuric acid (50 ml) at 0° C. Fuming nitric acid (2.5 ml) was added dropwise over 5 min and the reaction warmed to 25° C. After stirring for 30 min at 25° C. the reaction mixture was poured into ice water (100 ml) and the organics extracted into dichloromethane (3×50 ml). The combined organic extracts were dried over magnesium sulfate and evaporated in vacuo to give the title compound (5.31 g, 86%).

$^1$H NMR (250 MHz, CDCl$_3$)δ: 1.70 (6H, s), 3.42 (3H, s), 7.69 (1H, d, J=9 Hz), 8.46 (1H, dd, J=9, 2 Hz), 9.07 (1H, d, J=2 Hz); $^m/_z$ (API$^+$): 249 (M+H)$^+$

DESCRIPTION 2

7-Amino-2,4,4,-trimethyl-4H-isoquinoline-1,3-dione

7-Nitro-2,4,4-trimethyl4H-isoquinoline-1,3-dione (45 g, 20 mmol) was dissolved in a methanol (500 ml)/dichloromethane (100 ml) mixture and treated with 10% Pd/C (0.5 g). The reaction mixture was hydrogenated for 2 h before removal of the palladium catalyst by filtration through Celite. The filtrate was evaporated to dryness in vacuo to give the title compound (4.4 g, quant). $^1$H NMR (250 MHz, CDCl$_3$)≃:1.58 (6H, s), 3.36 (3H, s), 3.83 (2H, brs), 6.95 (1H, dd, J=6, 3 Hz), 7.24 (1H, d, J=6 Hz), 7.48 (1H, d, J=3 Hz); $^m/_z$ (API$^+$): 219 (M+H)$^+$

DESCRIPTION 3

7-Amino-2,4,4-trimethyl-1,2,3,4-tetrahydroisoquinoline, Hydrochloride

D2 (4 g, 18.3 mmol) was dissolved in tetrahydrofuran (400 ml) and heated at reflux (~61° C.). Borane-tetrahydrofuran complex (88 ml, 1M solution in THF) was added dropwise to the mixture and heating continued for a further 3 h. The cooled reaction (0° C.) was treated with methanol (400 ml) dropwise to destroy residual borane, followed by evaporation in vacuo. The resultant residue was heated at reflux in 3N HCl (400 ml) for 30 min. The mixture was cooled to 0° C. and treated with NaOH pellets until basic (pH 9). The free amine was extracted into dichloromethane (4×100 ml) before drying over magnesium sulfate and evaporation in vacuo. The resulting light brown oil was dissolved in dichloromethane (50 ml) and treated with hydrogen chloride (1M solution in ether) until acidic (pH 2). Solvent removal in vacuo followed by trituration with ether yielded the title compound as an off-white powder (3.3 g, 79%).

$^1$H NMR (free base 250 MHz, CDCl$_3$)δ: 1.25 (6H, s), 2.37 (2H, s), 2.39 (3H, s), 3.43 (2H, s), 3.51 (2H, brs), 6.32 (1H, d, J=2 Hz), 6.54 (1H, dd, J=8, 2 Hz), 709 (1H, d, J=8 Hz); $^m/_z$ (API$^+$): 191 (M+H)$^+$

DESCRIPTION 4

3,4-Dihydro-3,3-dimethyl-7-nitroisoquinoline

To a stirred solution of potassium nitrate (2.53 g) in sulfuric acid (14 ml) at 0° C. was added dropwise a solution of 3,4-dihydro-3,3-dimethyl isoquinoline (3.68 g; 23 mmol) [prepared according to the procedure of T. J. N. Watson, *J. Org. Chem.*, 1998, 63, 406] in sulfuric acid (13.5 ml). The resultant solution was stirred at room temperature for 1.5 h and then heated to 60° C. for 4.5 h. The solution was then cooled to room temperature, and poured on to ice.; 0.880 ammonia was added until the solution was neutral, and the product was extracted into dichloromethane (×3). The combined organic phases were, dried over magnesium sulphate, and then evaporated in vacuo to afford the title compound (4.22 g). $^1$H NMR (CDCl$_3$)δ: 1.27 (6H, s), 2.85 (2H, s), 7.34 (1H, d, J=8 Hz), 8.17 (1H, d, J=2Hz), 8.23 (1H, dd, J=8, 2Hz), 8.33 (1H, s).

DESCRIPTION 5

3,3-Dimethyl-7-nitro-1,2,3,4-tetrahydroisoquinoline

Sodium borohydride (1.57 g; 41.38 mmol) was added portionwise to a solution of 3,4-dihydro-3,3-dimethyl-7-nitroisoquinoline (4.22 g; 20.69 mmol) in methanol (150 ml). The resultant solution was stirred at 25° C. for 2 h. The methanol was evaporated in vacuo and the residue partitioned between water and dichloromethane. The organic layer was dried over sodium sulphate and then evaporated in vacuo to afford the title compound (3.81 g).

$^1$H NMR (CDCl$_3$)δ: 1.20 (6H, s), 1.40–1.53 (1H, brs), 2.72 (2H, s), 4.14 (2H, s), 7.20 (1H, d, J=8Hz), 7.37 (1H, s), 7.98 (1H, dd, J=8,2Hz).

DESCRIPTION 6

3,3-Dimethyl-7-nitro-1,2,3,4-tetrahydro-2-trifluoroacetylisoquinoline

A solution of 2,6-lutidine (2.29 ml; 19.69 mmol) and 3,3-dimethyl-7-nitro-1,2,3,4-tetrahydroisoquinoline (3.7 g: 17.9 mmol) in dichloromethane (150 ml) was treated dropwise, with ice cooling, trifluoroacetic anhydride (2.53 ml, 17.9 mmol) in dichloromethane (50 ml). The reaction was then allowed to warm to 25° C. and stirred for 18 h. The resultant mixture was washed with 5M HCl, brine, dried over sodium sulphate, and then evaporated in vacuo to afford the title compound (5.82 g).

$^1$H NMR (CDCl$_3$) δ: 1.51 (6H, s), 2.97 (2H, s), 4.61 (2H, s), 7.43 (1H, d, J=8 Hz), 8.12 (1H, d, J=2 Hz), 8.24 (1H, dd, J=8, 2 Hz).

DESCRIPTION 7

7-Amino-3,3-dimethyl-1,2,3,4-tetrahydro-2-trifluoroacetyl Isoquinoline

The title compound (2 g) was prepared from D6 (5.80 g; 19.2 mmol) in a manner similar to that of Description 2.

$^1$H NMR (CDCl$_3$) δ: 1.45 (6H, s), 2.73 (2H, s), 3.67 (2H, brs), 4.38 (2H, s), 6.56 (1H, d, J=2 Hz), 6.63 (1H, dd, J=8, 2 Hz), 6.99 (1H, d, J=8 Hz).

DESCRIPTION 8

2-Nitrophenyldimethylacetonitrile

Prepared according to the procedure of Hanna et al, J.Org.Chem., 1991 56 7188–90.

$^1$H NMR (CDCl$_3$) δ: 1.89 (6H, s), 7.26–7.70 (4H, m).

DESCRIPTION 9

2-Methyl-2-(2-nitrophenyl)propylamine $^1$H NMR (CDCl$_3$) δ: 1.36 (6H, s), 2.93 (2H, s), 7.32 (2H, m), 4.48 (2H, m).

DESCRIPTION 10

2,2,2-Trifluoro-N-[2-methyl-2-(2-nitrophenyl)propyl]acetamide $^1$H NMR (CDCl$_3$) δ: 1.43 (6H, s), 3.70 (2H, d, J=7 Hz), 6.35 (1H, brs), 7.44 (2H, m), 7.53 (2H, m).

DESCRIPTION 11

4,4-Dimethyl-5-nitro-2-trifluoroacetyl-1,2,3,4-tetrahydroisoquinoline $^1$H NMR (CDCl$_3$) δ: 1.41 (6H, s), 3.49, 3.69 (2H, 2s), 4.84, 4.91 (2H, 2s), 7.35 (3H, m).

DESCRIPTION 12

4,4-Dimethyl-5-nitro-1,2,3,4-tetrahydroisoquinoline $^1$H NMR (CDCl$_3$) δ: 1.36 (6H, s), 2.78 (2H, s), 4.12 (2H, s), 7.16 (3H, m).

DESCRIPTION 13

5-Nitro-2,4,4-trimethyl-1,2,3,4-tetrahydroisoquinoline $^1$H NMR (CDCl$_3$) δ: 1.39 (6H, s), 2.32 (2H, s), 2.40 (3H, s), 3.62 (2H, s), 7.18 (3H, m).

DESCRIPTION 14

5-Amino-2,4,4-trimethyl-1,2,3,4-tetrahydroisoquinoline $^1$H NMR (CDCl$_3$) δ: 1.40 (6H, s), 2.30 (2H, s), 2.36 (3H, s), 3.48 (2H, s), 3.74 (2H, brs), 6.48 (2H, m), 6.92 (1H, t, J=7 Hz).

DESCRIPTION 15

2-Methyl-4H-isoquinolin-1,3-dione

The title compound was prepared using a procedure similar to that employed for Description 1.

¹H NMR (CDCl₃) δ: 3.38 (3H, s), 4.05 (2H, s), 7.28 (1H, d, obscurred by CHCl₃, J=7 Hz), 7.44 (1H, t, J=7 Hz), 7.59 (1H, m, J=7, 1 Hz), 8.22 (1H, dd, J=7, 2 Hz).

DESCRIPTION 16

4,4-Spirocyclopentyl-2-methyl-4H-isoquinoline-1,3-dione

To a solution of 2-methyl-4H-isoquinoline-1,3-dione (1.5 g; 8.57 mmol) and 1,4-dibromobutane (1.54 ml; 12.85 mmol) in N,N-dimethylformamide (50 ml) was added potassium carbonate (1.77 g; 12.85 mmol). This suspension was stirred for 18 h at 25° C., heated to 80° C. for 6 h and filtered. The filtrate was concentrated in vacuo and the residue partitioned between ethyl acetate and water. The organic phase was dried (Na₂SO₄), and the solvent removed in vacuo. The residue was purified by column chromatography, eluting with 1% methanol in dichloromethane, to afford the title compound (1.155 g; 59%).

¹H NMR (CDCl₃) δ: 1.96–2.16 (6H, m), 2.50 (2H, m), 3.38 (3H, s), 7.40 (2H, m), 7.62 (1H, m, J=8, 1 Hz), 8.20 (1H, dd, J=8, 1 Hz).

DESCRIPTION 17

4,4-Spirocyclopentyl-2-methyl-7-nitro-4H-isoquinoline-1,3-dione

D 16 (1.15 g; 5.02 mmol) was nitrated in a manner similar to that of Description 4 to afford the title compound (1.54 g; 100%).

¹H NMR (CDCl₃) δ: 1.95–2.23 (6H, m), 2.58 (2H, m), 3.41 (3H, s), 7.59 (1H, d, J=9 Hz), 8.44 (1H, dd, J=9, 3 Hz), 9.04 (1H, d, J=3 Hz).

DESCRIPTION 18

7-Amino-4,4-spirocyclopentyl-2-methyl-4H-isoquinoline-1,3-dione

D17 (1.54 g; 5.62 mmol) was hydrogenated in a manner similar to that of Description 2 to afford the title compound (1.34 g; 98%).

¹H NMR (CDCl₃) δ: 1.98 (6H, m), 2.46 (2H, m), 3.35 (5H, m), 6.95 (1H, d, J=8 Hz), 7.17 (1H, d, J=8 Hz), 7.47 (1H, s).

DESCRIPTION 19

7-Amino-4,4-spirocyclopentyl-2-methyl-1,2,3,4-tetrahydroisoquinoline Hydrochloride D18 (1.34 g; 5.50 mmol) in dry tetrahydrofuran (120 ml) was reduced with diborane in a manner similar to D3 to afford the title compouhnd (1.28 g; 92%).

¹H NMR (CDCl₃) δ 1.73 (8H, m), 2.34 (2H, s), 2.39 (3H, s), 3.43 (2H, s), 3.51 (2H, s), 6.30 (1H, d, J=2 Hz), 6.55 (1H, dd, J=8, 2 Hz), 7.06 (1H, d, J=8 Hz).

DESCRIPTION 20

7-Amino-8-bromo-2,4,4-trimethyl-1,2,3,4-tetrahydroisoquinoline

To a solution of 7-amino-2,4,4-trimethyl-1,2,3,4-tetrahydroisoquinoline from D3 (7 g) in acetonitrile (200 ml), was added N-bromo succinimide (7.21 g) portionwise over 10 min. The reaction mixture was cooled in an ice/methanol bath to prevent any large exotherm. and then stirred under argon for 45 min. The reaction was allowed to warm to 25° C., diluted with water and extracted with ethyl acetate. The combined organic extracts were washed with brine, dried (MgSO₄) and evaporated to dryness in vacuo. The resultant brown solid was purified using dry flash column chromatography with ethyl acetate. Combination of appropriate fractions gave the title compound as an orange gum (3.95 g).

¹H NMR (CDCl₃) δ: 1.26 (6H, s), 2.33 (2H, s), 2.45 (3H, s), 3.49 (2H, s), 4.00 (2H, s), 6.67 (1H, d), 7.08 (1H, d).

DESCRIPTION 21

7-Amino-8-ethyl-2,4,4-trimethyl-1,2,3,4-tetrahydroisoquinoline

A solution of D20 (3.95 g) and lithium chloride (1.87 g) in dry dimethylformamide (120 ml) was treated with tetraethyl tin (5.81 ml) followed by a catalytic amount of bis(triphenylphosphine) Palladium (II) dichloride (350 mg). The reaction mixture was then stirred under argon at 120° C. overnight. After cooling, the solvent was removed in vacuo and the residual oil was dissolved in dichloromethane and filtered through Celite, washing well with dichloromethane. The organic layer was evaporated to dryness in vacuo to afford a dark orange oil which was purified using dry flash column chromatography eluting with ethyl acetate. Combination of appropriate fractions gave the title compound as a yellow gum (1.6 g).

¹H NMR (CDCl₃) δ: 1.14 (3H, t), 1.27 (6H, d), 2.33 (2H, s), 2.47 (5H, m), 3.51 (2H, s), 6.60 (1H, d), 7.02 (1H, d).

DESCRIPTION 22

1,2-Dimethyl-3,4-dihydroisoquinolinium Iodide

1-Methyl-3,4-dihydroisoquinoline (780 mg) was dissolved in acetone (7 ml) and iodomethane (0.38 ml) added. The solution was allowed to stand overnight at room temperature. The product was obtained as pale yellow crystals (1.4 g).

¹H NMR (250 MHz, d₆DMSO) δ: 2.66 (3H, s), 2.99 (2H, t, J=7.5 Hz), 3.56 (3H, s), 3.88 (2H, t, J=7.5 Hz), 7.36 (2H, m), 7.60 (1H, t, J=7.5 Hz). 7.94 (1H, d, J=7.5 Hz).

DESCRIPTION 23

1,1,2-Trimethyl-1,2,3,4-tetrahydroisoquinoline

Methyl magnesium bromide (4.5 ml, 3M in Et₂O) was added to a stirred suspension of 1,2-dimethyl-3,4-dihydroisoquinolinium iodide (1.3 g) in dry THF (20 ml) at −70° C. under argon. After 1 h, the mixture was allowed to warm slowly to room temperature and stirred overnight. The mixture was quenched by cautious addition of water and extracted with ethyl acetate. The extract was washed with water, brine, dried (MgSO₄) and evaporated in vacuo to give the title compound as a pink oil (730 mg).

¹H NMR (250 MHz, CDCl₃) δ: 1.40 (6H, s), 2.44 (3H, s), 2.87 (4H, s), 7.15 (4H, m).

DESCRIPTION 24

1,1,2-Trimethyl-7-nitro-1,2,3,4-tetrahydroisoquinoline

The amine D23 (620 mg) was converted into the sulfate salt and added to an ice-cooled solution of potassium nitrate (420 mg) in conc. H₂SO₄ (5 ml). When the addition was complete the ice bath was removed and the mixture stirred overnight at room temperature. The mixture was poured onto ice, made basic with conc. aq. ammonia and extraction with dichloromethane yielded an oil which was purified by chromatography eluting with dichloromethane:methanol:ammonia. The product was obtained as a red oil (430 mg) [predominantly the desired 7-nitro derivative].

$^1$H NMR (250 MHz, CDCl$_3$) δ: 1.45 (6H, s), 2.45 (3H, s), 2.92 (4H, m), 7.20 (1H, d, J=8 Hz), 7.95 (1H, dd, J=8, 2 Hz), 8.15 (1H, d, J=2 Hz).

DESCRIPTION 25

1,1,2-Trimethyl-5-iodo-7-nitro-1,2,3,4-tetrahydroisoquinoline

N-Iodosuccinimide (2.24 g) was added in portions to a stirred solution of the 7-nitro derivative D24 (1.1 g) in trifluoromethanesulfonic acid (15 ml) with ice-cooling. The mixture was then stirred at 25° C. for 18 h, diluted with ice, made basic with aq. NaOH and extracted with ethyl acetate. The extract was washed with water, aq. sodium thiosulfate, brine and dried (MgSO$_4$). Evaporation in vacuo gave the product as a red oil (1.69 g).

$^1$H NMR (250 MHz; CDg) δ: 1.44 (6H, s), 2.44 (3H, s), 2.90 (4H, m), 8.17 (1H, d, J=2 Hz), 8.52 (1H, d, J=2 Hz).

DESCRIPTION 26

1,1,2-Trimethyl-5-chloro-7-nitro-1,2,3,4-tetrahydroisoquinoline

The iodo compound D25 (1.69 g) was dissolved in dry DMF (20 ml) and copper (I) iodide (1.5 g) added. The mixture was stirred at 125° C. under argon for 24 h. After cooling the mixture was concentrated and diluted with water and ethyl acetate. A brown precipitate was filtered off and discarded. The organic layer from the filtrate was separated, washed with water, brine, dried (MgSO$_4$) and evaporated to dryness. The crude product was purified by chromatography on silica gel eluting with dichloromethane:methanol:ammonia. The title compound was obtained as a red oil (430 mg).

$^1$H NMR (CDCl$_3$): δ: 1.51 (6H, s), 2.44 (3H, s), 2.95 (4H, m). 8.08 (2H, brs).

DESCRIPTION 27

7-Amino-5-chloro-1,1,2-trimethyl-1,2,3,4-tetrahydroisoquinoline

The nitro compound D26 was dissolved in ethanol (30 ml) and conc. HCl (3 ml) added. The solution was cooled and tin (II) chloride dihydrate (1.48 g) added. The mixture was heated at 60° C. for 2 h and then allowed to stand at room temperature. The reaction mixture was then diluted with ice, made basic with 40% aq. sodium hydride and extracted with ethyl acetate. The extract was washed with brine, dried (MgSO$_4$) and evaporated to give the title compound as a brown oil (360 mg) which was used without purification.

$^m/_z$ (API$^+$): 225, 227 (MH$^+$).

DESCRIPTION 28

7-Amino-3,4-dihydroisoquinoline

7-Nitro-3,4-dihydroisoquinoline (0.60 g, 3.4 mmol) [prepared according to the procedure of A. P. Venkov et al, Syn. Commun., 1996 26 127] was dissolved in ethanol (100 ml) and heated to 60° C. This hot solution was treated with a solution of tin (II) chloride dihydrate (3.08 g, 13.7 mmol) in conc. HCl (10 ml). The resultant mixture was heated at 60° for 1 h. Upon cooling, the reaction mixture was poured into water (100 ml) and basified (pH 9) with KOH pellets, liberating an oily residue. This residue was extracted into dichloromethane and dried over magnesium sulfate. Purification by chromatography through silica gel, eluting with (0.5% conc. ammonia: 4.5% methanol: 95% dichloromethane) yielded the title compound as a dark yellow oil (0.44 g, 88%).

$^1$H NMR (250 MHz, CDCl$_3$) δ: 2.63 (2H, t, J=7 Hz), 3.67 (2H, brs), 3.73 (2H, m, J=7, 2 Hz), 6.62 (1H, d, J=2 Hz), 6.70 (1H, dd, J=8, 2 Hz), 6.95 (1H, d, J=8 Hz), 8.24 (1H, s).

DESCRIPTION 29

7-Amino-2-methyl-3,4-dihydroisoquinolinium Iodide

7-Amino-3,4-dihydroisoquinoline (0.40 g, 2.74 mmol) in acetone (125 ml) was treated with iodomethane (0.50 ml, 8.03 mmol) and left stirring at room temperature for 18 h. The resultant yellow precipitate was collected by filtration and dried in vacuo (0.73 g, 92%).

$^m/_z$ (API$^+$): 161 (M)$^+$

DESCRIPTION 30

(±) 7-Amino-1,2-dimethyl-tetrahydroisoquinoline (±) 7-Amino-2-methyl-3,4-dihydroisoquinolinium iodide (0.50 g, 1.7 mmol) was suspended in anhydrous tetrahydrofuran (50 ml) and cooled to −78° C. The cooled solution was treated with methyl magnesium chloride (2.14 ml of a 3M solution in THF, 6.96 mmol), added as a single portion. The reaction was allowed to reach 25° C. over 18 h before being poured into water (50 ml). The organic solvent was removed in vacuo and the organic product extracted into dichloromethane. Drying over magnesium sulfate and evaporation in vacuo furnished the title compound as a pale yellow oil (0.3 g, 98%). For ease of handling the product was converted into a monohydrochloride.

$^1$H NMR (250 MHz, CDCl$_3$) δ: 1.37 (3H, d, J=7 Hz), 2.46 (3H, s), 2.54–2.83 (3H, m), 3.00 (1H, m), 3.50 (3H, m), 6.45 (1H, d, J=2 Hz), 6.51 (1H, dd, J=8, 2 Hz), 6.88 (1H, d, J=8 Hz).

DESCRIPTION 31

(±) 1-Allyl-7-amino-2-methyl-1,2,3,4-tetrahydroisoquinoline

Prepared in a similar manner to that of Description 30 using allyl magnesium chloride (2M soln. in tetrahydrofuran) and isolated in 27% yield.

$^1$H NMR (CDCl$_3$) δ: 2.48 (3H, s), 2.52–2.83 (5H, m), 3.15 (1H, m), 3.54 (1H, t, J=6 Hz), 3.87 (2H, brs), 5.06 (2H, m), 5.72–5.88 (1H, m), 6.44 (1H, d, J=2 Hz), 6.50 (1H, d, J=2 Hz), 6.88 (1H, d, J=8 Hz).

DESCRIPTION 32

(±) 7-Amino-2-methyl-1-iso-propenyl-1,2,3,4-tetrahydroisoquinoline

Prepared in a similar manner to that of Description 30 using iso-propenyl magnesium bromide (0.5M soln) and isolated in 95% yield.

$^1$H NMR (CDCl$_3$) δ: 1.52 (3H, s), 2.31 (3H, s), 2.50 (2H, m), 2.78–3.14 (2H, m), 3.48 (2H, brs), 3.58 (1H, brs), 5.06 (2H, d, J=1 Hz), 6.51 (2H, m), 6.89 (1H, m).

DESCRIPTION 33

(±) 7-Amino-2-methyl-1-phenyl-1,2,3,4-tetrahydroisoquinoline

Prepared in a similar manner to that of Description 30 using phenyl magnesium bromide (3M solution) in 75% yield.

$^1$H NMR (CDCl$_3$) δ: 2.21 (3H, s), 2.65 (2H, m), 3.13 (2H, m), 3.41 (2H, brs), 4.18 (1H, s), 5.95 (1H, d, J=2 Hz), 6.49 (1H, dd, J=8, 2 Hz), 6.67 (1H, dd, J=9, 1 Hz), 6.92 (1H, d, J=8 Hz), 7.18–7.33 (4H, m).

DESCRIPTION 34

(±) 7-Amino-1-benzyl-2-methyl-1,2,3,4-tetrahydroisoquinoline

Prepared in a similar manner to that of Description 30 using benzyl magnesium chloride (1M solution) in 70% yield.

$^1$H NMR (CDCl$_3$) δ: 2.51 (3H, s), 2.57 (1H, m), 2.80 (3H, m), 3.18 (2H, m), 3.41 (2H, brs), 3.70 (1H, t, J=6 Hz), 6.03 (1H, d, J=2 Hz), 6.47 (1H, dd, J=8, 2 Hz), 6.86 (1H, d, J=8 Hz), 7.12–7.54 (5H, m).

DESCRIPTION 35

(±) 7-Amino-1-iso-butyl-2-methyl-1,2,3,4-tetrahydroisoquinoline

Prepared in a manner similar to that of Description 30 using iso-butyl magnesium bromide (2M) and isolated in 53% yield.

$^1$H NMR (CDCl$_3$) δ: 0.97 (6H, t, J=7 Hz), 1.42 (1H, m), 1.84 (2H, m), 2.50 (3H, s), 2.53 (1H, m), 2.77–2.96 (2H, m), 3.30 (1H, m), 3.53 (1H, brt, J=7 Hz), 3.56 (2H, brs), 6.38 (1H, d, J=2 Hz), 6.53 (1H, dd, J=8, 2 Hz), 6.88 (1H, d, J=8 Hz).

DESCRIPTION 36

7-Nitro-2,3,3-trimethyl-3,4-dihydroisoquinolinium Iodide

7-Nitro-3,3-dimethyl-3,4-dihydroisoquinoline (1.0 g, 4.9 mmol) in acetone (100 ml) was treated with iodomethane (1 ml, 16 mmol). The mixture was stirred at 25° C. for 18 h and the resultant precipitate collected by filtration and dried; pale yellow powder (1.5 g, 88%).

$m/_z$ (API$^+$): 219 (M)$^+$.

DESCRIPTION 37

7-Nitro-2,3,3-trimethyl-1,2,3,4-tetrahydroisoquinoline

D36 (200 mg, 5.8 mmol) was reduced with sodium borohydride (300 mg); 7.9 mmol) in a manner similar to that of Description 5. Purification by chromatography eluting with a dichloromethane solution of ammonia in methanol (0.5% conc. NH$_3$: 4.5% MeOH: 95% CH$_2$Cl$_2$) gave the title compound as a pale yellow oil (93 mg, 73%).

$^1$H NMR (CDCl$_3$) δ: 1.10 (6H, s), 2.40 (3H, s), 2.78 (2H, s), 3.80 (2H, s), 7.21 (1H, d, J=8 Hz), 7.90 (2H, m).

DESCRIPTION 38

7-Amino-2,3,3,-trimethyl-1,2,3,4-tetrahydroisoquinoline

The title compound was prepared from D37 using a method similar to that of Description 2. For ease of handling the compound was converted into a monohydrochloride.

$^1$H NMR (CDCl$_3$) δ: 1.07 (6H, s), 2.35 (3H, s), 2.59 (2H, s), 3.46 (2H, brs), 3.64 (2H, s), 6.37 (1H, d, J=2 Hz), 6.50 (1H, dd, J=8, 2 Hz), 6.84 (1H, d, J=8 Hz).

DESCRIPTION 39

4,4-Spirocyclobutyl-3,4-dihydroisoquinoline

The title compound was prepared in a manner to that of T. J. N. Watson, *J. Org. Chem.*, 1998, 63, 406–407, using 1,3-dibromopropane.

$^1$H NMR (CDCl$_3$) δ: 1.90–2.27 (6H, m), 3.87 (2H, d, J=2 Hz), 7.27 (2H, m), 7.41–7.57 (2H, m), 8.32 (1H, d, J=2 Hz).

DESCRIPTION 40

7-Amino-4,4-spirocyclobutyl-2-methyl-1,2,3,4-tetrahydroisoquinoline

The title compound was prepared from D39 in a manner similar to that described for Descriptions 4, 5, 22 and 2.

$^1$H NMR (CDCl$_3$) δ: 2.01 (4H, m), 2.21–2.36 (2H, m), 2.45 (3H, s), 2.69 (2H, s), 3.45 (2H, s), 6.31 (1H, d, J=2 Hz), 6.62 (1H, dd, J=8, 2 Hz), 7.38 (1H, d, J=8 Hz).

DESCRIPTION 41

4,4-Dimethyl-7-nitro-3,4-dihydroisoquinoline

The title compound was prepared in a manner to that descibed in Descriptions 28 and 29.

$m/_z$ (API$^+$): 205 (MH$^+$; 100%).

DESCRIPTION 42

2,4,4-Trimethyl-7-nitro-3,4-dihydroisoquinolinium Iodide

The title compound was prepared in a manner to that descibed in Description 36.

$m/_z$ (API$^+$): 219 (MH$^+$: 100%).

DESCRIPTION 42

7-Nitro-1,2,4,4-tetramethyl-1,2,3,4-tetrahydroisoquinoline

D41 (1.5 g, 4.3 mmol) in THF (50 ml) was stirred under argon and dimethyl zinc in toluene (3.3 ml, 2M solution) added with rapid stirring at 0° C. The mixture was allowed to warm to room temperature over 1 h, quenched with satd. ammonium chloride and concentrated in vacuo. Work-up with dichloromethane gave the title compound (0.9 g, 90%).

$m/_z$ (API$^+$): 235 (MH$^+$; 100%).

DESCRIPTION 43

7-Amino-1,2,4,4-tetramethyl-1,2,3,4-tetrahydroisoquinoline

Prepared from D42 in a manner similar to that of Description 2.

$^1$H NMR (CDCl$_3$) δ: 1.34 (3H, s), 1.35 (3H, s), 1.49 (3H, d, J=7 Hz), 2.55–2.66 (1H, m), 2.62 (3H, brs), 2.89 (1H, m), 3.50 (2H, brs), 3.77–3.90 (1H, m), 6.47 (1H, d, J=2 Hz), 6.59 (1H, dd, J=8, 2 Hz), 7.11 (1H, d, J=8 Hz).

DESCRIPTION 44

7-Amino-8-chloro-2,3,3,-trimethyl-1,2,3,4-tetrahydroisoquinoline

Chlorination of D38 (900 mg; 4.74 mmol) with N-chloromorpholine (600 mg; 4.90 mmol) in glacial acetic acid (30 ml) for 30 min at 25° C. followed by basic work-up with dichloromethane gave the title compound (700 mg).

$^1$H NMR (CDCl$_3$) δ: 1.06 (6H, s), 2.40 (3H, s), 2.60 (2H, s), 3.67 (2H, s), 3.92, (2H, brs), 6.62 (1H, d, J=8 Hz), 6.79 (1H, d, J=8 Hz); $^m/_z$ (API$^+$): 225.1 (MH$^+$; 100% expected isotope pattern).

DESCRIPTION 45

7-Amino-8-bromo-2,3,3,-trimethyl-1,2,3,4-tetrahydroisoquinoline

Bromination of D38 (282 mg; 1.24 mmol) and K$_2$CO$_3$ (170 mg, 1.24 mmol) with N-bromosuccinimide (240 mg; 1.34 mmol) in acetonitrile (8 ml) for 30 min at 25° C. followed by basic work-up with dichloromethane gave the title compound (80 mg).

$^1$H NMR (CDCl$_3$) δ: 1.07 (6H, s), 2.40 (3H, s), 2.63 (2H, s), 3.64 (2H, s), 4.00, (2H, brs), 6.63 (1H, d, J=8 Hz), 6.82 (1H, d, J=8 Hz).

DESCRIPTION 46

7-Amino-4,4-dimethyl-2-trifluoroacetyl-1,2,3,4-tetrahydroisoquinoline

Prepared from 4-nitrophenyldimethylacetonitrile using procedures outlined above.

$^m/_z$ (API$^+$): 273 (MH$^+$, 90%; C$_{13}$H$_{15}$F$_3$N$_2$O requires M$^+$ 272).

DESCRIPTION 47

7-Amino-8-chloro-4,4-dimethyl-2-trifluoroacetyl-1,2,3,4-tetrahydroisoquinoline The title compound was prepared from D46 in a manner similar to that of Description 44

$^1$H NMR (CDCl$_3$) δ: 1.27 (6H, s), 3.50, 3.63 (2H, 2s, rotamers), 4.05, (2H, brs), 4.76 (2H, s), 6.73 (1H, m), 7.07 (1H, m).

DESCRIPTION 48

7-Amino-8-bromo-4,4-dimethyl-2-trifluoroacetyl-1,2,3,4-tetrahydroisoquinoline The title compound was prepared from D46 in a manner similar to that of Description 45

$^m/_z$ (API$^+$): 351, 353 (MH$^+$, 90%; C$_{13}$H$_{14}$BrF$_3$N$_2$O requires M$^+$ 351).

DESCRIPTION 49

7-Amino-8-ethyl-4,4-dimethyl-2-trifluoroacetyl-1,2,3,4-tetrahydroisoquinoline The title compound was prepared from D48 and tetraethyl tin in a manner similar to that of Description 21.

$^m/_z$ (API$^+$): 301 (MH$^+$, 100%; C$_{15}$H$_{19}$F$_3$N$_2$O requires M$^+$ 300).

DESCRIPTION 50

7-Amino-4,4,8-trimethyl-2-trifluoroacetyl-1,2,3,4-tetrahydroisoquinoline

The title compound was prepared from D48 and tetramethyl tin in a manner similar to that of Description 21.

$^m/_z$ (API$^+$): 287 (MH$^+$, 80%; C$_{14}$H$_{17}$F$_3$N$_2$O requires M$^+$ 286).

DESCRIPTION 51

7-Amino-4,4-dimethyl-2-(2-methoxyethyl)-1,2,3,4-tetrahydroisoquinoline

Prepared using a method similar to that of Descriptions 1–3.

$^m/_z$ (API$^+$): 235 (MH$^+$, 90%; C$_{14}$H$_{23}$N$_2$O requires M$^+$ 234).

PREPARATION 1

Methyl 3-Chloro-4-iso-propoxybenzoate

Methyl 3-chloro-4-hydroxybenzoate (5 g, 26.8 mmol) in DMF (45 ml) was treated with potassium carbonate (7.41 g, 53.6 mmol), 2-iodopropane (3.85 ml, 40.2 mmol) and then stirred at 25° C. for 18 h. Work-up with ethyl acetate gave the title compound (6.1 g).

PREPARATION 2

3-Chloro-4-iso-propoxybenzoic Acid

Methyl 3-chloro-4-iso-propoxybenzoate (5.5 g, 24. 1 mmol) was hydrolysed using 1M NaOH (36 ml) in methanol (80 ml). Extraction and work-up with ethyl acetate rave the title compound (4.3 g).

$^1$H NMR (DMSO-D$_6$) δ: 1.33 (6H, d), 4.79 (1H, m), 7.24 (1H, d), 7.87 (2H, m).

PREPARATION 3

3-Bromo-4-ethoxybenzoic Acid

The title compound was prepared from 4-ethylbenzoic acid in a manner similar to that of Procedure 1.

$^1$H NMR (DMSO-D$_6$) δ: 1.45 (3H, t, J=7 Hz), 4.26 (2H, q, J=7 Hz), 7.26 (1H, d, J=9 Hz), 7.98 (1H, dd, J=2, 9 Hz), 8.12 (1H, d, J=2 Hz).

PREPARATION 4

3-Bromo-4-ethylbenzoic Acid

The title compound was prepared from 4-ethylbenzoic acid in a manner similar to that of Procedure 1.

$^1$H NMR (DMSO-D$_6$) δ: 1.20 (3H, t, J=7 Hz), 2.78 (2H, q, J=7 Hz), 7.50 (1H, d, J=8 Hz), 7.90 (1H, dd, J=2, 8 Hz), 8.07 (1H, d, J=8 Hz).

PREPARATION 5

3-Cyano-4-iso-propylbenzoic Acid

The title compound was prepared from 4-iso-propylbenzoic acid using a manner similar to that described in Procedures 1 and 5.

$^1$H NMR (DMSO-D$_6$) δ: 1.07 (6H, d, J=7 Hz), 3.13 (1H, m, overlapped), 7.48 (1H, d, J=7 Hz), 7.96 (1H, dd, J=2, 8 Hz)), 8.00 (1H, d, J=2 Hz).

PREPARATION 6

4-Methoxy-3-trifluoromethylbenzoic Acid

The title compound was prepared from 3-bromo-4-methoxybenzoic acid and potassium trifluoroacetate in a manner similat to that of Procedures 3 and 4.

$^1$H NMR (DMSO-D$_6$) δ: 3.78 (3H, s), 7.18 (1H, d, J=9 Hz), 7.90 (1H, d, J=2 Hz), 8.00 (1H, dd, J=2, 9 Hz), 12.70–13.10 (1H, br, exchangeable).

PREPARATION 7

4-Methoxy-3-trifluoromethylbenzoyl Chloride

The title compound was prepared from 4-methoxy-3-trifluoromethylbenzoic acid with oxalyl chloride and DMF in chloroform at room temperature [D. Levin, Chem. Br., 1977, 201] followed by evaporation in vacuo.

PREPARATION 8

Methyl 3-Bromo-4-iso-propoxybenzoate

Methyl 3-bromo-4-hydroxybenzoate (2.5 g, 10.8 mmol) in DMF (35 ml) was treated with potassium carbonate (3.0 g, 21.6 mmol), 2-iodopropane (2.76, 21.6 mmol) and then stirred at 25° C. for 48 h. Work-up with ethyl acetate gave the title compound (3.0 g).

$^1$H NMR (250 MHz, CDCl$_3$) δ: 1.41 (6H, d, J=7 Hz), 3.89 (3H, s), 4.66 (1H, m), 6.90 (1H, d, J=8 Hz), 7.93 (1H, dd, J=8, 2 Hz), 8.22 (1H, d, J=2 Hz).

PREPARATION 9

Methyl 3-Cyano-4-iso-propoxybenzoate

Methyl 3-bromo-4-iso-propoxybenzoate (2.0 g, 7.3 mmol) and copper(I)cyanide in N-methyl pyrrolidone (50 ml) was heated under vigorous reflux for 4 h. Work-up with ethyl acetate gave the title compound (1.0 g).

$^1$H NMR (250 MHz, CDCl$_3$) δ: 1.56 (6H, d, J=7 Hz), 4.05 (3H, s), 4.88 (1H, m), 7.13 (1H, d, J=8 Hz), 8.31 (1H, dd, J=8, 2 Hz), 838 (1H, d, J=Hz).

PREPARATION 10

Methyl 3,5 Dichloro-4-ethoxybenzoate

The title compound was prepared in 69% yield from methyl 3,5-dichloro-4-hydroxybenzoic acid and iodoethane in a manner similar to that of Preparation 1.

$^1$H NMR (250 MHz, CDCl$_3$) δ: 1.47 (3H, t, J=7 Hz), 3.91 (3H, s), 4.16 (2H, q, J=7 Hz), 7.96 (2H, s).

PREPARATION 11

3-Methanesulfonyl-4-iso-propylbenzoic Acid

3-Chlorosulfonyl-4-iso-propylbenzoic acid (2.62 g, 10 mmol) [made from 4-iso-propyl benzoic acid in a manner similar to that described in Procedures 7 and 8] was added slowly to a slurry of NaHCO$_3$ (2.52 g, 30 mmol) and Na$_2$SO$_3$ (1.26 g 10 mmol) in water (9 ml) at 75° C. The mixture was stirred for 1 h and then treated with bromoacetic acid (2.08 g, 15 mmol) and NaOH (0.60 g, 15 mmol). The temperateure was raised to 105° C. and the mixture heated at reflux for 24 h. The mixture was cooled, acidified to pH 1 and the resultant precipitate collected, washed and dried to give the title compound (1.43 g. 59%).

$^1$H NMR (250 MHz, acetone-D$_6$) δ: 124 (6H, d, J=7 Hz), 3.13 (3H, s), 3.88 (1H, m), 7.72 (1H, d, J=7 Hz), 8.15 (1H, dd, J=7 Hz), 8.52 (1H, d, J=7 Hz).

PREPARATION 12

3-Chloro-4-ethoxybenzoic Acid $^1$H NMR (DMSO-D$_6$) δ: 1.39 (3H, t, J=7 Hz), 4.20 (2H, q, J=7 Hz), 7.22 (1H, d, J=7 Hz), 7.87 (2H, m).

PREPARATION 13

3,5-Dichloro-4-ethoxybenzoic Acid $^1$H NMR (DMSO-D$_6$) δ: 1.41 (3H, t, J=7 Hz), 4.15 (2H, q, J=7 Hz), 7.92 (2H, s), 13.14 (1H, br).

PREPARATION 14

4-Isopropyl-3-trifluoromethylsulphonyl Benzoic Acid

This acid was prepared using the general method described by Yagupolski et al., Synthesis, 1975, 721, but oxidation of the intermediate sulphide was carried out with potassium permanganate.

$^1$H NMR (250 MHz, CDCl$_3$) δ: 1.34 (6H, d, J=7 Hz), 4.02 (1H, m, J=7 Hz), 7.77 (1H, d, J=8 Hz), 8.44 (1H, dd, J=8, 2 Hz), 8.82 (1H, d, J=2 Hz).

PREPARATION 15

Methyl 3-Acetyl-4-iso-propoxybenzoate

The bromo ester P8 (2.5 g, 8.3 mmol) in dry dioxan (30 ml) was treated with (1-ethoxyvinyl)-tributyl tin (3.58 g, 9.9 mmol) followed by tetrakis triphenylphosphine palladium (o) (0.48 g, 0.4 mmol) and heated at 100° C. for 18 h. After cooling, the mixture was acidified and aqueous work-up and extraction into ethyl acetate gave a coloured oil (5.6 g). Flash chromatography on Kieselgel 60 [hexane to 20% EtAc/hexane gave the title compound as a yellow oil (2.3 g).

PREPARATION 16

3-Acetyl-4-iso-propoxybenzoic Acid

Saponification of the ester P15 (2.3 g) gave the title compound as a white solid (1.3 g).

$^1$H NMR (250 MHz, CDCl$_3$) δ: 148 (6H, d, J=7 Hz), 2.63 (3H, s), 4.80 (1H, m), 7.00 (1H, d, J=8 Hz), 8.17 (1H, dd, J=8, 2 Hz), 846 (1H, d, J=2 Hz).

PREPARATION 17

3-Acetyl-4-ethoxybenzoic Acid

Prepared in a similar manner to that desribed for Preparations 15 and 16.

$^1$H NMR (250 MHz, CDCl$_3$) δ: 1.53 (3H, t, J=7 Hz), 2.65 (3H, s), 4.23 (2H, q, J=7 Hz), 7.01 (1H, d, J=8 Hz), 8.19 (1H, dd, J=8, 2 Hz), 848 (1H, d, J=2 Hz).

PROCEDURE 1

5-Bromo-2,4-dimethoxybenzoic Acid

To a solution of 2,4-dimethoxybenzoic acid (4.0 g, 0.022 mol) in chloroform (60 ml) was added bromine (1.13 ml, 0.022 mol) in chloroform (20 ml) dropwise. After stirring overnight at room temperature the precipitate was filtered off and dried to afford the title compound as a white solid (2.87 g).

PROCEDURE 2

5-Bromo-4-iso-propyl-2-methoxy Benzoic Acid

To a solution of 2-methoxy-4-iso-propyl benzoic acid (7.0 g 36.0 mmol) in chloroform (100 ml) was added bromine (1.86 ml) in chloroform (20 ml) dropwise. The reaction was stirred at room temperature overnight. Evaporation in vacuo afforded an oil (9.27 g).

$^m/_z$ (CI): 275, 273 (MH$^+$; 70%).

PROCEDURE 3

Methyl-5-bromo-4-iso-propyl-2-methoxy Benzoate

5-Bromo-4-iso-propyl-2-methoxybenzoic acid (9.268 g 34.0 mmol) was dissolved in ethanol (250 ml) and conc.

$H_2SO_4$ (2 ml) added. The mixture was refluxed for 5 h and concentrated in vacuo. Residual material was taken up into ethyl acetate and water, and the organic layer, dried ($MgSO_4$). Concentration in vacuo afforded an oil, which was purified by Biotage Column Chromatography on silica gel using 10% ether in hexane to give an oil (5.5 g).

PROCEDURE 4

2,4-Dimethoxy-5-trifluoromethylbenzoic Acid 2,4-Dimethoxy-5-bromobenzoic acid methyl ester (1.5 g; 5.4 mmol) in DMF (25 ml) and toluene (8 ml) under argon was treated with potassium trifluoroacetate (1.53 g; 10.1 mmol) and copper (I) iodide (2.1 g, 10.9 mmol). The mixture was heated to 170° C. with removal of water (Dean/Stark), and then at 155° C. for 18 h. The mixture was allowed to cool, poured into ether/water and filtered through Kieselguhr. The organic layer was dried ($Na_2SO_4$) and concentration in vacuo gave a brown solid. Chromatography on Kieselgel 60 with 1:1ether/petrol gave a white solid (1.03 g) which was hydrolysed in 1:1 MeOH: aq NaOH (50 ml) at 50° C. Work-up gave the title compound as a white solid (1 g).

PROCEDURE 5a

Methyl 2-methoxy-5-cyano-4-iso-propylbenzoate

Copper (I) cyanide (550 mg, 6 mmol) was added to a solution of methyl 2-methoxy-5-bromo-4-iso-propylbenzoate (861 mg) in N-methyl-2-pyrolidinone (30 ml). The mixture was stirred under argon and boiled under reflux for 4 h. The mixture was cooled, poured into excess ice/water and ethyl acetate and filtered. The organic phase was separated, washed with water, brine and dried ($MgSO_4$). Evaporation gave a crude brown solid which was purified by chromatography on silica gel eluting with ethyl acetate/n-hexane (1:4). The product was obtained as a white solid (523 mg).

$^1$H NMR (250 MHz, $CDCl_3$) δ: 1.33 (6H, d, J=7 Hz), 3.38 (1H, sep, J=7 Hz), 3.89 (3H, s), 3.98 (3H, s), 6.91 (1H, s), 8.08 (1H, s); $^m/_z$ ($API^+$): 234 (MH+, 30%).

PROCEDURE 5b

2-Methoxy-5-cyano-4-iso-propylbenzoic Acid

2N NaOH (1.25 ml) was added to a solution of the methyl ester P5a (490 mg) in methanol (10 ml). The solution was stirred overnight at room temperature. The solution was then diluted with water, concentrated in vacuo and washed with ethyl acetate. The aqueous phase was then acidified with 2N HCl and extracted with ethyl acetate. The extract was washed with brine. dried ($MgSO_4$) and evaporated to dryness giving the product as a white solid (418 mg).

$^1$H NMR (250 MHz, $CDCl_3$) δ: 1.35 (6H, d, J=7 Hz), 3.43 (1H, sep, J=7 Hz), 4.14 (3H, s), 7.00 (1H, s), 8.41 (1H, s); $^m/_z$ ($API^+$): 220 (MH+, 100%).

PROCEDURE 6a

Ethyl 2-ethoxy-4-iso-propyl-5-cyanobenzoate

Ethyl 2-ethoxy-4-iso-propyl-5-bromobenzoate (12 g, 3.8 mmol) was treated with copper (I) cyanide (682 mg, 7.6 mmol) in N-methyl-2-pyrrolidinone (40 ml) as described in Procedure 5 to give the title compound as an oil (400 mg).

$^1$H NMR (250 MHz, $CDCl_3$) δ: 1.12 (6H, d, J=7 Hz), 1.30 (3H, t, J=7 Hz), 1.84 (3H, t, J=7 Hz), 3.17 (1H, sep, J=7 Hz), 3.99 (2H, q, J=9 Hz), 4.16 (2H, q, J=7 Hz), 6.69 (1H, s), 7.86 (1H, s); $^m/_z$ ($API^+$): 262 (MH+, 100%).

PROCEDURE 6b

2-Ethoxy-4-iso-propyl-5-cyanobenzoic Acid

The ester P6a (370 mg, 1.41 mmol) was dissolved in methanol (5 ml) and over a 24 h period 1N NaOH (2.1 ml, 2.1 mmol) was added. The solution was concentrated under vacuum, diluted with water and washed with ethyl acetate. The aqueous phase was acidified with 2N HCl and extracted with ethyl acetate. The extract was washed with brine, dried ($MgSO_4$) and evaporated to give the title acid (306 mg).

$^1$H NMR (250 MHz $CDCl_3$) δ: 1.39 (3H, d, J=7 Hz), 1.66 (3H, t, J=7 Hz), 3.47 (1H, sep, J=7 Hz), 4.46 (2H, q, J=7 Hz), 7.03 (1H, s), 8.47 (1H, s); $^m/_z$ ($API^+$): 234 (MH+, 100%).

PROCEDURE 7

4-Ethoxy-2-methoxy-5-methylsulfonylbenzoic Acid

4-Ethoxy-2-methoxy-5-chlorosulfonyl benzoic acid in a 49% yield. was prepared in 49% yield using the procedure of M. W. Harrold et al., J. Med. Chem., 1989, 32 874. This was used according to the method of R. W. Brown, J. Org. Chem., 1991, 56, 4974, to the title compound in 19% yield.

$^1$H NMR (DMSO-$D_6$) δ: 1.30 (3H, t), 3.10 (3H, s), 3.83 (3H, s), 4.24 (2H, q). 6.73 (1H, s), 8.07 (1H, s).

PROCEDURE 8

4-iso-Propyl-2-methoxy-5-methylsulfonylbenzoic Acid

This was prepared in a similar manner to the procedure of C. Hansch, B. Schmidhalter, F. Reiter, W. Saltonstall. J. Org. Chem., 1956, 21, 265 to afford the intermediate 5-chlorosulfonyl-4-isopropyl-2-methoxybenzoic acid which was converted into the title compound using the method of Procedure 7.

$^1$H NMR (DMSO-$D_6$) δ: 1.30 (6H, d), 3.21 (3H, s), 3.80 (1H, m), 3.94 (3H, s), 7.26 (1H, s), 8.19 (1H, s).

EXAMPLE 1

N-(3,3-Dimethyl-1,2,3,4-tetrahydro-2-trifluoroacetyl-isoquinolin-7-yl)-4-methoxy-3-trifluoromethylbenzamide A solution of 7-amino-3,3-dimethyl-1,2,3,4-tetrahydro-2-trifluoroacetylisoquinoline (408 mg; 1.5 mmol) in dichloromethane (20 ml) and triethylamine (0.6 ml) was treated with 4-methoxy-3-trifluoromethylbenzoyl chloride (358 mg; 1.5 mmol). The resultant solution was stirred at 25° C. for 1 h. The reaction mixture was then washed with water, dried over sodium sulfate and evaporated in vacuo. The residue was purified by column chromatography on silica, eluting with 1% methanol in dichloromethane, to give the title compound (442 mg).

$^1$H NMR ($CDCl_3$) δ: 1.48 (6H, s), 2.84 (2H, s), 3.99 (3H, s), 4.51 (2H, s), 7.11 (1H, d, J=9 Hz), 7.23 (1H, d, J=8 Hz), 7.50 (1H, dd, J=8, 2 Hz), 7.65 (1H, d, J=2 Hz), 7.93 (1H, s), 8.08–8.11 (2H, m); $^m/_z$ ($API^+$): 475 (M+H)+.

The following Examples were prepared using methods similar to those described in Example 1 and the foregoing Descriptions, Preparations and Procedures.

EXAMPLE 2

N-(3,3-Dimethyl-1,2,3,4-tetrahydro-2-trifluoroacetyl-isoquinolin-7-yl)-3-cyano-4-iso-propylbenzamide $^1$H NMR ($CDCl_3$) δ: 1.36 (6H, d, J=7 Hz), 1.50 (6H, s), 2.85 (2H, s), 3.46 (1H, m), 4.52 (2H, s), 7.25 (1H, d, J=8

Hz), 7.51 (1H, dd, J=8, 2 Hz), 7.56 (1H, d, J=8 Hz), 7.67 (1H, d, J=Hz), 7.95 (1H, s), 8.08 (1H, dd, J=8, 2), 8.13 (1H, d, J=2 Hz); $^m/_z$ (API$^+$): 444 (M+H)$^+$.

EXAMPLE 3

N-(3,3-Dimethyl-1,2,3,4-tetrahydro-2-trifluoroacetylisoquinolin-7-yl)-3-chloro-4-iso-propyloxybenzamide $^1$H NMR (CDCl$_3$) δ: 1.42 (6H, d, J=6 Hz), 1.48 (6H, s), 2.83 (2H, s), 4.49 (2H, s), 4.67 (1H, m, J=6 Hz), 6.99 (1H, d, J=9 Hz), 7.21 (1H, d, J=8 Hz), 7.47 (1H, dd, J=8, 2 Hz), 7.64 (1H, d, J=2 Hz), 7.75 (1H, dd, J=9, 2 Hz), 7.83 (1H, s), 7.88 (1H, d, J=2 Hz); $^m/_z$ (API$^+$): 469, 471 (M+H)$^+$.

EXAMPLE 4

N-(3,3-Dimethyl-1,2,3,4-tetrahydro-2-trifluoroacetylisoquinolin-7-yl)-3-bromo-4-ethoxybenzamide $^1$H NMR (CDCl$_3$) δ: 1.47 (6H, s), 1.51 (3H, t, J=7 Hz), 2.82 (2H, s), 4.16 (2H, q, J=7 Hz), 4.47 (2H, s), 6.91 (1H, d, J=9 Hz), 7.19 (1H, d, J=8 Hz), 7.48 (1H, dd, J=8, 2 Hz), 7.62 (1H, d, J=2 Hz), 7.80 (1H, dd, J=9, 2 Hz), 8.01 (1H, s), 8.05 (1H, d, J=2 Hz); $^m/_z$ (API$^+$): 499, 501 (M+H)$^+$.

EXAMPLE 5

N-(3,3-Dimethyl-1,2,3,4-tetrahydro-2-trifluoroacetylisoquinolin-7-yl)-3-bromo-4-iso-propyloxybenzamide $^1$H NMR (CDCl$_3$) δ: 1.42 (6H, d, J=6 Hz), 1.48 (6H, s), 2.83 (2H, s), 4.50 (2H, s), 4.67 (1H, m, J=6 Hz), 6.96 (1H, d, J=9 Hz), 7.22 (1H, d, J=8 Hz), 7.48 (1H, dd, J=8, 2 Hz), 7.65 (1H, d, J=2 Hz), 7.82 (2H, m), 8.06 (1H, d, J=2 Hz); $^m/_z$ (API$^+$): 513, 515 (M+H)$^+$.

EXAMPLE 6

N-(3,3-Dimethyl-1,2,3,4-tetrahydroisoquinolin-7-yl)-4-methoxy-3-trifluoromethylbenzamide To a stirred solution of N-(3,3-dimethyl-1,2,3,4-tetrahydro-2-trifluoroacetylisoquinolin-7-yl)-4-methoxy-3-trifluoromethyl benzamide (442 mg; 0.93 mmol) in methanol (50 ml) and water (25 ml) was added potassium carbonate (642 mg; 4.65 mmol) and the resultant mixture heated under reflux for I h. Evaporation in vacuo gave a residue which was partitioned between dichloromethane and water. The organic phase was dried over sodium sulfate, and evaporation in vacuo gave the title compound (303 mg).

$^1$H NMR (CDCl$_3$) δ: 1.19 (6H, s), 1.53 (1H, s, ex. D$_2$O), 2.61 (2H, s), 3.98 (3H, s), 4.06 (2H, s), 7.07 (2H, m), 7.30 (1H, dd, J=8, 2 Hz), 7.42 (1H, s), 7.68 (1H, s), 8.05 (2H, m); $^m/_z$ (API$^+$): 379 (M+H)$^+$.

EXAMPLE 7

N-(3,3-Dimethyl-1,2,3,4-tetrahydroisoquinolin-7-yl)-3-cyano-4-iso-propylbenzamide Prepared from Example 2 in 78% yield, as described in Example 6.

$^1$H NMR (CDCl$_3$): δ 1.19 (6H, s), 1.35 (6H, d, J=7 Hz), 1.56 (1H, s, ex. D$_2$O), 2.62 (2H, s), 3.44 (1H, m, J=7 Hz), 4.06 (2H, s), 7.08 (1H, d, J=8 Hz), 7.28 (1H, dd, J=8, 2 Hz), 7.42 (1H, s), 7.52 (1H, d, J=8 Hz), 7.76 (1H, s), 8.04 (1H, dd, J=8, 2 Hz), 8.09 (1H, d, J=2 Hz); $^m/_z$ (API$^+$): 348 (M+H)$^+$.

EXAMPLE 8

N-(3,3-Dimethyl-1,2,3,4-tetrahydroisoquinolin-7-yl)-3-chloro-4-iso-propyloxy-benzamide Prepared from Example 3 in 94% yield, as described in Example 6.

$^1$H NMR (CDCl$_3$) δ: 1.18 (6H, s), 1.42 (6H, d, J=6 Hz), 1.56 (1H, s, ex. D$_2$O), 2.61 (2H, s), 4.05 (2H, s), 4.67 (1H, m, J=6 Hz), 6.99 (1H, d, J=9 Hz), 7.04 (1H, d, =8 Hz), 7.28 (1H, dd, obscured by CHCl$_3$, J=2 Hz), 7.42 (1H, d, J=2 Hz), 7.65 (1H, s), 7.74 (1H, dd, J=9, 2 Hz), 7.87 (1H, d, J=2 Hz); $^m/_z$ (API$^+$): 373, 375 (M+H)$^+$.

EXAMPLE 9

N-(3,3-Dimethyl-1,2,3,4-tetrahydroisoquinolin-7-yl)-3-bromo-4-ethoxybenzamide

Prepared from Example 4 92% yield, as described in Example 6.

$^1$H NMR (CDCl$_3$) δ: 1.18 (6H, s), 1.51 (3H, t, J=7 Hz), 1.56 (1H, s, ex. D$_2$O), 2.61 (2H, s), 4.05 (2H, s), 4.17 (2H, q, J=7 Hz), 6.94 (1H, d, J=9 Hz), 7.04 (1H, d, J=8 Hz), 7.29 (1H, dd, obscurred by CHCl$_3$, J=8, 2 Hz), 7.47 (1H, s), 7.65 (1H, s), 7.80 (1H, dd, J=9, 2 Hz), 8.04 (1H, d, J=2 Hz); $^m/_z$ (API$^+$): 403, 405 (M+H)$^+$.

EXAMPLE 10

N-(3,3-Dimethyl-1,2,3,4-tetrahydroisoquinolin-7-yl)-3-bromo-4-iso-propyloxybenzamide Prepared from Example 5 in 74% yield, as described in Example 6.

$^1$H NMR (CDCl;) δ: 1.19 (6H, s), 1.42 (6H, d, J=6 Hz), 1.63 (1H, s, ex. D$_2$O), 2.61 (2H, s), 4.05 (2H, s), 4.67 (1H, m, J=6 Hz), 6.96 (1H, d, J=9 Hz), 7.04 (1H, d, J=8 Hz), 7.29 (1H, obscured by CHCl$_3$), 7.42 (1H, s), 7.67 (1H, s), 7.79 (1H, dd, J=9, 2 Hz), 8.04 (1H, d, J=2 Hz); $^m/_z$ (API$^+$): 417, 419 (M+H)$^+$.

EXAMPLE 11

N-(2,4,4-Trimethyl-1,2,3,4-tetrahydroisoquinolin-7-yl)-3-cyano-4-iso-propyloxybenzamide $^1$H NMR (CDCl$_3$) δ: 1.30 (6H, s), 1.44 (6H, d, J=7 Hz), 2.39 (2H, s), 2.41 (3H, s), 3.53 (2H, s), 4.75 (1H, m), 7.05 (1H, d), 7.32 (3H, m), 7.70 (1H, s), 8.06 (2H, m); $^m/_z$ (API$^+$): 378.3 (MH$^+$; 100%).

EXAMPLE 12

N-(2,4,4-Trimethyl-1,2,3,4-tetrahydroisoquinolin-7-yl)-3-bromo-4-iso-propyloxybenzamide $^1$H NMR (CDCl$_3$) δ: 1.30 (6H, s), 1.42 (6H, d, J=7 Hz), 2.39 (2H, s), 2.42 (3H, s), 3.54 (2H, s), 4.67 (1H, m), 6.95 (1H, d), 7.34 (3H, m), 7.60 (1H, s), 7.78 (1H, dd), 8.04 (1H, d); $^m/_z$ (API$^+$): 431.2 (MH$^+$; 100%).

EXAMPLE 13

N-(2,4,4-Trimethyl-1,2,3,4-tetrahydroisoquinolin-7-yl)-5-bromo-4-ethoxy-2-methoxybenzamide $^1$H NMR (CDCl$_3$) δ: 1.30 (6H, s), 1.52 (3H, t, J=7 Hz), 2.39 (2H, s), 2.41 (3H, s), 3.54 (2H, s), 4.04 (3H, s), 4.16 (2H, q, J=7 Hz), 6.49 (1H, s), 7.34 (3H, m), 8.44 (1H, s), 9.51 (1H, s); $^m/_z$ (API$^+$): 447.2 (M$^+$; 98%).

EXAMPLE 14

N-(2,4,4-Trimethyl-1,2,3,4-tetrahydroisoquinolin-7-yl)-3-acetyl-4-iso-propyloxybenzamide $^1$H NMR (CDCl$_3$) δ: 1.30 (6H, s), 1.44 (6H, d), 2.39 (2H, s), 2.41 (3H, s), 2.63 (3H, s), 3.52 (2H, s), 4.79 (1H, m), 7.03 (1H, d), 7.28 (1H, d), 7.39 (2H, m), 8.06 (1H, s), 8.11 (1H, dd), 8.18 (1H, d); $^m/_z$ (API$^+$): 395.3 (MH$^+$; 100%).

EXAMPLE 15

N-(2,4,4-Trimethyl-1,2,3,4-tetrahydroisoquinolin-7-yl)-3-bromo-4-methoxybenzamide $^1$H NMR (CDCl$_3$) δ: 1.30 (6H, s), 2.39 (2H, s), 2.41 (3H, s), 3.53 (2H, s), 3.97 (3H, s), 6.96 (1H, d), 7.33 (3H, m), 7.63 (1H, s), 7.83 (1H, dd), 8.05 (1H, d); $^m/_z$ (API$^+$): 404, 402 (M$^+$; 98%).

EXAMPLE 16

N-(2,4,4-Trimethyl-1,2,3,4-tetrahydroisoquinolin-7-yl)-3-chloro-4-methoxybenzamide $^1$H NMR (CDCl$_3$) δ: 1.30 (6H, s), 2.39 (2H, s), 2.41 (3H, s), 3.53 (2H, s), 3.97 (3H, s) 7.00 (1H, d), 7.34 (3H, m); 7.62 (1H, s), 7.77 (1H, dd), 7.88 (1H, d); $^m/_z$ (API$^+$): 359.2 (MH$^+$; 100%).

EXAMPLE 17

N-(2,4,4-Trimethyl-1,2,3,4-tetrahydroisoquinolin-7-yl)-3-iodo-4-methoxybenzamide $^1$H NMR (CDCl$_3$) δ: 1.30 (6H, s), 2.41 (2H, s), 2.42 (3H, s), 3.55 (2H, s), 3.95 (3H, s), 6.87 (1H, d), 7.34 (3H, m), 7.62 (1H, s), 7.86 (1H, dd), 8.26 (1H, d). $^m/_z$ (API$^+$): 451.1 (MH$^+$; 100%).

EXAMPLE 18

N-(2,4,4-Trimethyl-1,2,3,4-tetrahydroisoquinolin-7-yl)-3-fluoro-4-methoxybenzamide $^1$H NMR (CDCl$_3$) δ: 1.30 (6H, s), 2.39 (2H, s), 2.41 (3H, s), 3.53 (2H, s), 3.96 (3H, s), 7.02 (1H, t), 7.34 (3H, m), 7.63 (3H, m); $^m/_z$ (API$^+$): 343.2 (MH$^+$; 100%).

EXAMPLE 19

N-(2,4,4-Trimethyl-1,2,3,4-tetrahydroisoquinolin-7-yl)-3-cyano-4-methoxybenzamide $^1$H NMR (CDCl$_3$) δ: 1.30 (6H, s), 2.40 (2H, s), 2.42 (3H, s), 3.54 (2H, s), 4.01 (3H, s), 7.07 (1H, d), 7.33 (3H, m), 7.73 (1H, s), 8.09 (2H, m); $^m/_z$ (API$^+$): 350.2 (MH$^+$; 100%).

EXAMPLE 20

N-(2,4,4-Trimethyl-1,2,3,4-tetrahydroisoquinolin-7-yl)-4-methoxy-3-pentafluoroethylbenzamide $^1$H NMR (CDCl$_3$) δ: 1.30 (6H, s), 2.40 (2H, s), 2.42 (3H, s), 3.54 (2H, s), 3.95 (3H, s), 7.10 (1H, d), 7.35 (3H, m), 7.65 (1H, s), 8.01 (1H, d), 8.06 (1H, dd); $^m/_z$ (API): 443.2 (MH$^+$; 100%).

EXAMPLE 21

N-(2,4,4-Trimethyl-1,2,3,4-tetrahydroisoquinolin-7-yl)-3-chloro-4-ethoxybenzamide $^1$H NMR (CDCl$_3$) δ: 1.30 (6H, s), 1.51 (3H, t), 2.39 (2H, s), 2.41 (3H, s), 3.53 (2H, s), 4.18 (2H, q), 6.97 (1H, d), 7.34 (3H, m), 7.64 (1H, s), 7.74 (1H, dd), 7.87 (1H, d); $^m/_z$ (API): 373.2 (MH$^+$; 100%).

EXAMPLE 22

N-(2,4,4-Trimethyl-1,2,3,4-tetrahydroisoquinolin-7-yl)-3-cyano-4-ethoxybenzamide $^1$H NMR (CDCl$_3$) δ: 1.30 (6H, s), 1.53 (3H, t), 2.40 (2H, s), 2.41 (3H, s), 3.53 (2H, s), 4.23 (2H, q), 7.04 (1H, d), 7.34 (3H, m), 7.71 (1H, s), 8.07 (2H, m); $^m/_z$ (API$^+$): 364.2 (MH$^+$; 100%)

EXAMPLE 23

N-(2,4,4-Trimethyl-1,2,3,4-tetrahydroisoquinolin-7-yl)-2,4-dimethoxy-5-trifluoromethylbenzamide $^1$H NMR (CDCl$_3$) δ: 1.30 (6H, s), 2.39 (2H, s), 2.41 (3H, s), 3.54 (2H, s), 3.98 (3H, s), 4.12 (3H, s), 6.56 (1H, s), 7.34 (3H, m), 8.54 (1H, s), 9.42 (1H, s); $^m/_z$ (API$^+$): 423.2 (MH$^+$; 100%).

EXAMPLE 24

N-(2,4,4-Trimethyl-1,2,3,4-tetrahydroisoquinolin-7-yl)-3-bromo-4-methylbenzamide $^1$H NMR (CDCl$_3$) δ: 1.30 (6H, s), 2.42 (5H, s), 2.45 (3H, s), 3.54 (2H, s), 7.35 (4H, m), 7.68 (1H, dd), 7.81 (1H, s), 8.01 (1H, d); $^m/_z$ (API$^+$): 388, 386 (M$^+$; 100%).

EXAMPLE 25

N-(2,4,4-Trimethyl-1,2,3,4-tetrahydroisoquinolin-7-yl)-3-cyano-4-ethylbenzamide $^1$H NMR (CDCl$_3$) δ: 1.31 (6H, s), 1.34 (3H, t), 2.40 (2H, s), 2.42 (3H, s), 2.95 (2H, q), 3.54 (2H, s), 7.35 (3H, m), 7.48 (1H, d), 7.69 (1H, s), 8.00 (1H, dd), 8.10 (1H, d); $^m/_z$ (API$^+$): 349.2 (MH$^+$; 100%).

EXAMPLE 26

N-(2,4,4-Trimethyl-1,2,3,4-tetrahydroisoquinolin-7-yl)-3,5-dichloro-4-ethoxybenzamide $^1$H NMR (CDCl$_3$) δ: 1.25 (6H, d), 1.48 (3H, t), 2.39 (5H, m), 3.49 (2H, s), 4.16 (29H, q), 7.32 (3H, m), 7.78 (2H, s), 7.84 (1H, s): $^m/_z$ (API$^+$): 407.1 (M$^+$; 100%).

EXAMPLE 27

N-(2,4,4-Trimethyl-1,2,3,4-tetrahydroisoquinolin-5-yl)-5-bromo-4-ethoxy-2-methoxybenzamide $^1$H NMR (CDCl$_3$) δ: 1.41 (6H, s), 1.54 (3H, t, J=7 Hz), 2.34 (2H, s), 2.39 (3H, s), 3.56 (2H, s), 3.90 (3H, s), 4.18 (2H, q, J=7 Hz), 6.53 (1H, s), 6.90 (1H, d, J=7 Hz), 7.16 (1H, t, J=7 Hz), 7.49 (2H, d, J=7 Hz), 8.51 (1H, s), 9.38 (1H, brs); $^m/_z$ (API$^+$): 447, 449 (MH)$^+$.

EXAMPLE 28

N-(2,4,4-Trimethyl-1,2,3,4-tetrahydroisoquinolin-5-yl)-5-cyano-2-ethoxy-4-iso-propylbenzamide $^1$H NMR (CDCl$_3$) δ: 1.37 (6H, d, J=6 Hz), 1.41 (6H, s), 1.45 (3H, t, J=7 Hz), 2.34 (2H, s), 2.39 (3H, s), 3.43 (1H, m), 3.56 (2H, s), 3.40 (2H, q, J=7 Hz), 6.97 (1H, d, J=7 Hz), 7.00 (1H, s), 7.18 (1H, t, J=7 Hz), 7.31 (1H, d, J=7Hz), 8.61 (1H, s), 9.30 (1H, brs); $^m/_z$ (API$^+$): 406 (MH$^+$).

EXAMPLE 29

N-(2,4,4-Trimethyl-1,2,3,4-tetrahydroisoquinolin-5-yl)-5-chloro-2-methoxy-4-iso-propyloxybenzamide $^1$H NMR (CDCl$_3$) δ: 1.41 (6H, s), 1.44 (6H, d, J=6 Hz), 2.34 (2H, s), 2.40 (3H, s), 3.56 (2H, s), 4.02 (3H, s), 4.64 (1H, m), 6.59 (1H, s), 6.91 (1H, d, J=7 Hz), 7.16 (1H, t, J=7 Hz), 7.49 (1H, d, J=7 Hz), 8.35 (1H, s), 9.39 (1H, brs); $^m/_z$ (API$^+$): 416, 418 (MH)$^+$.

EXAMPLE 30

N-(2,4,4-Trimethyl-1,2,3,4-tetrahydroisoquinolin-5-yl)-5-bromo-2-methoxy-4-iso-propylbenzamide $^1$H NMR (CDCl$_3$) δ: 1.29 (6H, d, J=6 Hz), 1.41 (6H, s), 2.35 (2H, s), 2.40 (3H, s), 3.41 (1H, m), 3.57 (2H, s), 4.05 (3H, s), 6.92 (2H, m), 7.17 (1H, t, J=7 Hz), 7.50 (1H, d, J=7 Hz), 8.49 (1H, s), 9.50 (1H, brs); $^m/_z$ (API$^+$): 445, 447 (MH)$^+$.

EXAMPLE 31

N-(2,4,4-Trimethyl-1,2,3,4-tetrahydroisoquinolin-5-yl)-4-ethoxy-2-methoxy-5-trifluoromethylbenzamide $^1$H NMR (CDCl$_3$) δ: 1.41 (6H. s), 1.48 (3H, t, J=7 Hz), 2.35 (2H. s), 2.41 (3H, s), 3.57 (2H, s), 4.09 (3H, s), 4.22 (2H, q, J=7 Hz), 6.58 (1H, s), 6.90 (1H, d, J=7 Hz), 7.19 (1H, t, J=7 Hz), 7.50 (1H, d, J=7 Hz), 8.60 (1H, s), 9.33 (1H, brs); $^m/_z$ (API$^+$): 437 (MH$^+$).

EXAMPLE 32

N-(2,4,4-Trimethyl-1,2,3,4-tetrahydroisoquinolin-5-yl)-5-cyano-2,4-diethoxybenzamide $^1$H NMR (CDCl$_3$) δ: 1.38 (6H, s), 1.51 (6H, t, J=7 Hz), 2.33 (2H, s), 2.39 (3H, s), 3.56 (2H, s), 4.21 (2H, q, J=7 Hz), 4.37 (2H, q J=7 Hz), 6.53 (1H, s), 6.93 (1H, d, J=7 Hz), 7.17 (1H, t, J=7 Hz), 7.29 (1H, d. J=7 Hz), 8.58 (1H, s), 9.17 (1H, brs); $^m/_z$ (API$^+$): 408 (MH$^+$).

EXAMPLE 33

N-(2,4,4-Trimethyl-1,2,3,4-tetrahydroisoquinolin-5-yl)-2,4-diethoxy-5-trifluoromethylbenzamide $^1$H NMR (CDCl$_3$) δ: 1.40 (6H, s), 1.50 (6H, m), 2.34 (2H, s), 2.39 (3H, s), 3.56 (2H, s)m 4.18 (2H, q, J=7 Hz), 4.35 (2H, q, J=7 Hz), 6.57 (1H, s), 6.94 (1H, d, J=7 Hz), 7.17 (1H, t, J=7 Hz), 7.31 (1H, d, J=7 Hz), 8.59 (1H, s), 9.27 (1H, brs).

EXAMPLE 34

N-(2,4,4-Trimethyl-1,2,3,4-tetrahydroisoquinolin-5-yl)-2-methoxy-4-iso-propyl-5-trifluoromethylbenzamide $^1$H NMR (CDCl$_3$) δ: 1.32 (6H, d, J=7 Hz), 1.43 (6H, s), 2.33 (2H, s), 2.40 (3H, s), 3.38 (1H, m), 3.57 (2H, s), 4.10 (3H, s), 6.92 (1H, d, J=7 Hz), 7.08 (1H, s), 7.14 (1H, t, J=7 Hz), 7.51 (1H, d, J=7 Hz), 8.62 (1H, s), 9.46 (1H, brs).

EXAMPLE 35

N-(4,4-Dimethyl-1,2,3,4-tetrahydroisoquinolin-5-yl)-5-chloro-2-methoxy-4-iso-propoxybenzamide $^m/_z$ (API$^+$): 403 (MH$^+$, 90%; C$_{22}$H$_{27}$ClN$_2$O$_3$ requires M$^+$ 402).

EXAMPLE 36

N-(4,4-Spirocyclopentyl-2-methyl-1,2,3,4-tetrahydroisoquin-7-yl)-3-bromo-4-ethoxybenzamide $^1$H NMR (CDCl$_3$) δ: 1.49 (3H, t, J=7 Hz), 1.67–1.93 (8H, m), 2.35–2.50 (5H, m), 3.47 (2H, s), 4.12 (2H, q, J=7 Hz), 6.83 (1H, d, J=8 Hz), 7.20 (1H, d, J=8 Hz), 7.27 (1H, s), 7.39 (1H, dd, J=8, 2 Hz), 7.76 (1H, dd, J=8, 2 Hz), 8.04 (1H, d, J=2 hz), 8.11 (1H, brs); $^m/_z$ (API$^+$): 443, 445 (MH$^+$).

EXAMPLE 37

N-(4,4-Spirocyclopentyl-2-methyl-1,2,3,4-tetrahydroisoquinolin-7-yl)-3-methoxy-3-tisfluoromethyl Benzamide $^1$H NMR (CDCl$_3$) δ: 1.80 (8H, m), 2.39 (2H, s), 2.42 (3H, s), 3.53 (2H, s), 3.98 (3, s), 7.07 (1H, d, J=9 Hz), 7.27 (1H, d, J=3 Hz, obscured by CHCl$_3$), 7.31 (1H, s), 7.39 (1H, dd, J=8, 2 Hz), 7.76 (1H, s), 8.05 (2H, m); $^m/_z$ (API$^+$): 419 (MH$^+$).

EXAMPLE 38

N-(4,4-Spirocyclopentyl-2-methyl-1,2,3,4-tetrahydroisoquinolin-7-yl)-3-cyano-4-iso-propyl Benzamide $^1$H NMR (CDCl$_3$) δ: 1.34 (6H, d, J=7 Hz), 1.80 (8H, m), 2.39 (2H, s), 2.42 (3H, s), 3.44 (1H, m), 3.54 (2H, s), 7.27 (1H , d, J=8 Hz, obscure by CHCl$_3$), 7.32 (1H, s), 7.38 (1H, dd, J=8, 2 Hz), 7.52 (1H, d, J=8 Hz), 7.85 (1H, s), 8.04 (1H, dd, J=8, 2 Hz), 8.10 (1H, d, J=2 Hz); $^m/_z$ (API$^+$): 338 (MH$^+$).

EXAMPLE 39

N-(4,4-Spirocyclopentyl-2-methyl-1,2,3,4-tetrahydroisoquinolin-7-yl)-3-chloro-4-iso-propyloxybenzamide $^1$H NMR (CDCl$_3$) δ: 1.42 (6H, d, J=6 Hz), 1.80 (8H, m), 2.39 (2H, s), 2.42 (3H, s), 3.54 (2H, s), 4.66 (1H, m, J=6 Hz), 6.99 (1H, d, J=9 Hz), 7.26 (1H, d, J=9 Hz, obscured by CHCl$_3$), 7.31 (1H, d, J=2 Hz), 7.37 (1H, dd, J=8, 2 Hz), 7.64 (1H, s), 7.73 (1H, dd, J=8, 2 Hz), 7.87 (1H, d, J=2 Hz); $^m/_z$ (API$^+$): 435, 437 (MH$^+$).

EXAMPLE 40

N-(4,4-Spirocyclopentyl-2-methyl-1,2,3,4-tetrahydroisoquinolin-7-yl)-4-bromo-4-ethylbenzamide $^1$H NMR (CDCl$_3$) δ: 1.25 (3H, t, J=8 Hz), 1.80 (8H, m), 2.39 (2H, s), 2.42 (3H, s), 2.82 (2H, q, J=8 Hz), 3.53 (2H, s), 7.29 (3H, m), 7.38 (1H, dd, J=8, 2 Hz), 7.72 (2H, m), 8.01 (1H, d, J=2 Hz); $^m/_z$ (API$^+$): 427, 429 (MH$^+$).

EXAMPLE 41

N-(2,4,4-Trimethyl-1,2,3,4-tetrahydroisoquinolin-7-yl)-4-ethoxy-3-trifluoromethyl-benzamide, Hydrochloride $^1$H NMR (250 MHz; d$_6$DMSO) δ: 1.38 (6H, m), 1.48 (3H, s), 2.97 (3H, m), 3.37 (2H, m), 4.25–4.50 (4H, m), 7.45 (1H, d, J=8.5 Hz), 7.66–7.71 (2H, m), 8.29 (2H, m), 10.45 (2H, brs); $^m/_z$ (API$^+$): 407 (MH$^+$).

EXAMPLE 42

N-(2,4,4-Trimethyl-1,2,3,4-tetrahydroisoquinolin-7-yl)-4-iso-propyl-3-trifluoromethylsulfonylbenzamide, Hydrochloride $^1$H NMR (250 MHz, d$_6$ DMSO) δ: inter alia 1.32 (6H, m), 1.45 (3H, s), 3.15–3.60 (2H, m), 3.84 (1H, sep, J=6.5 Hz), 4.26 (2H, m), 7.53 (1H, d, J=8.5 Hz), 7.67 (2H, m), 8.11 (1H, d, J=8 Hz), 8.56 (2H, m), 10.39 (1H, br), 10.73 (1H, s); $m/z$ (API$^+$): 469 (MH$^+$).

EXAMPLE 43

N-(4,4-Dimethyl-1,2,3,4-tetrahydroisoquinolin-7-yl)-3-bromo-4-ethoxybenzamide $^1$H NMR (CDCl$_3$,) δ: 1.27 (6H, s), 1.51 (3H, t), 2.87 (2H, s), 4.01 (2H, s), 4.17 (2H, q), 6.93 (1H, d), 7.33 (3H, s), 7.66 (1H, s), 7.79 (1H, dd), 8.04 (1H, d); $m/z$ (API$^+$): 403 (M$^+$; 100%).

EXAMPLE 44

N-(8-Ethyl-2,4,4-trimethyl-1,2,3,4-tetrahydroisoquinolin-7-yl)-3-bromo-4-ethoxybenzamide $^1$H NMR (CDCl$_3$) δ: 1.18 (3H, t), 1.35 (6H, s), 1.52 (3H, t), 2.57 (9H, m), 4.18 (2H, q), 6.95 (1H, d), 7.24 (1H, d), 7.57 (2H, m), 7.80 (1H, dd), 8.08 (1H, d); $m/z$ (API$^+$): 445.2 (M$^{30}$; 90%).

EXAMPLE 45

N-(8-Ethyl-2,4,4-trimethyl-1,2,3,4-tetrahydroisoquinolin-7-yl)-4-methoxy-3-trifluoromethylbenzamide $^1$H NMR (CDCl$_3$,) δ: 1.15 (3H, t), 1.30 (6H, s), 2.40 (2H, s), 2.47 (3H, s), 2.55 (2H, q), 3.56 (2H, s), 3.98 (3H, s), 7.04 (1H, d), 7.23 (1H, d), 7.53 (1H, d), 7.69 (1H, s), 8.04 (1H, d), 8.09 (1H, s); $m/z$ (API$^+$): 421.1 (MH$^+$; 100%).

EXAMPLE 46

N-(8-Ethyl-2,4,4-trimethyl-1,2,3,4-tetrahydroisoquinolin-7-yl)-3-bromo-4-isopropyloxybenzamide $^1$H NMR (CDCl$_3$) δ: 1.17 (3H, t), 1.32 (6H, s), 1.42 (6H, d), 2.41 (2H, s), 2.48 (3H, s), 2.56 (2H, q), 3.57 (2H, s), 4.67 (1H, m), 6.96 (1H, d), 7.24 (1H, d), 7.55 (1H, d), 7.59 (1H, s), 7.77 (1H, dd), 8.07 (1H, d); $m/z$ (API$^+$): 459.1 (M$^+$; 100%)

EXAMPLE 47

N-(8-Ethyl-2,4,4-trimethyl-1,2,3,4-tetrahydroisoquinolin-7-yl)-3-cyano-4-isopropylbenzamide $^1$H NMR (CDCl$_3$) δ: 1.16 (3H, t), 1.34 (12H, m), 2.49 (2H, s), 2.53 (3H, s), 2.57 (2H, q), 3.45 (1H, m), 3.66 (2H, s), 7.25 (1H, d), 7.53 (2H, d), 7.75 (1H, s), 8.04 (1H, d), 8.12 (1H, d); $m/z$ (API$^+$): 390.2 (MH$^+$; 100%)

EXAMPLE 48

N-(8-Ethyl-2,4,4-trimethyl-1,2,3,4-tetrahydroisoquinolin-7-yl)-3-acetyl-4-isopropyloxybenzamide $^1$H NMR (CDCl$_3$) δ: 1.17 (3H, t), 1.31 (6H, s), 1.45 (6H, d), 2.40 (2H, s), 2.48 (3H, s), 2.58 (2H, q), 2.66 (3H, s), 3.58 (2H, s), 4.81 (1H, m), 7.07 (1H, d), 7.24 (1H, d), 7.58 (1H, d), 7.65 (1H, s), 8.11 (1H, dd), 8.18 (1H, d); $m/z$ (API$^+$): 423.1 (MH$^+$; 100%)

EXAMPLE 49

N-(5-Chloro-1,1,2-trimethyl-1,2,3,4-tetrahydroisoquinolin-7-yl)-3-bromo-4-ethyl benzamide $^1$H NMR (250 MHz, CDCl$_3$) δ: 1.26 (3H, t, J=7.5 Hz), 1.43 (6H, s), 2.43 (3H, s), 2.89(6H, m), 7.34(1H, d, J=8 Hz), 7.47 (1H, d, J=2 Hz), 7.56(1H, d, J=2 Hz), 7.69 (1H, brs), 7.74 (1H, dd, J=8, 2 Hz), 8.02 (1H, d, J=2 Hz); $m/z$ (API$^+$): 435, 437 (MH$^+$).

EXAMPLE 50

N-(5-Chloro-1,1,2-trimethyl-1,2,3,4-tetrahydroisoquinolin-7-yl)-3-cyano-4-isopropylbenzamide $^1$H NMR (250 MHz, CDCl$_3$) δ: 1.35 (6H, d, J=7 Hz), 1.43 (6H, s), 2.43 (3H, s), 2.87(4H, m), 3.45(1H, sep, J=7 Hz), 7.48 (1H, d, J=2 Hz), 7.53 (1H, d, J=8 Hz), 7.59 (1H, d, J=2 Hz), 7.80 (1H, brs), 8.06 (1H d, J=8 Hz), 8.11 (1H, d, J=2 Hz); $m/z$ (API$^+$): 396, 398 (MH$^+$).

EXAMPLE 51

N-(5-Chloro-1,1,2-trimethyl-1,2,3,4-tetrahydroisoquinolin-7-y)-4-methoxy-3-trifluoromethylbenzamide $^1$H NMR (250 MHz, CDCl$_3$,) δ: 1.43 (6H, s), 2.43 (3H, s), 2.78 (2H, m), 2.95 (2H, m), 3.99(3H, s), 7.10 (1H, d, J=9 Hz), 7.50 (1H, d, J=2 Hz), 7.55 (1H, d, J=2 Hz), 7.81 (1H, brs), 8.07 (2H, m); $m/z$ (API$^+$): 427,429 (MH$^+$).

EXAMPLE 52

N-(5-Chloro-1,1,2-trimethyl-1,2,3,4-tetrahydroisoquinolin-7-yl)-3-bromo-4-ethoxybenzamide $^1$H NMR (250 MHz, CDCl$_3$) δ: 1.42 (6H, s), 1.51 (3H, t, J=7 Hz), 2.43 (3H, s), 2.81 (2H, m), 2.93 (2H, m), 4.17 (2H, q, J=7 Hz), 6.92 (1H, d, J=8 Hz), 7.48 (1H, d, J=2 Hz), 7.55 (1H, d, J=2 Hz), 7.72 (1H, brs), 7.81 (1H, dd, J=8, 2 Hz), 8.05 (1H, d, J=2 Hz); $m/z$ (API$^+$): 451, 453, 455 (MH$^+$).

EXAMPLE 53

(±) N-(1,2-Dimethyl-1,2,3,4-tetrahydroisoquinoline-7-yl)-4-methoxy-3-trifluoromethylbenzamide $^1$H NMR (CDCl$_3$) δ: 1.42 (3H, d, J=7 Hz), 2.51 (3H, s), 2.71 (1H, m), 2.86 (2H, m), 3.08 (1H, m), 3.65 (1H, q, J=7 Hz), 3.97 (3H, s), 7.06 (2H, d, J=8 Hz), 7.35 (1H, dd, J=8, 2 Hz), 7.49 (1H, d, J=2 Hz), 8.06 (3H, m); $m/z$ (API$^+$): 379 (MH$^+$).

EXAMPLE 54

(±) N-(1-Phenyl-2-methyl-1,2,3,4-tetrahydroisoquinolin-7-yl)-4-methoxy-3-trifluoromethylbenzamide $^1$H NMR (CDCl$_3$) δ: 2.22 (3H, s), 2.54–3.30 (4H, m), 3.91 (3H, s), 4.19 (1H, brs), 6.68–6.78 (1H, m), 6.90–6.97 (1H, m), 7.05–7.30 (6H, m), 7.44–7.63 (1H, m), 7.86–8.00 (3H, m); $m/z$ (API$^+$): 441 (MH$^+$).

EXAMPLE 55

(±) N-(1-Benzyl-2-methyl-1,2,3,4-tetrahydroisoquinolin-7-yl)-4-methoxy-3-trifluoromethylbenzamide $^1$H NMR (CDCl$_3$) δ: 2.45 (3H, s), 2.50–3.28 (6H, m), 3.78 (1H, t, J=6 Hz), 3.93 (3H, s), 7.13 (8H, m), 7.47 (1H, dd, J=8, 2 Hz), 8.00 (2H, m), 8.19 (1H, s); $m/z$ (API$^+$): 454 (M$^+$).

EXAMPLE 56

(±) N-(-1-iso-Propenyl-2-methyl-1,2,3,4-tetrahydroisoquinolin-7-yl)-4-methoxy-3-trifluoromethylbenzamide $^1$H NMR (CDCl$_3$) δ: 1.51 (3H, s), 2.33 (3H, s), 2.98–3.18 (4H, m), 3.65 (1H, brs), 3.96 (3H, s), 5.08 (2H, d, J=1 Hz), 7.03 (1H, d, J=8 Hz), 7.08 (1H, d, J=8Hz), 7.30 (1H, d, J=2 Hz), 7.51 (1H, dd, J=8, 2 Hz), 8.07 (3H, m); $m/z$ (API$^+$): 405.3 (MH$^+$).

EXAMPLE 57

(±) N-(1-Allyl-2-methyl-1,2,3,4-tetrahydroisoquinolin-7-yl)-4-methoxy-3-trifluoromethylbenzamide $^1$H NMR (CDCl$_3$) δ: 2.51 (3H, s), 2.55–2.87 (5H, m), 3.15–3.27 (1H, m), 3.64 (1H, br t, J=6 Hz), 3.96 (3H, s), 5.10 (2H, m), 5.69–5.86 (1H, m), 7.08 (2H, m), 7.40 (1H, dd, J=8, 2 Hz), 7.52 (1H, d, J=2 Hz), 8.11 (2H, m), 8.29 (1H, brs); $m/z$ (API$^+$): 405 (MH$^+$).

EXAMPLE 58

(±) N-(1-iso-Butyl-2-methyl-1,2,3,4-tetrahydroisoquinolin-7-yl)-4-methoxy-3-trifluoromethylbenzamide $^1$H NMR (CDCl$_3$) δ: 0.92 (3H, d, J=7 Hz), 0.97 (3H, d, J=7 Hz), 1.41 (1H, m), 1.67–1.95 (2H, m), 2.46 (3H, s), 2.52–2.66 (1H, m), 2.81–2.99 (2H, m), 3.17–3.30 (1H, m), 3.54–3.63 (1H, m), 3.97 (3H, s), 7.05 (2H, d, J=8 Hz), 7.33 (1H, dd, J=8, 2 Hz), 7.42 (1H, d, J=2 Hz), 7.81 (1H, brs), 8.07 (2H, m); $m/z$ (API$^+$): 421.3 (MH$^{30}$)

EXAMPLE 59

(±) N-(1-iso-Propenyl-2-methyl-1,2,3,4-tetrahydroisoqiuinolin-7-yl)-3-cyano-4-iso-propylbenzamide $^1$H NMR (CDCl$_3$,) δ: 1.34 (6H, d, J=7 Hz), 1.51 (3H, s), 1.70–1.90 (1H, m), 2.33 (3H, s), 2.35–2.48 (1H, m), 2.60–2.74 (1H, m), 3.42 (1H, m), 3.66 (1H, brs), 7.11 (1H, d, J=8 Hz), 7.27 (H, s), 7.44–7.57 (2H, m), 7.95 (1H, brs), 8.06 (1H, dd, J=2 Hz), 8.11 (1H, d, J=2 Hz); $m/z$ (API$^+$): 374 (MH$^+$).

EXAMPLE 60

(±) N-(1-iso-Propenyl-2-methyl-1,2,3,4-tetrahydroisoquinolin-7-yl)-3-cyano4-iso-propoxybenzamide $^1$H NMR (CDCl$_3$)δ: 1.42 (6H, d, J=6 Hz), 1.49 (3H, s), 2.31 (3H, s), 2.37–2.50 (1H, m), 2.58–2.70 (1H, m), 2.96–3.15 (2H, m), 3.62 (1H, brs), 4.64–4.78 (1H, m), 5.05 (2H, d, J=1 Hz), 6.99 (1H, d, J=8 Hz), 7.06 (1H, d, J=8 Hz), 7.33 (1H, d, J=2 Hz), 7.51 (1H, dd, J=8, 2 Hz), 8.10 (2H, m), 8.36 (1H, brs); $m/z$ (API$^+$): 390 (MH$^+$).

EXAMPLE 61

(±) N-(1-iso-Propenyl-2-methyl-1,2,3,4-tetrahydroisoquinolin-7-yl)-3-bromo-4-ethoxybenzamide $^1$H NMR (CDCl$_3$) δ: 1.50 (6H, m), 2.33 (3H, s), 2.46 (1H, m), 2.60–2.72 (1H, m), 3.09 (2H, m), 3.66 (1H, brs), 4.16 (2H, q, J=7 Hz), 5.11 (2H, d, J=1 Hz), 6.91 (1H, d, J=8 Hz), 7.09 (1H, d, J=8 Hz), 7.25 (1H, d, J=2 Hz), 7.53 (1H, d, J=8, 2 Hz), 7.75 (1H, brs), 7.80 (1H, dd, J 8, 2 Hz), 8.05 (1H, d, J=2 Hz); $m/z$ (API$^+$): 427,429 (MH$^+$).

EXAMPLE 62

(±) N-(1-iso-Propenyl-2-methyl-1,2,3,4-tetrahydroisoquinolin-7-yl)-3-bromo-4-ethylbenzamide $^1$H NMR (CDCl$_3$) δ: 1.24 (3H, t, J=7 Hz), 1.52(3H, s), 2.33 (3H, s),2.41–2.54 (1H, m), 2.67 (1H, m), 2.83 (2H, q, J=7 Hz), 3.08 (2H, m), 3.65 (1H, s), 5.10 (1H, d, J=1 Hz), 7.09 (1H, d, J=8 Hz), 7.26 (1H, d, J=8 Hz), 7.53 (1H, dd, J=8, 2 Hz), 7.83 (1H, brs), 8.02 (1H, d, J=2 Hz); $m/z$ (API$^+$): 413,415 (MH$^+$).

EXAMPLE 63

(±) N-(1-iso-Propenyl-2-methyl-1,2,3,4-tetrahydroisoquinolin-7-yl)-3-chloro-4-iso-propoxybenzamide $^1$H NMR (CDCl$_3$,) δ: 1.41 (6H, d, J=7 Hz), 1.51 (3H, s), 2.32 (3H, s), 2.47 (1H, m), 2.67 (1H, m), 2.98–3.16 (2H, m), 3.64 (1H, s), 4.58–4.70 (1H, m), 5.09 (2H, d, J=1 Hz), 6.95 (1H, d, J=8 Hz), 7.08 (1H, d, J=8 Hz), 7.26 (1H, m), 7.52 (1H, dd, J=8, 2 Hz), 7.73 (1H, dd, J=8, 2 Hz), 7.85 (1H, s), 7.88 (1H, d, J2 Hz); $m/z$ (API$^+$): 399 (MH$^+$).

EXAMPLE 64

(±)N(1-iso-Propyl-methyl1,2,3,4-tetrahydroisoquinolin-7-yl)-4-methoxy-3-trifluoromethylbenzamide E56 (168 mg ) and 10% Pd/C (0.01 g) in methanol (20 ml ) were rapidly stirred under a hydrogen atmosphere for 1 h. The catalyst was then removed by filtration and the filtrate evaporated. The resultant residue was purified by chromatography through silica gel eluting with a dichloromethane solution of ammonia in methanol (0.5% conc. ammonia: 4.5% methanol: 95% dichloromethane) to give the title compound (64 mg, 38%).

$^1$H NMR (CDCl$_3$) δ: 0.88 (3H, d, J=7 Hz), 1.02 (3H, d, J=7 Hz), 1.87–2.03 (1H, m), 2.47 (3H, s), 2.62–2.81 (3H, m), 3.17–3.40 (2H, m), 3.97 (3H, s), 7.05 (1H, d, J=8 Hz), 7.33 (1H, dd, J=8, 2 Hz), 7.93 (1H, brs), 8.07 (3H, m); $m/z$ (API$^+$): 406 (MH$^+$).

EXAMPLE 65

N-(1,1,2-Trimethyl-1,2,3,4-tetrahydroisoquinolin-7-yl)-3-cyano-4-iso-propyl-benzamide $^1$H NMR (CDCl$_3$) δ: 1.32 (6H, d, J=7 Hz), 1.53 (6H, s), 2.57 (3H, s), 2.96 (2H, t, J=6 Hz), 3.09 (2H, t, J=6 Hz), 3.32–3.52 (1H, m), 7.06 (1H, d, J=8 Hz), 7.45 (1H, dd, 8, 2 Hz), 7.51 (1H, d, J=8 Hz), 7.68 (1H, d, J=1 Hz), 8.14 (1H, dd, J=8, 2 Hz), 8.18(1H, d, J=2 Hz), 8.46 (1H, brs); $m/z$ (API$^+$): 362 (MH$^+$).

EXAMPLE 66

N-(1,1,2-Trimethyl-1,2,3,4-tetrahydroisoquinolin-7-yl)-3-bromo-4-ethylbenzamide $^1$H NMR (CDCl$_3$) δ: 1.26 (3H, t, J=7 Hz), 1.54 (6H, s), 2.56 (3H, s), 2.82 (2H, q, J=7 Hz), 2.97 (2H, m), 3.04–3.11 (2H, m), 7.06 (1H, d, J=8 Hz), 7.35 (2H, m), 7.67 (1H, d, J=2 Hz), 7.79 (1H, dd, J=8, 2 Hz), 8.00 (1H, brs), 8.07 (1H, d, J=8 Hz); $m/z$ (API$^+$): 401, 403 (MH$^+$).

EXAMPLE 67

N-(1,1,2-Trimethyl-1,2,3,4-tetrahydroisoquinolin-7-yl)-3-bromo-4-ethoxybenzamide $^1$H NMR (CDCl$_3$) δ: 1.48 (3H, t, J=7 Hz), 1.58 (6H, s), 2.63 (3H, s), 3.04 (2H, m), 3.16 (2H, m), 4.16 (2H, q, J=7 Hz), 6.93 (1H, d, J=8 Hz), 7.03 (1H, d, J=8 Hz), 7.46 (1H, dd, J=8, 2 Hz), 7.73 (1H, d, J=2 Hz), 7.95 (1H, dd, J=8, 2 Hz), 8.17 (1H, d, J=2 Hz), 8.44 (1H, brs); $m/z$ (API$^+$): 417 419 (MH$^+$).

EXAMPLE 68

N-(1,1,2-Trimethyl-1,2,3,4-tetrahydroisoquinolin-7-yl)-3-chloro-4-iso-propoxybenzamide $^1$H NMR (CDCl$_3$) δ: 1.40 (6H, d, J=7 Hz), 1.48 (6H, s), 2.51 (3H, s), 2.90 (2H, m), 2.99 (2H, m), 4.58–4.73 (1H, m), 6.97 (1H, d, J=8 Hz), 7.03 (1H, d, J=8 Hz), 7.38 (1H, dd, J=8, 2 Hz), 7.64 (1H, d, J=2 Hz), 7.79 (1H, dd, J=8, 2 Hz), 7.92 (1H, d, J=2 Hz), 8.10 (1H, brs); $^m/_z$ (API$^+$): 387, 389 (MH$^+$).

EXAMPLE 69

N-(2,3,3-Trimethyl-1,2,3,4-tetrahydroisoquinolin-7-yl)4-methoxy-3-trifluoromethylbenzamide $^1$H NMR (CDCl$_3$) δ: 1.08 (6H, s), 2.35 (3H, s), 2.67 (2H, s), 3.68 (2H, s), 3.94 (3H, s), 7.00 (1H, d, J=8 Hz), 7.29 (1H, dd, J=8, 2 Hz), 740 (1H, d, J=2 Hz), 8.02 (1H, dd, J=8, 2 Hz), 8.06 (1H, s), 8.13 (1H, brs); $^m/_z$ (API$^+$): 393 (MH$^+$).

EXAMPLE 70

N-(2,3,3-Trimethyl-1,2,3,4-tetrahydroisoquinolin-7-yl)-3-cyano-4-iso-propylbenzamide $^1$H NMR (CDCl$_3$) δ: 1.07 (6H, s), 1.31 (6H, d, J=7 Hz), 2.34 (3H, s), 2.66 (3H, s), 3.39 (1H, overlapping m, J=7 Hz), 3.66 (2H, s), 7.00 (1H, d, J=8 Hz), 7.32 (1H, dd, J=8, 2 Hz), 8.05 (1H, dd, J=8, 2 Hz), 8.11 (1H, d, J=2 Hz), 8.44 (1H, brs); $^m/_z$ (API$^+$): 362 (MH$^+$).

EXAMPLE 71

N-(2,3,3-Trimethyl-1,2,3,4-tetrahydroisoquinolin-7-yl)-3-bromo-4-ethylbenzamide $^1$H NMR (CDCl$_3$) δ: 1.08 (6H, s), 1.24 (3H, t, J=7 Hz), 2.36 (3H, s), 2.67 (2H, s), 2.79 (2H, q, J=7 Hz), 3.70 (2H, s), 7.02 (1H, d, J=8 Hz), 7.29 (1H, d, J=8 Hz), 7.42(1H, d, J=2 Hz), 7.71 (1H, dd, J=8, 2 Hz), 7.92 (1H, brs), 7.99(1H, d, J=2 Hz); $^m/_z$ (API$^+$): 401, 403 (MH$^+$).

EXAMPLE 72

N-(2,3,3-Trimethyl-1,2,3,4-tetrahydroisoquinolin-7-yl)-3-bromo-4-ethoxybenzamide $^1$H NMR (CDCl$_3$) δ: 1.10 (6H, s), 1.49 (3H, t, J=7 Hz), 2.38 (3H, s), 2.69 (2H, s), 3.72(2H, s), 4.14(2H, q, J=7 Hz), 6.88 (1H, d, J=8 Hz), 7.01 (1H, d, J=8 Hz), 7.32(1H, dd, J=8, 2 Hz), 7.41 (1H, d, J=2 Hz), 7.87 (1H, dd, J=8, 2 Hz), 7.93 (1H, brs), 8.04(1H, d, J=2 Hz); $^m/_z$ (API$^+$): 417, 419 (MH$^+$).

EXAMPLE 73

N-(2,3,3-Trimethyl-1,2,3,4-tetrahydroisoquinolin-7-yl)-3-chloro-4-iso-propoxybenzamide $^1$H NMR (CDCl$_3$) δ: 1.07 (6H, s), 1.39 (6H, d, J=7 Hz ), 2.35 (3H, s), 2.66 (2H, s), 3.68 (2H, s), 4.62 (1H, m), 6.91 (1H, d, J=8 Hz), 6.99 (1H, d, J=8 Hz), 7.29 (1H, dd, J=8, 2 Hz ), 7.40 5(1H, d, J=8 Hz), 7.71 (1H, dd, J 8, 2 Hz), 7.87 (1H, d, J=2 Hz), 8.05 (1H, brs); $^m/_z$ (API$^+$): 387, 389 (MH$^+$).

EXAMPLE 74

N-(4,4-Spirocyclobutyl-2-methyl-1,2,3,4-tetrahydroisoquinolin-7-yl)-3-cyano-4-iso-propylbenzamide $^1$H NMR (CDCl$_3$)δ: 1.33 (6H, d, J=7 Hz), 1.95–2.17 (4H, m), 2.23–2.42 (2H, m), 2.47(3H, s), 2.72 (2H, s), 3.41 (1H, m), 3.52(2H, s), 7.33 (1, H, brs), 7.42–7.65 (3H, m), 7.97 (1H, brs), 8.05 (1H, dd, J=8, 2 Hz), 8.11 (1H, d, J=2 Hz); $^m/_z$ (API$^+$): 374 (MH$^+$).

EXAMPLE 75

N-(4,4-Spirocyclobutyl-2-methyl1,2,3,4-tetrahydroisoquinolin-7-yl)-3-bromo-4-ethoxybenzamide $^1$H NMR (CDCl$_3$) δ: 1.51 (3H, t, J=7 Hz), 1.92–2.18 (4H, m), 2.23–2.50 (2H, m), 2.47 (3H, s), 2.72 (2H, s), 3.53 (2H, s), 4.16 (2H, q, J=7 Hz), 6.92 (1H, d, J=8 Hz), 7.32 (1H, s), 7.43 (1H, m), 7.57 (1H, d, J=8 Hz), 7.74 (1H, s), 7.79 (1H, dd, J=8, 2 Hz), 8.05 (1H, d, J=2 Hz); $^m/_z$ (API$^+$): 429, 431 (MH$^+$).

EXAMPLE 76

N-(4,4-Spirocyclobutyl-2-methyl-1,2,3,4-tetrahydroisoquinolin-7-yl)-3-chloro-4-iso-propoxybenzamide $^1$H NMR (CDCl$_3$) δ: 1.40 (6H, d, J=7 Hz), 1.85–2.20 (4H, m), 2.22–2.50 (2H, m), 2.45 (3H, s), 2.70 (2H, s), 3.70 (2H, s), 4.56–4.73 (1H, m), 6.93 (1H, d, J=8 Hz), 7.27 (1H, s), 7.41 (1H, dd, J=8, 2 Hz), 7.55 (1H, d, J=8 Hz), 7.72 (1H, dd, J=8, 2 Hz), 7.88 (1H, d, J=2 Hz), 7.98 (1H, brs); $^m/_z$ (API$^+$): 399, 401 (MH$^+$).

EXAMPLE 77

N-(4,4-Spirocyclobutyl-2-methyl-1,2,3,4-tetrahydroisoquinolin-7-yl)-4-methoxy-3-trifluoromethylbenzamide $^1$H NMR (CDCl$_3$) δ: 1.97–2.17 (4H, m), 2.25–2.44 (2H, m), 2.47 (3H, s), 2.71 (2H, s), 3.50 (2H, s), 3.96 (3H, s), 7.03 (1H, d, J=8 Hz), 7.36 (1H, d, J=2 Hz), 7.44 (1H, dd, J=8, 2 Hz), 7.56 (1H, d, J=8 Hz), 7.91 (1H, brs), 8.04 (2H, m); $^m/_z$ (API$^+$): 405 (MH$^+$).

EXAMPLE 78

N-(4,4-Spirocyclobutyl-2-methyl-1,2,3,4-tetrahydroisoquinolin-7-yl)-4-ethoxy-3-trifluoromethylbenzamide $^1$H NMR (CDCl$_3$) δ: 1.48 (3H, t, J=7 Hz), 1.98–2.17 (4H, m), 2.24–2.42 (2H, m), 2.47 (3H, s), 2.72 (2H, s), 3.54 (2H, s), 4.20 (2H, q, J=7 Hz), 7.04 (1H, d, J=8 Hz), 7.32 (1H, d, H=2 Hz), 7.44 (1H, dd, J=8, 2 Hz), 7.58 (1H, d, J=8 Hz), 7.73 (1H, brs), 8.01 (2H, m); $^m/_z$ (API$^+$): 419 (MH$^+$).

EXAMPLE 79

(±) N-(1,2,4,4-Tetramethyl-1,2,3,4-tetrahydroisoquinolin-7-yl)4-methoxy-3-trifluoromethylbenzamide $^1$H NMR (CDCl$_3$) δ: 1.19 (3H, s), 1.24 (3H, s), 1.28 (3H, d J=6 Hz), 2.26 (1H, d, J=12 Hz), 2.37 (3H, s), 2.56 (1H, d, J=12 Hz), 3.44 (1H, q, J=6 Hz), 3.89 (3H, s), 6.95 (1H, d, J=8 Hz), 7.18 (1H, d, H=8 Hz), 7.30 (1H, dd, J=8, 2 Hz), 7.35 (1H, d, J=2 Hz), 7.96 (3H, m); $^m/_z$ (API$^+$): 407 (MH$^+$).

EXAMPLE 80

(±)N-(1,2,4,4-Tetramethyl-1,2,3,4-tetrahydroisoquinolin-7-yl)-3-cyano-4-iso-propoxybenzamide $^1$H NMR (CDCl$_3$) δ: 1.13–1.40 (15H, m), 2.25 (1H, d, J=12 Hz), 2.31 (3H, s), 2.51 (1H, d, J=12 Hz), 3.43 (1H, q, J=7 Hz), 4.64 (1H, m), 6.92 (1H, d, J=8 Hz), 7.17 (1H, d, J=8 Hz), 7.36 (2H, m), 7.83 (2H, m), 8.33 (1H, brs); $^m/_z$ (API$^+$): 392 (MH$^+$).

EXAMPLE 81

(±) N-(1,2,4,4-Tetramethyl-1,2,3,4-tetrahydroisoquinolin-7-yl)-3-cyano-4-iso-propylbenzamide $^1$H NMR (CDCl$_3$,) δ: 1.20 (3H, s), 1.22–1.31 (12H, m), 2.23 (1H, d, J=12 Hz), 2.34 (3H, s), 2.57 (1H, d, J=12 Hz), 3.35 (1H, m), 3.47 (1H, q, J=7 Hz), 7.21 (1H, d, J=8 Hz), 7.35 (2H, m), 7.41 (1H, d, J=8 Hz), 8.00 (2H, m), 8.06 (1H, d, J=2 Hz); $^m/_z$ (API$^+$): 376 (MH$^+$).

EXAMPLE 82

(±)N-(1,2,4,4-Tetramethyl-1,2,3,4-tetrahydroisoquinolin-7-yl)-3-chloro-4-iso-propoxybenzamide $^1$H NMR (CDCl$_3$) δ: 1.26 (3H, s), 1.31 (3H, s), 1.34 (3H, d, J=6 Hz), 1.39 (6H, J=7 Hz), 2.34 (1H, d, J=12 Hz), 2.44 (3H, s), 2.63 (1H, d, J=12 Hz), 3.51 (1H, q, J=7 Hz), 4.62 (1H, m), 6.89 (1H, d, J=8 Hz), 7.24 (1H, d, J=8 Hz), 7.40 (2H, m), 7.73 (1H, dd, J=8, 2 Hz), 7.89(1H, d,J=2 Hz), 8.16 (1H, brs); $^m/_z$ (API$^+$): 399, 401 (MH$^+$).

EXAMPLE 83

(±) N-(1,2,4-Tetramethyl-1,2,3,4-tetrahydroisoquinolin-7-yl)-3-bromo-4-ethylbenzamide $^1$H NMR (CDCl$_3$) δ: 1.20–1.34 (9H, m), 1.37 (3H, d, J=6 Hz), 2.34 (1H, d, J=12 Hz), 2.46 (3H, s), 2.65 (1H, d, J=12 Hz), 2.80 (2H, q, J=7 Hz), 3.56(1H, q, J=6 Hz), 7.30 (4H, m), 7.73 (1H, dd, J=8, 2 Hz), 7.86 (1H, brs), 8.02 (1H, d, J=2 Hz); $^m/_z$ (API$^+$): 415,417 (MH$^+$).

EXAMPLE 84

(±) N-(1,2,4,4-Tetramethyl-1,2,3,4-tetrahydroisoquinolin-7-yl)-3-bromo-4-ethoxybenzamide $^1$H NMR (CDCl$_3$,) δ: 1.26 (3H, s), 1.31 (3H, s), 1.33 (3H, d, J=7 Hz), 1.47 (3H, t, J=7 Hz), 2.34 (1H, d, J=12 Hz), 2.44 (3H, s), 2.64 (1H, d, J=12 Hz), 3.52 (1H, q, J=7 Hz), 4.13 (2H, q, J=7 Hz), 6.85 (1H, d, J=8 Hz), 7.23 (1H, d, J=8 Hz), 7.37 (2H, m), 7.78 (1H, dd, J=8, 2 Hz), 8.04 (2H, m); $^m/_z$ (API$^+$): 431, 433 (MH$^+$).

EXAMPLE 85

N-(1,1,2,5-Tetramethyl-1,2,3,4-tetrahydroisoquinolin-7-yl)-3-bromo-4-ethylbenzamide Hydrochloride The title compound was prepared from D25 using similar methods to those described in Description 27 [tin(II)chloride reduction] followed by treatment similar to Description 21 [using tetramethyltin] and Example 1.

$^m/_z$ (API$^+$): 415, 417 (MH$^+$, 90%; C$_{22}$H$_{27}$BrN$_2$O requires M$^+$ 415).

EXAMPLE 86

N-(1,1,2,5-Tetramethyl-1,2,3,4-tetrahydroisoquinolin-7-yl)-3-cyano-4iso-propylbenzamide Hydrochloride $^m/_z$ (API$^+$): 376 (MH$^+$, 100%; C$_{24}$H$_{29}$N$_3$O requires M$^+$ 375).

EXAMPLE 87

N-(1,1,2,5-Tetramethyl-1,2,3,4-tetrahydroisoquinolin-7-yl)-4-methoxy-3-trifluoromethylbenzamide Hydrochloride $^m/_z$ (API$^+$): 407 (MH$^+$, 80%; C$_{22}$H$_{25}$F$_3$N$_2$O$_2$ requires M$^+$ 406).

EXAMPLE 88

N-(1,1,2-Trimethyl-5-trifluoromethyl-1,2,3,4-tetrahydroisoquinolin-7-yl)4-methoxy-3-trifluoromethylbenzamide Hydrochloride The title compound was prepared from D25 and copper (I)trifluoroacetate in a manner similar to that described in Procedure 4 followed by treatment similar to Description 27 and Example 1.

$^m/_z$ (API$^+$): 461 (MH$^+$, 100%; C$_{22}$H$_{22}$F$_6$N$_2$O$_2$ requires M$^+$ 460).

EXAMPLE 89

N-(1,1,2-Trimethyl-5-trifluoromethyl-1,2,3,4-tetrahydroisoquinolin-7-yl)-3-bromo-4-ethoxybenzamide Hydrochloride $^m/_z$ (API$^+$): 485, 487 (MH$^+$, 90%; C$_{22}$H$_{24}$BrF$_3$N$_2$O$_2$ requires M$^+$ 485).

EXAMPLE 90

N-(1,1,2-Trimethyl-5-trifluoromethyl-1,2,3,4-tetrahydroisoquinolin-7-yl)-3-cyano4-ethoxybenzamide Hydrochloride $^m/_z$ (API$^+$): 432 (MH$^+$, 100%; C$_{23}$H$_{24}$F$_3$N$_3$O$_2$ requires M$^+$ 431).

EXAMPLE 91

N-(2,4,4-Trimethyl-1,2,3,4-tetrahydroisoquinolin-7-yl)-4-ethyl-3-trifluoromethyl-benzamide Hydrochloride $^1$H NMR (250 MHz. d$_6$DMSO)δ inter alia: 1.23 (3H, t, J=7.5 Hz), 1.31 (3H, s), 1.45 (3H, s), 2.90 (5H, m), 3.15–3.30 (ca 1H, m), 4.20–4.50 (2H, m), 7.49 (1H, d, J=8 Hz), 7.65 (3H, m), 8.21 (2H, m), 10.60 (2H, br); $^m/_z$ (API$^+$): 391 (MH$^+$).

EXAMPLE 92

N-(2,4,4-Trimethyl-1,2,3,4-tetrahydroisoquinolin-7-yl)-3-acetyl-4-iso-propyl-benzamide $^1$H NMR (CDCl$_3$) δ: 1.27 (6H, d), 1.31 (6H, s), 2.40 (2H, s), 2.42 (3H, s), 2.63 (3H, s), 3.48 (1H, m), 3.55 (2H, s), 7.33 (3H, m), 7.52 (1H, d), 7.72 (1H, s), 7.84 (1H, dd), 8.00 (1H, d); $^m/_z$ (API$^+$): 379.1 (MH$^+$; 100%).

EXAMPLE 93

N-(2,4,4-Trimethyl-1,2,3,4-tetrahydroisoquinolin-7-yl)-3-acetyl-4-ethoxybenzamide $^1$H NMR (CDCl$_3$) δ: 1.30 (6H, s), 1.51 (3H, t), 2.39 (2H, s), 2.42 (3H, s), 2.68 (3H, s), 3.54 (2H, s), 4.23 (2H, q), 7.06 (1H, d), 7.29 (1H, d), 7.38 (2H, m), 7.82 (1H, s), 8.14 (2H, m); $^m/_z$ (API$^+$): 381.1 (MH$^+$; 80%).

EXAMPLE 94

N-[4,4-Dimethyl-2-(2-methoxyethyl)-1,2,3,4-tetrahydroisoquinolin-7-yl]-3-cyano-4-iso-propoxybenzamide $m/z$ (API$^+$): 422 (MH$^+$, 100%; $C_{25}H_{31}N_3O_3$ requires M$^+$ 421).

EXAMPLE 95

N-[4,4-Dimethyl-2-(2-methoxyethyl)-1,2,3,4-tetrahydroisoquinolin-7-yl]-3-cyano-4-iso-propylbenzamide $m/z$ (API$^+$): 406 (MH$^+$, 100%; $C_{25}H_{31}N_3O_2$ requires M$^+$ 405).

EXAMPLE 96

N-[4,4-Dimethyl-2-(2-methoxyethyl)-1,2,3,4-tetrahydroisoquinolin-7-yl]-4-methoxy-3-trifluoromethylbenzamide Hydrochloride $m/z$ (API$^+$): 437 (MH$^+$, 90%; $C_{23}H_{27}F_3N_2O_3$ requires M$^+$ 436).

EXAMPLE 97

N-(8-Chloro-2,4,4-trimethyl-1,2,3,4-tetrahydroisoquinolin-7-yl)-3-bromo-4-iso-propoxybenzamide $^1$H NMR (CDCl$_3$) δ: 1.31 (6H, s), 1.43 (6H, d), 2.38 (2H, s), 2.48 (3H, s), 3,58 (2H, s), 4.68 (1H, m), 6.97 (1H, d), 7.30 (1H, d), 7.81 (1H, dd), 8.12 (1H, d), 8.25 (1H, s), 8.30 (1H, d); $m/z$ (API$^+$): 465.0 (M$^+$; 80%) expected isotope pattern.

EXAMPLE 98

N-(8-Chloro-2,4,4-trimethyl-1,2,3,4-tetrahydroisoquinolin-7-yl)-4-ethyl-3-trifluoromethylbenzamide $^1$H NMR (CDCl$_3$) δ: 1.26 (3H, t), 1.32 (6H, s), 2.39 (2H, s), 2.48 (3H, s), 2.84 (2H, q), 3.58 (2H, s), 7.32 (1H, d), 7.52 (1H, m), 8.00 (1H, dd), 8.19 (1H, d), 8.31 (1H, d), 8.37 (1H, s); $m/z$ (API$^+$): 425.0 (MH$^+$; 100%).

EXAMPLE 99

N-(8-Chloro-2,4,4-trimethyl-1,2,3,4-tetrahydroisoquinolin-7-yl)-3-acetyl-4-iso-propylbenzamide $^1$H NMR (CDCl$_3$) δ: 1.27 (6H, d), 1.32 (6H, s), 2.39 (2H, s), 2.48 (3H, s), 2.64 (3H, s), 3.51 (1H, m), 3.58 (2H, s), 7.32 (1H, d), 7.55 (1H, d), 7.90 (1H, dd), 8.08 (1H, d), 8.33 (1H, d), 8.39 (1H, s); $m/z$ (API$^+$): 413.1 (MH$^+$; 80%).

EXAMPLE 100

N-(8-Chloro-2,4,4-trimethyl-1,2,3,4-tetrahydroisoquinolin-7-yl)-3-cyano-4-methoxybenzamide $^1$H NMR (CDCl$_3$) δ: 1.31 (6H, s), 2.39 (2H, s), 2.48 (3H, s), 3.58 (2H, s), 4.03 (3H, s), 7.10 (1H, d), 7.32 (1H, d), 8.13 (2H, m), 8.28 (2H, m); $m/z$ (API$^+$): 384.1 (MH$^+$; 100%). $m/z$ (API$^+$): 383 (MH$^+$).

EXAMPLE 101

N-(8-Chloro-2,4,4-trimethyl-1,2,3,4-tetrahydroisoquinolin-7-yl)-4-methoxy-3-trifluoromethylbenzamide $^1$H NMR (CDCl$_3$) δ: 1.32 (6H, s), 2.39 (2H, s), 2.48 (3H, s), 3.58 (2H, s), 4.00 (3H, s), 7.12 (1H, d), 7.32 (1H, d), 8.08 (1H, dd), 8.16 (1H, d), 8.30 (2H, m); $m/z$ (API$^+$): 427.1 (MH$^+$, 100%).

EXAMPLE 102

N-(8-Chloro-2,4,4-trimethyl-1,2,3,4-tetrahydroisoquinolin-7-yl)-3-chloro-4-ethoxybenzamide $^1$H NMR (CDCl$_3$) δ: 1.31 (6H, s), 1.51 (3H, t), 2.38 (2H, s), 2.48 (3H, s), 3.57 (2H, s), 4.17 (2H, q), 6.99 (1H, d), 7.29 (1H, d), 7.78 (1H, dd), 7.95 (1H, d), 8.29 (2H, m); $m/z$ (API$^+$): 407.2 (MH$^+$; 100%).

EXAMPLE 103

N-(8-Chloro-2,4,4-trimethyl-1,2,3,4-tetrahydroisoquinolin-7-yl)-3-bromo-4-ethoxybenzamide $^1$H NMR (CDCl$_3$) δ: 1.31 (6H, s), 1.51 (3H, t), 2.38 (2H, s), 2.48 (3H, s), 3.57 (2H, s), 4.18 (2H, q), 6.95 (1H, d), 7.30 (1H, d), 7.82 (1H, dd), 8.12 (1H, d), 8.28 (2H, m); $m/z$ (API$^+$): 451.1 (M$^+$; 80%).

EXAMPLE 104

N-(8-Chloro-2,4,4-trimethyl-1,2,3,4-tetrahydroisoquinolin-7-yl)-3-bromo-4-iso-propylbenzamide $^1$H NMR (CDCl$_3$) δ: 1.27 (6H, d), 1.31 (6H, s), 2.39 (2H, s), 2.48 (3H, s), 3.43 (1H, m), 3.58 (2H, s), 7.31 (1H, d), 7.41 (1H, d), 7.79 (1H, dd), 8.10 (1H, d), 8.31 (2H, m); $m/z$ (API$^+$): 449.1 (M$^+$; 80%).

EXAMPLE 105

N-(8-Chloro-2,4,4-trimethyl-1,2,3,4-tetrahydroisoquinolin-7-yl)-3-cyano-4-ethylbenzamide $^1$H NMR (CDCl$_3$) δ: 1.32 (6H, s), 1.35 (3H, t), 2.39 (2H, s), 2.48 (3H, s), 2.97 (2H, q), 3.58 (2H, s), 7.32 (1H, d), 7.50 (1H, d), 8.04 (1H, dd), 8.15 (1H, d), 8.27 (1H, s), 8.31 (1H, d); $m/z$ (API$^+$): 382.1 (M$^+$; 100%).

EXAMPLE 106

N-(2,4,4-Trimethyl-1,2,3,4-tetrahydroisoquinolin-7-yl)-4-iso-propoxy-3-trifluoromethylbenzamide Hydrochloride $^1$H NMR (250 MHz, d$_6$DMSO) δ: 1.47–1.51 (9H, m), 1.63 (3H, s), 3.10 (3H, br), 3.45(ca 1H, m), 4.41–4.61 (2H, m), 5.10 (1H, sep, J=6 Hz), 7.63 (1H, d, J=8 Hz), 7.66 (1H, d, J=8 Hz), 7.84 (2H, m), 8.43 (2H, m), 10.59 (1H, s), 10.72 (1H, br); $m/z$ (API$^+$): 421 (MH$^+$).

EXAMPLE 107

N-(8-Ethyl-2,4,4-trimethyl-1,2,3,4-tetrahydroisoquinolin-7-yl)-3-bromo-4-methoxybenzamide $^1$H NMR (CDCl$_3$) δ: 1.17 (3H, t), 1.31 (6H, s), 2.56 (7H, m), 3.67 (2H, s), 3.96 (3H, s), 6.96 (1H, d), 7.25 (1H, d), 7.56 (1H, d), 7.62 (1H, s), 7.96 (1H, dd), 8.22 (1H, d); $m/z$ (API$^+$): 431.1 (M$^+$; 100%).

EXAMPLE 108

N-(8-Ethyl-2,4,4-trimethyl-1,2,3,4-tetrahydroisoquinolin-7-yl)-3-chloro-4-methoxybenzamide $^1$H NMR (CDCl$_3$) δ: 1.17 (3H, t), 1.32 (6H, s), 2.41 (2H, s), 2.48 (3H, s), 2.57 (2H, q), 3.57 (2H, s), 3.98 (3H, s), 7.00

(1H, d), 7.24 (1H, d), 7.57 (2H, m), 7.77 (1H, dd), 7.91 (1H, d); $^m/_z$ (API$^+$): 387.2 (M$^+$; 100%).

EXAMPLE 109

N-(8-Ethyl-2,4,4-trimethyl-1,2,3,4-tetrahydroisoquinolin-7-yl)-3-chloro-4-ethoxybenzamide $^1$H NMR (CDCl$_3$) δ: 1.18 (3H, t), 1.33 (6H, s), 1.49 (3H, t), 2.43 (2H, s), 2.50 (3H, s), 2.61 (2H, q), 3.60 (2H, s) 4.19 (2H, q), 6.99 (1H, d), 7.24 (1H, d), 7.54 (1H, s), 7.59 (1H, d), 7.74 (1H, dd), 7.90 (1H, d); $^m/_z$ (API$^+$): 401.2 (M$^+$; 100%).

EXAMPLE 110

N-(8-Ethyl-2,4,4-trimethyl-1,2,3,4-tetrahydroisoquinolin-7-yl)-3-bromo-4-ethylbenzamide $^1$H NMR (CDCl$_3$) δ: 1.18 (3H, t), 1.29 (3H, t), 1.34 (6H, s), 2.46 (2H, s), 2.47 (3H, s), 2.58 (2H, q), 2.83 (2H, q), 3.63 (2H, s), 7.25 (1H, d), 7.35 (1H, d), 7.61 (2H, m), 7.72 (1H, dd), 8.05 (1H, d); $^m/_z$ (API$^+$): 429.1 (M$^+$; 100%).

EXAMPLE 111

N-(8-Methyl-2,4,4-trimethyl-1,2,3,4-tetrahydroisoquinolin-7-yl)-3-bromo-4-ethoxybenzamide $^1$H NMR (CDCl$_3$) δ: 1.31 (6H, s), 1.52 (3H, t), 2.09 (3H, s), 2.39 (2H, s), 2,46 (3H, s), 3.47 (2H, s), 4.18 (2H, q), 6.95 (1H, d), 7.23 (1H, d), 7.42 (1H, d). 7.52 (1H, s), 7.82 (1H, dd), 8.09 (1H, d); $^m/_z$ (API$^+$): 431.1 (M$^+$; 95%).

EXAMPLE 112

N-(8-Methyl-2,4,4-trimethyl-1,2,3,4-tetrahydroisoquinolin-7-yl)-4-methoxy-3-trifluoromethylbenzamide $^1$H NMR (CDCl$_3$) δ: 1.31 (6H, s), 2.11 (3H, s), 2.38 (2H, s), 2.47 (3H, s), 3.48 (2H, s), 3.99 (3H, s), 7.10 (1H, d), 7.24 (1H, d), 7.43–7.53 (2H, m), 8.08 (2H, m); $^m/_z$ (API$^+$): 407.2 (MH$^+$; 100%).

EXAMPLE 113

N-(8-Methyl-2,4,4-trimethyl-1,2,3,4-tetrahydroisoquinolin-7-yl)-3-chloro-4-ethoxybenzamide $^1$H NMR (CDCl$_3$) δ: 1.31 (6H, s), 1.49 (3H, t), 2.09 (3H, s), 2.38 (2H, s), 2.46 (3H, s), 3.47 (2H, s), 4.19 (2H, q), 6.98 (1H, d), 7.23 (1H, d), 7.43 (1H, d), 7.52 (1H, s), 7.77 (1H, dd), 7.92 (1H, d); $^m/_z$ (API$^+$): 387.2 (MH$^+$; 100%).

EXAMPLE 114

N-(8-Methyl-2,4,4-trimethyl-1,2,3,4-tetrahydroisoquinolin-7-yl)-3-cyano-4-ethylbenzamide $^1$H NMR (CDCl$_3$) δ: 1.37 (3H, t), 1.43 (6H, s), 2.12 (3H, s), 2.74 (3H, s), 2.79 (2H, s), 2.95 (2H, q), 7.26 (1H, d), 7.46 (2H, m), 8.11 (2H, m), 8.20 (1H, d); $^m/_z$ (API$^+$): 362.3 (MH$^+$; 100%).

EXAMPLE 115

N-(8-Bromo-2,4,4-trimethyl-1,2,3,4-tetrahydroisoquinolin-7-yl)-3-bromo-4-methoxybenzamide $^1$H NMR (CDCl$_3$) δ: 1.31 (6H, s), 2.38 (2H, s), 2.48 (3H, s), 3.55 (2H, s), 3.97 (3H, s), 6.99 (1H, d), 7.35 (1H, d), 7.87 (1H, dd), 8.14 (1H, d), 8.26 (1H, d), 8.33 (1H, s); $^m/_z$ (API$^+$): 483.0 (MH$^+$; 100%).

EXAMPLE 116

N-(8-Bromo-2,4,4-trimethyl-1,2,3,4-tetrahydroisoquinolin-7-yl)-4-methoxy-3-trifluoromethylbenzamide $^1$H NMR (CDCl$_3$) δ: 1.32 (6H, s), 2.39 (2H, s), 2.48 (3H, s), 3.55 (2H, s), 4.00 (3H, s), 7.12 (1H, d), 7.36 (1H, d), 8.10 (1H, dd), 8.18 (1H, d), 8.29 (1H, d), 8.36 (1H, s); $^m/_z$ (API$^+$): 471.1 (M$^+$; 85%).

EXAMPLE 117

N-(2,4,4-Trimethyl-1,2,3,4-tetrahydroisoquinolin-7-yl)-3-acetyl-4-ethylbenzamide $^1$H NMR (CDCl$_3$) δ: 1.24 (3H, t), 1.31 (6H, s), 2.42 (2H, s), 2.43 (3H, s), 2.64 (3H, s), 2.93 (2H, q), 3.56 (2H, s), 7.29–7.41 (4H, m), 7.73 (1H, s), 7.81 (1H, dd), 8.15 (1H, d).

EXAMPLE 118

N-(2,4,4-Trimethyl-1,2,3,4-tetrahydroisoquinolin-7-yl)-4-ethoxy-3-propionylbenzamide $^1$H NMR (CDCl$_3$) δ: 1.17 (3H, t), 1.29 (6H, s), 1.51 (3H, t), 2.39 (2H, s), 2.41 (3H, s), 3.03 (2H, q), 3.52 (2H, s), 4.19 (2H, q), 7.02 (1H, d), 7.28 (1H, d), 7.38 (2H, m), 8.00 (1H, s), 8.10 (2H, m); $^m/_z$ (API$^+$): 395.2 (MH$^+$; 100%).

EXAMPLE 119

N-(2,4,4-Trimethyl-1,2,3,4-tetrahydroisoquinolin-7-yl)-4-iso-propoxy-3-propionylbenzamide $^1$H NMR (CDCl$_3$) δ: 1.17 (3H, t), 1.30 (6H, s), 1.43 (6H, d), 2.39 (2H, s), 2.41 (3H, s), 3.02 (2H, q), 3.52 (2H, s), 4.77 (1H, m), 7.03 (1H, d), 7.28 (1H, d), 7.38 (2H, m), 7.96 (1H, s), 8.10 (2H, m); $^m/_z$ (API$^+$): 409.2 (MH$^+$; 100%).

EXAMPLE 120

N-(2,4,4-Trimethyl-1,2,3,4-tetrahydroisoquinolin-7-yl)-3-iso-butyroyl-4-methoxybenzamide $^1$H NMR (CDCl$_3$) δ: 1.17 (6H, d), 1.30 (6H, s), 2.39 (2H, s), 2.42 (3H, s), 3.51 (3H, m), 3.97 (3H, s), 7.06 (1H, d), 7.36 (3H, m), 7.76 (1H, s), 7.96(1H, d), 8.08 (1H, dd); $^m/_z$ (API$^+$): 395.2 (MH$^+$; 100%).

EXAMPLE 121

N-(2,4,4-Trimethyl-1,2,3,4-tetrahydroisoquinolin-7-yl)-4-ethoxy-3-iso-butyroyl Benzamide $^1$H NMR (CDCl$_3$) δ: 1.17 (6H, d), 1.30 (6H, s), 1.49 (3H, t), 2.39 (2H, s), 2.41 (3H, s), 3.53 (2H, s), 4.19 (2H, q), 7.02 (1H, d), 7.35 (2H, m), 7.84 (1H, s), 7.97 (1H, d), 8.06 (1H, dd).

EXAMPLE 122

N-(2,4,4-Trimethyl-1,2,3,4-tetrahydroisoquinolin-7-yl)-3-iso-butyroyl-4-iso-propoxybenzamide $^1$H NMR (CDCl$_3$) δ: 1.16 (6H, d), 1.30 (6H, s), 1.42 (6H, d), 2.39 (2H, s), 2.41 (3H, s), 3.53 (3H, m), 4.76 (1H, m), 7.02 (1H, d), 7.35 (3H, m), 7.90 (1H, s), 7.96 (1H, d), 8.05 (1H, dd); m$_{/z}$ (API$^+$): 423.6 (MH$^+$: 100%).

EXAMPLE 123

N-(2,4,4-Trimethyl-1,2,3,4-tetrahydroisoquinolin-7-yl)3-iso-butyroyl-4-n-propoxybenzamide $^1$H NMR (CDCl$_3$) δ: 1.08 (3H, t), 1.17 (6H, d), 1.30 (6H, s), 1.89 (2H, m), 2.40 (2H, s), 2.41 (3H, s), 3.53 (3H, m), 4.08 (2H, t), 7.03 (1H, d), 7.33 (3H, m) 7.86 (1H, s), 7.97 (1H, d), 8.07 (1H, dd); $^m/_z$ (API$^+$): 423.6 (MH$^+$; 100%)

EXAMPLE 124

N-(4,4-Dimethyl-1,2,3,4-tetrahydroisoquinolin-7-yl)-3-acetyl-4-ethoxybenzamide

Prepared from D46 and P17 in a manner similar to that described in Examples 1 and 6.

$^1$H NMR (250 MHz, CDCl$_3$) δ: 1.27 (6H, s), 1.53 (3H, t, J=7 Hz), 1.74 (1H, br), 2.68 (3H, s), 2.86 (2H, s), 4.01 (2H, s), 4.23 (2H, q, J=7 Hz), 7.06 (1H, d, J=8 Hz), 7.25–7.40 (3H, m), 7.90 (1H, br), 8.05–8.20 (2H, m); $^m/_z$ (API$^+$): 367.3 (MH$^+$; 100%).

EXAMPLE 125

N-(8-Bromo-4,4-dimethyl-1,2,3,4-tetrahydroisoquinolin-7-yl)-4-methoxy-3-trifluoromethylbenzamide $^1$H NMR (CDCl$_3$) δ: 1.29 (6H, s), 2.84 (2H, s), 4.00 (3H, s), 4.01 (2H, s), 7.12 (1H, d), 7.38 (1H, d), 8.10 (1H, dd), 8.18 (1H, d), 8.29 (1H, d), 8.37 (1H, s); $^m/_z$ (API$^+$): 457.1 (M$^+$, 100%).

EXAMPLE 126

N-(4,4,8-Trimethyl-1,2,3,4-tetrahydroisoquinolin-7-yl)-4-methoxy-3-trifluoromethylbenzamide $^1$H NMR (CDCl$_3$) δ: 1.28 (6H, s), 2.10 (3H, s), 2.83 (2H, s), 3.96 (2H, s), 3.99 (3H, s), 7.10 (1H, d), 7.26 (1H, d), 7.42 (1H, d), 7.51 (1H, s), 8.08 (2H, m); $^m/_z$ (API$^+$): 393.2 (MH$^+$; 100%).

EXAMPLE 127

N-(4,4,8-Trimethyl-1,2,3,4-tetrahydroisoquinolin-7-yl)-3-bromo-4-ethoxybenzamide $^1$H NMR (CDCl$_3$) δ: 1.28 (6H, s), 1.49 (3H, t), 2.10 (3H, t), 2.83 (2H, s), 3.96 (2H, s), 4.18 (2H, q), 6.95 (1H, d), 7.25 (1H, d), 7.42 (1H, d), 7.47 (1H, s), 7.82 (1H, dd), 8.08 (1H, d); $^m/_z$ (API$^+$): 417.6 (M$^+$; 20%).

EXAMPLE 128

N-(4,4-Dimethyl-8-ethyl-1,2,3,4-tetrahydroisoquinolin-7-yl)-4-methoxy-3-trifluoromethylbenzamide $^1$H NMR (CDCl$_3$) δ: 1.17 (3H, t), 1.29 (6H, s), 2.58 (2H, q), 2.83 (2H, s), 3.99 (3H, s), 4.05 (2H, s), 7.11 (1H, d), 7.27 (1H, d), 7.57 (2H, m), 8.06 (2H, m); $^m/_z$ (API$^+$): 407.4 (MH$^+$: 80%).

EXAMPLE 129

N-(4,4-Dimethyl-8-ethyl-1,2,3,4-tetrahydroisoquinolin-7-yl)-3-bromo-4-ethoxybenzamide $^1$H NMR (CDCl$_3$) δ: 1.16 (3H, t), 1.29 (6H, s), 1.52 (3H, t), 2.57 (2H, q), 2.83 (2H, s), 4.05 (2H, s), 4.18 (2H, q), 6.96 (1H, d), 7.27 (1H, d), 7.48 (1H, s), 7.58 (1H, d), 7.79 (1H, dd), 8.07 (1H, d); $^m/_z$ (API$^+$): 431.2 (M$^+$; 97%).

EXAMPLE 130

N-(4,4-Dimethyl-8-ethyl-1,2,3,4-tetrahydroisoquinolin-7-yl)-3-chloro-4-ethoxybenzamide $^1$H NMR (CDCl$_3$) δ: 1.16 (3H, t), 1.28 (6H, s), 1.52 (3H, t), 2.57 (2H, q), 2.83 (2H, s), 4.04 (2H, s), 4.19 (2H, q), 6.99 (1H, d), 7.27 (1H, d), 7.49 (1H, s), 7.59 (1H, d), 7.74 (1H, dd), 7.90 (1H, d); $^m/_z$ (API$^+$): 387.3 (MH$^+$; 100%).

EXAMPLE 131

N-(8-Cyano-2,4,4-trimethyl-1,2,3,4-tetrahydroisoquinolin-7-yl)-4-methoxy-3-trifluoromethylbenzamide Prepared from E116 in a manner similar to that of Procedure 5a.

$^1$H NMR (CDCl$_3$) δ: 1.31 (6H, s), 2.42 (2H, s) 2.48 (3H, s), 3.70 (2H, s), 4.00 (3H, s), 7.12 (1H, d), 7.59 (1H, d), 8.06 (1H, dd), 8.21 (2H. m) 8.30 (1H, d); $^m/_z$ (API$^+$): 418.2 (MH$^+$; 100%).

EXAMPLE 132

N-(4,4-Dimethyl-1,2,3,4-tetrahydroisoquinolin-7-yl)-3-chloro-4-methoxybenzamide Hydrochloride $^1$H NMR [free base] (250 MHz. CDCl$_3$) δ: 1.29 (6H, s). 2.86 (2H, s), 3.95 (3H, s), 4.00(2H, s), 6.98 (1H, d, J=8 Hz), 7.29–7.40 (3H, m), 7.69 (1H, brs), 7.79 (1H, dd, J=8, 2 Hz), 7.88 (1H, d, J=2 Hz); $^m/_z$ (API$^+$): 345.1 (MH$^+$; 100%).

EXAMPLE 133

N-(4,4,8-Trimethyl-1,2,3,4-tetrahydroisoquinolin-7-yl)-3-acetyl-4-ethoxybenzamide $^1$H NMR (CDCl$_3$) δ: 1.28 (6H, s), 1.54 (3H, t), 2.07 (3H, s), 2.67 (3H, s), 2.83 (2H, s), 3.95 (2H, s), 4.23 (2H, q), 7.06 (1H, q), 7.24 (1H, d), 7.37 (1H, m), 7.79 (1H, s), 8.14 (1H, dd), 8.23 (1H, d); $^m/_z$ (API$^+$): 381.2 (MH$^+$; 35%).

EXAMPLE 134

N-(4,4-Dimethyl-8-ethyl-1,2,3,4-tetrahydroisoquinolin-7-yl)-3-acetyl-4-ethoxybenzamide $^1$H NMR (CDCl$_3$) δ: 1.14 (3H, t), 1.28 (6H, s), 1.53 (3H, t), 2.56 (2H, q), 2.66 (3H, s), 2.82 (2H, s), 4.03 (2H, s), 4.23 (2H, q), 7.06 (1H, d), 7.25 (1H, d), 7.52 (1H, d), 7.82 (1H, s), 8.12 (1H, dd), 8.22 (1H, d); $^m/_z$ (API$^+$): 395.2 (MH$^+$; 100%).

EXAMPLE 135

N-(4,4-Dimethyl-8-ethyl-1,2,3,4-tetrahydroisoquinolin-7-yl)-3-acetyl-4-methoxybenzamide $^1$H NMR (CDCl$_3$) δ: 1.15 (3H, t), 1.29 (6H, s), 2.57 (2H, q), 2.65 (3H, s), 4.00 (3H, s), 7.10 (1H, d), 7.25 (1H, d), 7.55 (1H, d), 7.73 (1H, s), 8.14 (1H, dd), 8.21 (1H, d); $^m/_z$ (API$^+$): 381.3 (MH$^+$; 100%).

EXAMPLE 136

N-(4,4-Dimethyl-8-ethyl-1,2,3,4-tetrahydroisoquinolin-7-yl)-4-methoxy-3-propionyl Benzamide $^1$H NMR (CDCl$_3$) δ: 1.19 (6H, m), 1.29 (6H, s), 2.57 (2H, q), 3.04 (2H, q), 3.99 (3H, s), 7.09 (1H, d), 7.26 (1H, d), 7.57

EXAMPLE 137

N-(8-Chloro-4,4-dimethyl-1,2,3,4-tetrahydroisoquinolin-7-yl)-4-methoxy-3-trifluoromethylbenzamide $^1$H NMR (250 MHz, CDCl$_3$) δ: 1.29 (6H, s), 2.84 (2H, s), 4.00 (3H, s), 4.05 (2H, s), 7.12 (1H, d, J=8 Hz), 7.34 (1H, d, J=8 Hz), 8.06 (1H, m), 8.15 (1H, d, J=2 Hz), 8.26 (1H, brs), 8.30 (1H, d, J=8 Hz); $^m/_z$ (API$^+$): 413.1 (MH$^+$; 100%).

EXAMPLE 138

N-(8-Bromo-2,3,3-trimethyl-1,2,3,4-tetrahydroisoquinolin-7-yl)4-methoxy-3-trifluoromethyl Benzamide $^1$H NMR (250 MHz, CDCl$_3$) δ: 1.03 (6H, s), 2.44 (3H, s), 2.73 (2H, s), 3.72 (2H, s), 4.00 (3H, s), 7.08 (2H, m), 8.10 (1H, dd, J=8, 2 Hz), 8.17 (1H, s), 8.24 (1H, d, J=8 Hz), 8.36 (1H, brs); $^m/_z$ (API$^+$): 473.0, 471.1 (MH$^+$; 100%).

EXAMPLE 139

N-(8-Chloro-2,3,3-trimethyl-1,2,3,4-tetrahydroisoquinolin-7-yl)-3-chloro-4-ethoxy Benzamide $^1$H NMR (250 MHz, CDCl$_3$) δ: 1.09 (6H, s), 1.52 (3H, t, J=7 Hz), 2.43 (3H, s), 2.71 (2H, s), 3.73 (2H, s), 4.19 (2H, q, J=7 Hz), 7.00 (1H, d, J=8 Hz), 7.06 (1H, d, J=8 Hz), 7.78 (1H, dd, J=8, 2 Hz), 7.95 (1H, d, J=2 Hz), 8.26 (1H, d, J=8 Hz), 8.28 (1H, brs); $^m/_z$ (API$^+$): 407.0 (MH$^+$; 100%).

EXAMPLE 140

N-(8-Chloro-2,3,3-trimethyl-1,2,3,4-tetrahydroisoquinolin-7-yl)-3-chloro-4-methoxy Benzamide $^1$H NMR (250 MHz, CDCl$_3$) δ: 1.10 (6H, s), 2.44 (3H, s), 2.72 (2H, s), 3.74 (2H, s), 3.98 (3H, s), 7.04 (2H, t, J=8 Hz), 7.81 (1H, dd, J=8, 2 Hz), 7.95 (1H, d, J=2 Hz), 8.20–8.32 (2H, m); $^m/_z$ (API$^+$): 393 (MH$^+$; 100%).

EXAMPLE 141

N-(8-Chloro-2,3,3-trimethyl-1,2,3,4-tetrahydroisoquinolin-7-yl)-3-fluoro-4-methoxy Benzamide $^1$H NMR (250 MHz, CDCl$_3$) δ: 1.09 (6H, s), 2.43 (3H, s), 2.72 (2H, s), 3.73 (2H, s), 3.97 (3H, s), 7.05 (2H, m), 7.68 (2H, m), 8.27 (1H, d, J=8 Hz), 8.30 (1H, s); $^m/_z$ (API$^+$): 377.4 (MH$^+$; 100%).

EXAMPLE 142

N-(8-Chloro-3,3-dimethyl-1,2,3,4-tetrahydroisoquinolin-7-yl)-4-methoxy-3-trifluoromethyl Benzamide $^m/_z$ (API$^+$): 413 (MH$^+$; 100%; C$_{20}$H$_{20}$ClF$_3$N$_2$O$_2$ requires M$^+$ 412).

EXAMPLE 143

N-(5-Iodo-1,1,2-trimethyl-1,2,3,4-tetrahydroisoquinolin-7-yl)-4-methoxy-3-trifluoromethyl Benzamide The title compound was prepared by reduction of D25 in a manner similar to that of Description 27 followed by treatment similar to Example 1.

$^m/_z$(API$^+$): 519 (MH$^+$, 80%; C$_{21}$H$_{22}$F$_3$IN$_2$O$_2$ requires M$^+$ 518).

EXAMPLE 144

N-(5-Cyano-1,1,2-trimethyl-1,2,3,4-tetrahydroisoquinolin-7-yl)-4-methoxy-3-trifluoromethyl Benzamide Prepared from E143 and copper(I)cyanide according to Procedure 5a.

$^m/_z$(API$^+$): 418 (MH$^+$, 100%; C$_{22}$H$_{22}$F$_3$N$_3$O$_2$ requires M$^+$ 417).

EXAMPLE 145

N-(8-Bromo-3,3-dimethyl-1,2,3,4-tetrahydroisoquinolin-7-yl )-4-methoxy-3-trifluoromethylbenzamide $^1$H NMR (CDCl$_3$) δ: 1.20 (6H, s), 2.66 (2H, s), 4.00 (3H, s), 4.02 (2H, s), 7.11 (1H, t), 8.10 (1H, dd), 8.18 (1H, d), 8.26 (1H, d), 8.38(1H, s); m/z (API$^+$): 457.0 (M$^+$; 90%)

EXAMPLE 146

N-(1,1,2,5-Tetramethyl-1,2,3,4-tetrahydroisoquinolin-7-yl)-3-bromo-4-ethoxybenzamide Hydrochloride $^m/_z$ (API$^+$): 431, 433 (MH$^+$, 90%; C$_{22}$H$_{27}$BrN$_2$O$_2$ requires M$^+$ 431).

EXAMPLE 147

N-[4,4-Dimethyl-2-(2-methoxyethyl)-1,2,3,4-tetrahydroisoquinolin-7-yl]-3-bromo-4-iso-propoxybenzamide Hydrochloride $^m/_z$(API$^+$): 475, 477 (MH$^+$, 100%; C$_{24}$H$_{31}$BrN$_2$O$_3$ requires M$^+$ 475).

EXAMPLE 148

N-(6-Bromo-2,4,4-trimethyl-1,2,3,4-tetrahydroisoquinolin-7-yl)-3-bromo-4-ethoxybenzamide $^m/_z$(API$^+$): 499.0 (55%), 497.0 (100%), 495.0 (60%) (MH$^+$; C$_{21}$H$_{24}$Br$_2$N$_2$O$_2$ requires M$^+$ 496.2).

PHARMACOLOGICAL DATA

1. Binding Assay Method

WO 92/22293 (SmithKline Beecham) discloses compounds having anti-convulsant activity, including inter alia the compound trans-(+)-6-acetyl-4S-(4-fluorobenzoylamino)-3,4-dihydro-2,2-dimethyl-2H-1-benzopyran-3R-ol (hereinafter referred to as Compound A). It has been found that the compounds of WO 92/22293 bind to a novel receptor obtainable from rat forebrain tissue, as described in WO 96/18650 (SmithKline Beecham). The affinity of test compounds to the novel receptor site is assessed as follows.

Method

Whole forebrain tissue is obtained from rats. The tissue is first homogenised in buffer (usually 50 mM Tris/HCl, pH 7.4). The homogenised tissue is washed by centrifugation and resuspension in the same buffer, then stored at −70° C. until used.

To carry out the radioligand binding assay, aliquots of tissue prepared as above (usually at a concentration of 1–2 mg protein/ml) are mixed with aliquots of [3H]-Compound A dissolved in buffer. The final concentration of [3H]-Compound A in the mixture is usually 20 nM. The mixture is incubated at room temperature for 1 hour. [3H]-Compound A bound to the tissue is then separated from unbound [3H]-Compound A by filtration through Whatman GF/B glass fibre filters. The filters are then washed rapidly with ice-cold buffer. The amount of radioactivity bound to the tissue trapped on the filters is measured by addition of liquid scintillation cocktail to the filters followed by counting in a liquid scintillation counter.

In order to determine the amount of "specific" binding of [3H]-Compound A, parallel assays are carried out as above in which [3H]-Compound A and tissue are incubated together in the presence of unlabelled Compound A (usually 3 μM). The amount of binding of [3H]-Compound A remaining in the presence of this unlabelled compound is defined as "non-specific" binding. This amount is subtracted from the total amount of [3H]-Compound A binding (i.e. that present in the absence of unlabelled compound) to obtain the amount of "specific" binding of [3H]-Compound A to the novel site.

The affinity of the binding of test compounds to the novel site can be estimated by incubating together [3H]-Compound A and tissue in the presence of a range of concentrations of the compound to be tested. The decrease in the level of specific [3H]-Compound A binding as a result of competition by increasing concentrations of the compound under test is plotted graphically, and non-linear regression analysis of the resultant curve is used to provide an estimate of compound affinity in terms of pKi value.

Results

Compounds of this invention were active (pKi>5.5) in this test. For example E5, E11, E12, E14–E18, E20–E22, E24, E29–E31, E34, E36–E38, E40–E41, E43–69, E72, E74–E82, E84–E91, E93, E97, E101–E103 showed a pKi>7.5

2. MEST Test

The maximal electroshock seizure (MEST) threshold test in rodents is particularly sensitive for detecting potential anticonvulsant properties[1]. In this model, anticonvulsant agents elevate the threshold to electrically-induced seizures whilst proconvulsants lower the seizure threshold.

Method for Mouse Model

Mice (naive male, Charles River, U.K. CD-1 strain, 25–30 g) are randomly assigned to groups of 10–20 and dosed orally or intraperitoneally at a dose volume of 10 ml/kg with various doses of compound (0.3–300 mg/kg) or vehicle. Mice are then subjected at 30 or 60 min post dose to a single electroshock (0.1 sec, 50 Hz, sine wave form) administered via corneal electrodes. The mean current and standard error required to induce a tonic seizure in 50% ($CC_{50}$) of the mice in a particular treatment group is determined by the 'up and down' method of Dixon and Mood (1948)[2]. Statistical comparisons between vehicle- and drug-treated groups are made using the method of Litchfield and Wilcoxon (1949)[3].

In control animals the $CC_{50}$ is usually 14–18 mA. Hence the first animal in the control group is subjected to a current of 16 mA. If a tonic seizure does not ensue, the current is increased for a subsequent mouse. If a tonic convulsion does occur, then the current is decreased, and so on until all the animals in the group have been tested.

Studies are carried out using a Hugo Sachs Electronik Constant Current Shock Generator with totally variable control of shock level from 0 to 300 mA and steps of 2 mA are usually used.

Method for Rat Model

The threshold for maximal (tonic hindlimb extension) electroshock seizures in male rats (Sprague Dawley, 80–150 g, 6 weeks old) was determined by a Hugo Sachs Electronik stimulator which delivered a constant current (0.3 sec duration; from 1–300 mA in steps of 5–20 mA). The procedure is similar to that outlined above for mouse and full details are as published by Upton et al,.[4]

The percentage increase or decrease in $CC_{50}$ for each group compared to the control is calculated.

Drugs are suspended in 1% methyl cellulose.

Results

Examples showed significant activity (p<0.05) when tested at a dose of 2 mg/kg p.o. For example, the compounds E15 [263%], E17 [314%], E29 [310%], E34 [280%], E48 [240%], E69 [340%] showed increases [% increases in seizure threshold] respectively at 2 mg/kg p.o. at 2 h post-dose

REFERENCES

1. Loscher, W. and Schmidt, D. (1988). Epilepsy Res., 2, 145–181
2. Dixon, W. J. and Mood, A. M. (1948). J. Amer. Stat. Assn., 43, 109–126
3. Litchfield, J. T. and Wilcoxon, F. (1949). J. Pharmacol. exp. Ther., 96, 99–113
4. N. Upton, T. P. Blackburn, C. A. Campbell, D. Cooper, M. L. Evans, H. J. Herdon, P. D. King, A. M. Ray, T. O. Stean, W. N. Chan, J. M. Evans and M.Thompson. (1997). B. J. Pharmacol., 121, 1679–1686

What is claimed is:

1. A method of treatment of epilepsy, post-traumatic epilepsy, migraine, trigeminal neuralgia, neuropathic pain, and cancer pain comprising administering to the sufferer in need thereof an effective amount of a compound of formula (I) or pharmaceutically acceptable salts thereof or solvates thereof:

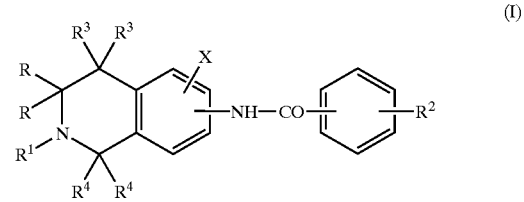

(I)

wherein:

$R^1$ is hydrogen, $C_{1-6}$ alkyl (optionally substituted by hydroxy or $C_{1-4}$alkoxy), $C_{1-6}$alkenyl, $C_{1-6}$alkynyl, $C_{1-6}$alkylCO—, formyl, $CF_3CO$— or $C_{1-6}$alkyl$SO_2$—;

$R^2$ is hydrogen or up to three substituents selected from halogen, $NO_2$, $CN$, $N_3$, $CF_3O$—, $CF_3S$—, $CF_3CO$—, $CF_3SO_2$, trifluoromethyldiazirinyl, $C_{1-6}$alkyl, $C_{1-6}$alkenyl, $C_{1-6}$alkynyl, $C_{1-6}$perfluoroalkyl, $C_{3-6}$cycloalkyl, $C_{3-6}$cycloalkyl-$C_{1-4}$alkyl-, $C_{1-6}$alkylO—, $C_{1-6}$alkylCO—, $C_{3-6}$cycloalkylO—, $C_{3-6}$cycloalkylCO—, $C_{3-6}$cycloalkyl-$C_{1-4}$alkylO—, $C_{3-6}$cycloalkyl-$C_{1-4}$alkylCO—, phenyl, phenoxy, benzyloxy, benzoyl, phenyl-$C_{1-4}$alkyl-, $C_{1-6}$alkylS—, $C_{1-6}$alkylSO$_2$—, $(C_{1-4}$alkyl$)_2$NSO$_2$—, $(C_{1-4}$alkyl)NHSO$_2$—, $(C_{1-4}$alkyl$)_2$NCO—, $(C_{1-4}$alkyl)NHCO— and $CONH_2$; or —$NR^5R^6$ where $R^5$ is hydrogen or $C_{1-4}$ alkyl, and $R^6$ is hydrogen, $C_{1-4}$alkyl, formyl, —$CO_2C_{1-4}$alkyl or —$COC_{1-4}$alkyl; or two R groups together form a carbocyclic ring that is saturated or unsaturated and unsubstituted or substituted by —OH or =O;

the two R groups, the two $R^3$ groups and the two $R^4$ groups are each independently hydrogen, $C_{1-6}$ alkyl, $C_{1-6}$ alkenyl, benzyl, or phenyl, or the two R groups and/or the two $R^3$ groups and/or the two $R^4$ groups together form a $C_{3-6}$ spiroalkyl group, provided that at least one R, $R^3$ or $R^4$ group is other than hydrogen; and X is selected from the group consisting of hydrogen, halogen, cyano, $CF_3$, alkyl, and alkoxy; provided that when X is hydrogen, the two R groups are not both hydrogen.

2. The method according to claim 1 wherein the compound of formula (I) has

R as methyl or hydrogen; and/or $R^1$ as hydrogen or methyl; and/or $R^2$ as methyl, ethyl, iso-propyl, methoxy, ethoxy, iso-propoxy, bromo, chloro, fluoro, iodo, cyano, acetyl, $CF_3$, or $C_2F_5$; and/or $R^3$ as hydrogen, methyl, or spirocyclobutyl; and/or $R^4$ as hydrogen, methyl, benzyl, allyl, phenyl, iso-butyl, or iso-propyl.

3. The method according to claim 1 wherein the compound of formula (I) is selected from the list consisting of:

N-(3,3-Dimethyl-1,2,3,4-tetrahydro-2-trifluoroacetyl-isoquinolin-7-yl)-4-methoxy-3-trifluoromethylbenzamide;

N-(3,3-Dimethyl-1,2,3,4-tetrahydro-2-trifluoroacetyl-isoquinolin-7-yl)-3-cyano-4-iso-propylbenzamide;

N-(3,3-Dimethyl-1,2,3,4-tetrahydro-2-trifluoroacetylisoquinolin-7-yl)-3-chloro-4-iso-propyloxybenzamide;

N-(3,3-Dimethyl-1,2,3,4-tetrahydro-2-trifluoroacetylisoquinolin-7-yl)-3-bromo-4-ethoxybenzamide;

N-(3,3-Dimethyl-1,2,3,4-tetrahydro-2-trifluoroacetylisoquinolin-7-yl)-3-bromo-4-iso-propyloxybenzamide;

N-(3,3-Dimethyl-1,2,3,4-tetrahydroisoquinolin-7-yl)-4-methoxy-3-trifluoromethylbenzamide;

N-(3,3-Dimethyl-1,2,3,4-tetrahydroisoquinolin-7-yl)-3-cyano-4-iso-propylbenzamide;

N-(3,3-Dimethyl-1,2,3,4-tetrahydroisoquinolin-7-yl)-3-chloro-4-iso-propyloxy-benzamide;

N-(3,3-Dimethyl-1,2,3,4-tetrahydroisoquinolin-7-yl)-3-bromo-4-ethoxybenzamide;

N-(3,3-Dimethyl-1,2,3,4-tetrahydroisoquinolin-7-yl)-3-bromo-4-iso-propyloxybenzamide;

N-(8-Ethyl-2,4,4-trimethyl-1,2,3,4-tetrahydroisoquinolin-7-yl)-3-bromo-4-ethoxybenzamide;

N-(8-Ethyl-2,4,4-trimethyl-1,2,3,4-tetrahydroisoquinolin-7-yl)-4-methoxy-3-trifluoromethylbenzamide;

N-(8-Ethyl-2,4,4-trimethyl-1,2,3,4-tetrahydroisoquinolin-7-yl)-3-bromo-4-iso-propyloxybenzamide;

N-(8-Ethyl-2,4,4-trimethyl-1,2,3,4-tetrahydroisoquinolin-7-yl)-3-cyano-4-iso-propylbenzamide;

N-(8-Ethyl-2,4,4-trimethyl-1,2,3,4-tetrahydroisoquinolin-7-yl)-3-acetyl-4-iso-propyloxybenzamide;

N-(5-Chloro-1,1,2-trimethyl-1,2,3,4-tetrahydroisoquinolin-7-yl)-3-bromo-4-ethyl benzamide;

N-(5-Chloro-1,1,2-trimethyl-1,2,3,4-tetrahydroisoquinolin-7-yl)-3-cyano-4-iso-propylbenzamide;

N-(5-Chloro-1,1,2-trimethyl-1,2,3,4-tetrahydroisoquinolin-7-yl)-4-methoxy-3-trifluoromethylbenzamide;

N-(5-Chloro-1,1,2-trimethyl-1,2,3,4-tetrahydroisoquinolin-7-yl)-3-bromo-4-ethoxybenzamide;

N-(2,3,3-Trimethyl-1,2,3,4-tetrahydroisoquinolin-7-yl)-4-methoxy-3-trifluoromethylbenzamide;

N-(2,3,3-Trimethyl-1,2,3,4-tetrahydroisoquinolin-7-yl)-3-cyano-4-iso-propylbenzamide;

N-(2,3,3-Trimethyl-1,2,3,4-tetrahydroisoquinolin-7-yl)-3-bromo-4-ethylbenzamide;

N-(2,3,3-Trimethyl-1,2,3,4-tetrahydroisoquinolin-7-yl)-3-bromo-4-ethoxybenzamide;

N-(2,3,3-Trimethyl-1,2,3,4-tetrahydroisoquinolin-7-yl)-3-chloro-4-iso-propoxybenzamide;

N-(1,1,2,5-Tetramethyl-1,2,3,4-tetrahydroisoquinolin-7-yl)-3-bromo-4-ethylbenzamide;

N-(1,1,2,5-Tetramethyl-1,2,3,4-tetrahydroisoquinolin-7-yl)-3-cyano-4-iso-propylbenzamide;

N-(1,1,2,5-Tetramethyl-1,2,3,4-tetrahydroisoquinolin-7-yl)-4-methoxy-3-trifluoromethylbenzamide;

N-(1,1,2-Trimethyl-5-trifluoromethyl-1,2,3,4-tetrahydroisoquinolin-7-yl)-4-methoxy-3-trifluoromethylbenzamide;

N-(1,1,2-Trimethyl-5-trifluoromethyl-1,2,3,4-tetrahydroisoquinolin-7-yl)-3-bromo-4-ethoxybenzamide;

N-(1,1,2-Trimethyl-5-trifluoromethyl-1,2,3,4-tetrahydroisoquinolin-7-yl)-3-cyano-4-ethoxybenzamide;

N-(8-Chloro-2,4,4-trimethyl-1,2,3,4-tetrahydroisoquinolin-7-yl)-3-bromo-4-iso-propoxybenzamide;

N-(8-Chloro-2,4,4-trimethyl-1,2,3,4-tetrahydroisoquinolin-7-yl)-4-ethyl-3-trifluoromethylbenzamide;

N-(8-Chloro-2,4,4-trimethyl-1,2,3,4-tetrahydroisoquinolin-7-yl)-3-acetyl-4-iso-propylbenzamide;

N-(8-Chloro-2,4,4-trimethyl-1,2,3,4-tetrahydroisoquinolin-7-yl)-3-cyano-4-methoxybenzamide;

N-(8-Chloro-2,4,4-trimethyl-1,2,3,4-tetrahydroisoquinolin-7-yl)-4-methoxy-3-trifluoromethylbenzamide;

N-(8-Chloro-2,4,4-trimethyl-1,2,3,4-tetrahydroisoquinolin-7-yl)-3-chloro-4-ethoxybenzamide;

N-(8-Chloro-2,4,4-trimethyl-1,2,3,4-tetrahydroisoquinolin-7-yl)-3-bromo-4-ethoxybenzamide;

N-(8-Chloro-2,4,4-trimethyl-1,2,3,4-tetrahydroisoquinolin-7-yl)-3-bromo-4-iso-propylbenzamide;

N-(8-Chloro-2,4,4-trimethyl-1,2,3,4-tetrahydroisoquinolin-7-yl)-3-cyano-4-ethylbenzamide;

N-(8-Ethyl-2,4,4-trimethyl-1,2,3,4-tetrahydroisoquinolin-7-yl)-3-bromo-4-methoxybenzamide;

N-(8-Ethyl-2,4,4-trimethyl-1,2,3,4-tetrahydroisoquinolin-7-yl)-3-chloro-4-methoxybenzamide;

N-(8-Ethyl-2,4,4-trimethyl-1,2,3,4-tetrahydroisoquinolin-7-yl)-3-chloro-4-ethoxybenzamide;
N-(8-Ethyl-2,4,4-trimethyl-1,2,3,4-tetrahydroisoquinolin-7-yl)-3-bromo-4-ethylbenzamide;
N-(8-Methyl-2,4,4-trimethyl-1,2,3,4-tetrahydroisoquinolin-7-yl)-3-bromo-4-ethoxybenzamide;
N-(8-Methyl-2,4,4-trimethyl-1,2,3,4-tetrahydroisoquinolin-7-yl)-4-methoxy-3-trifluoromethylbenzamide;
N-(8-Methyl-2,4,4-trimethyl-1,2,3,4-tetrahydroisoquinolin-7-yl)-3-chloro-4-ethoxybenzamide;
N-(8-Methyl-2,4,4-trimethyl-1,2,3,4-tetrahydroisoquinolin-7-yl)-3-cyano-4-ethylbenzamide;
N-(8-Bromo-2,4,4-trimethyl-1,2,3,4-tetrahydroisoquinolin-7-yl)-3-bromo-4-methoxybenzamide;
N-(8-Bromo-2,4,4-trimethyl-1,2,3,4-tetrahydroisoquinolin-7-yl)-4-methoxy-3-trifluoromethylbenzamide;
N-(8-Bromo-4,4-dimethyl-1,2,3,4-tetrahydroisoquinolin-7-yl)-4-methoxy-3-trifluoromethylbenzamide;
N-(4,4,8-Trimethyl-1,2,3,4-tetrahydroisoquinolin-7-yl)-4-methoxy-3-trifluoromethylbenzamide;
N-(4,4,8-Trimethyl-1,2,3,4-tetrahydroisoquinolin-7-yl)-3-bromo-4-ethoxybenzamide;
N-(4,4-Dimethyl-8-ethyl-1,2,3,4-tetrahydroisoquinolin-7-yl)-4-methoxy-3-trifluoromethylbenzamide;
N-(4,4-Dimethyl-8-ethyl-1,2,3,4-tetrahydroisoquinolin-7-yl)-3-bromo-4-ethoxybenzamide;
N-(4,4-Dimethyl-8-ethyl-1,2,3,4-tetrahydroisoquinolin-7-yl)-3-chloro-4-ethoxybenzamide;
N-(8-Cyano-2,4,4-trimethyl-1,2,3,4-tetrahydroisoquinolin-7-yl)-4-methoxy-3-trifluoromethylbenzamide;
N-(4,4,8-Trimethyl-1,2,3,4-tetrahydroisoquinolin-7-yl)-3-acetyl-4-ethoxybenzamide;
N-(4,4-Dimethyl-8-ethyl-1,2,3,4-tetrahydroisoquinolin-7-yl)-3-acetyl-4-ethoxybenzamide;
N-(4,4-Dimethyl-8-ethyl-1,2,3,4-tetrahydroisoquinolin-7-yl)-3-acetyl-4-methoxybenzamide;
N-(4,4-Dimethyl-8-ethyl-1,2,3,4-tetrahydroisoquinolin-7-yl)-4-methoxy-3-propionyl benzamide;
N-(8-Chloro-4,4-dimethyl-1,2,3,4-tetrahydroisoquinolin-7-yl)-4-methoxy-3-trifluoromethylbenzamide;
N-(8-Bromo-2,3,3-trimethyl-1,2,3,4-tetrahydroisoquinolin-7-yl)-4-methoxy-3-trifluoromethyl benzamide;
N-(8-Chloro-2,3,3-trimethyl-1,2,3,4-tetrahydroisoquinolin-7-yl)-3-fluoro-4-ethoxy benzamide;
N-(8-Chloro-2,3,3-trimethyl-1,2,3,4-tetrahydroisoquinolin-7-yl)-3-chloro-4-methoxy benzamide;
N-(8-Chloro-2,3,3-trimethyl-1,2,3,4-tetrahydroisoquinolin-7-yl)-3-fluoro-4-methoxy benzamide;
N-(8-Chloro-3,3-dimethyl-1,2,3,4-tetrahydroisoquinolin-7-yl)-4-methoxy-3-trifluoromethyl benzamide;
N-(5-Iodo-1,1,2-trimethyl-1,2,3,4-tetrahydroisoquinolin-7-yl)-4-methoxy-3-trifluoromethyl benzamide;
N-(5-Cyano-1,1,2-trimethyl-1,2,3,4-tetrahydroisoquinolin-7-yl)-4-methoxy-3-trifluoromethyl benzamide;
N-(8-Bromo-3,3-dimethyl-1,2,3,4-tetrahydroisoquinolin-7-yl)-4-methoxy-3-trifluoromethylbenzamide;
N-(1,1,2,5-Tetramethyl-1,2,3,4-tetrahydroisoquinolin-7-yl)-3-bromo-4-ethoxybenzamide; and;
N-(6Bromo-2,4,4-trimethyl-1,2,3,4-tetrahydroisoquinolin-7-yl)-3-bromo-4-ethoxybenzamide.

4. A compound selected from the list consisting of:
N-(3,3-Dimethyl-1,2,3,4-tetrahydro-2-trifluoroacetyl-isoquinolin-7-yl)-4-methoxy-3-trifluoromethylbenzamide;
N-(3,3-Dimethyl-1,2,3,4-tetrahydro-2-trifluoroacetyl-isoquinolin-7-yl)-3-cyano-4-iso-propylbenzamide;
N-(3,3-Dimethyl-1,2,3,4-tetrahydro-2-trifluoroacetylisoquinolin-7-yl)-3-chloro-4-iso-propyloxybenzamide;
N-(3,3-Dimethyl-1,2,3,4-tetrahydro-2-trifluoroacetylisoquinolin-7-yl)-3-bromo-4-ethoxybenzamide;
N-(3,3-Dimethyl-1,2,3,4-tetrahydro-2-trifluoroacetylisoquinolin-7-yl)-3-bromo-4-iso-propyloxybenzamide;
N-(3,3-Dimethyl-1,2,3,4-tetrahydroisoquinolin-7-yl)-4-methoxy-3-trifluoromethylbenzamide;
N-(3,3-Dimethyl-1,2,3,4-tetrahydroisoquinolin-7-yl)-3-cyano-4-iso-propylbenzamide;
N-(3,3-Dimethyl-1,2,3,4-tetrahydroisoquinolin-7-yl)-3-chloro-4-iso-propyloxy-benzamide;
N-(3,3-Dimethyl-1,2,3,4-tetrahydroisoquinolin-7-yl)-3-bromo-4-ethoxybenzamide;
N-(3,3-Dimethyl-1,2,3,4-tetrahydroisoquinolin-7-yl)-3-bromo-4-iso-propyloxybenzamide;
N-(8-Ethyl-2,4,4-trimethyl-1,2,3,4-tetrahydroisoquinolin-7-yl)-3-bromo-4-ethoxybenzamide;
N-(8-Ethyl-2,4,4-trimethyl-1,2,3,4-tetrahydroisoquinolin-7-yl)-4methoxy-3-trifluoromethylbenzamide;
N-(8-Ethyl-2,4,4-trimethyl-1,2,3,4-tetrahydroisoquinolin-7-yl)-3-bromo-4-iso-propyloxybenzamide;
N-(8-Ethyl-2,4,4-trimethyl-1,2,3,4-tetrahydroisoquinolin-7-yl)-3-cyano-4-iso-propylbenzamide;
N-(8-Ethyl-2,4,4-trimethyl-1,2,3,4-tetrahydroisoquinolin-7-yl)-3-acetyl-4-iso-propyloxybenzamide;
N-(5-Chloro-1,1,2-trimethyl-1,2,3,4-tetrahydroisoquinolin-7-yl)-3-bromo-4-ethyl benzamide;
N-(5-Chloro-1,1,2-trimethyl-1,2,3,4-tetrahydroisoquinolin-7-yl)-3-cyano-4-iso-propylbenzamide;
N-(5-Chloro-1,1,2-trimethyl-1,2,3,4-tetrahydroisoquinolin-7-yl)-4-methoxy-3-trifluoromethylbenzamide;
N-(5-Chloro-1,1,2-trimethyl-1,2,3,4-tetrahydroisoquinolin-7-yl)-3-bromo-4-ethoxybenzamide;

N-(2,3,3-Trimethyl-1,2,3,4-tetrahydroisoquinolin-7-yl)-4-methoxy-3-trifluoromethylbenzamide;

N-(2,3,3-Trimethyl-1,2,3,4-tetrahydroisoquinolin-7-yl)-3-cyano-4-iso-propylbenzamide;

N-(2,3,3-Trimethyl-1,2,3,4-tetrahydroisoquinolin-7-yl)-3-bromo-4-ethylbenzamide;

N-(2,3,3-Trimethyl-1,2,3,4-tetrahydroisoquinolin-7-yl)-3-bromo-4-ethoxybenzamide;

N-(2,3,3-Trimethyl-1,2,3,4-tetrahydroisoquinolin-7-yl)-3-chloro-4-iso-propoxybenzamide;

N-(1,1,2,5-Tetramethyl-1,2,3,4-tetrahydroisoquinolin-7-yl)-3-bromo-4-ethylbenzamide;

N-(1,1,2,5-Tetramethyl-1,2,3,4-tetrahydroisoquinolin-7-yl)-3-cyano-4-iso-propylbenzamide;

N-(1,1,2,5-Tetramethyl-1,2,3,4-tetrahydroisoquinolin-7-yl)-4-methoxy-3-trifluoromethylbenzamide;

N-(1,1,2-Trimethyl-5-trifluoromethyl-1,2,3,4-tetrahydroisoquinolin-7-yl)-4-methoxy-3-trifluoromethylbenzamide;

N-(1,1,2-Trimethyl-5-trifluoromethyl-1,2,3,4-tetrahydroisoquinolin-7-yl)-3-bromo-4-ethoxybenzamide;

N-(1,1,2-Trimethyl-5-trifluoromethyl-1,2,3,4-tetrahydroisoquinolin-7-yl)-3-cyano-4-ethoxybenzamide;

N-(8-Chloro-2,4,4-trimethyl-1,2,3,4-tetrahydroisoquinolin-7-yl)-3-bromo-4-iso-propoxybenzamide;

N-(8-Chloro-2,4,4-trimethyl-1,2,3,4-tetrahydroisoquinolin-7-yl)-4-ethyl-3-trifluoromethylbenzamide;

N-(8-Chloro-2,4,4-trimethyl-1,2,3,4-tetrahydroisoquinolin-7-yl)-3-acetyl-4-iso-propylbenzamide;

N-(8-Chloro-2,4,4-trimethyl-1,2,3,4-tetrahydroisoquinolin-7-yl)-3-cyano-4-methoxybenzamide;

N-(8-Chloro-2,4,4-trimethyl-1,2,3,4-tetrahydroisoquinolin-7-yl)-4-methoxy-3-trifluoromethylbenzamide;

N-(8-Chloro-2,4,4-trimethyl-1,2,3,4-tetrahydroisoquinolin-7-yl)-3-chloro-4-ethoxybenzamide;

N-(8-Chloro-2,4,4-trimethyl-1,2,3,4-tetrahydroisoquinolin-7-yl)-3-bromo-4-ethoxybenzamide;

N-(8-Chloro-2,4,4-trimethyl-1,2,3,4-tetrahydroisoquinolin-7-yl)-3-bromo-4-iso-propylbenzamide;

N-(8-Chloro-2,4,4-trimethyl-1,2,3,4-tetrahydroisoquinolin-7-yl)-3-cyano-4-ethylbenzamide;

N-(8-Ethyl-2,4,4-trimethyl-1,2,3,4-tetrahydroisoquinolin-7-yl)-3-bromo-4-methoxybenzamide;

N-(8-Ethyl-2,4,4-trimethyl-1,2,3,4-tetrahydroisoquinolin-7-yl)-3-chloro-4-methoxybenzamide;

N-(8-Ethyl-2,4,4-trimethyl-1,2,3,4-tetrahydroisoquinolin-7-yl)-3-chloro-4-ethoxybenzamide;

N-(8-Ethyl-2,4,4-trimethyl-1,2,3,4-tetrahydroisoquinolin-7-yl)-3-bromo-4-ethylbenzamide;

N-(8-Methyl-2,4,4-trimethyl-1,2,3,4-tetrahydroisoquinolin-7-yl)-3-bromo-4-ethoxybenzamide;

N-(8-Methyl-2,4,4-trimethyl-1,2,3,4-tetrahydroisoquinolin-7-yl)-4-methoxy-3-trifluoromethylbenzamide;

N-(8-Methyl-2,4,4-trimethyl-1,2,3,4-tetrahydroisoquinolin-7-yl)-3-chloro-4-ethoxybenzamide;

N-(8-Methyl-2,4,4-trimethyl-1,2,3,4-tetrahydroisoquinolin-7-yl)-3-cyano-4-ethylbenzamide;

N-(8-Bromo-2,4,4-trimethyl-1,2,3,4-tetrahydroisoquinolin-7-yl)-3-bromo-4-methoxybenzamide;

N-(8-Bromo-2,4,4-trimethyl-1,2,3,4-tetrahydroisoquinolin-7-yl)-4-methoxy-3-trifluoromethylbenzamide;

N-(8-Bromo-4,4-dimethyl-1,2,3,4-tetrahydroisoquinolin-7-yl)-4-methoxy-3-trifluoromethylbenzamide;

N-(4,4,8-Trimethyl-1,2,3,4-tetrahydroisoquinolin-7-yl)-4-methoxy-3-trifluoromethylbenzamide;

N-(4,4,8-Trimethyl-1,2,3,4-tetrahydroisoquinolin-7-yl)-3-bromo-4-ethoxybenzamide;

N-(4,4-Dimethyl-8-ethyl-1,2,3,4-tetrahydroisoquinolin-7-yl)-4-methoxy-3-trifluoromethylbenzamide;

N-(4,4-Dimethyl-8-ethyl-1,2,3,4-tetrahydroisoquinolin-7-yl)-3-bromo-4-ethoxybenzamide;

N-(4,4-Dimethyl-8-ethyl-1,2,3,4-tetrahydroisoquinolin-7-yl)-3-chloro-4-ethoxybenzamide;

N-(8-Cyano-2,4,4-trimethyl-1,2,3,4-tetrahydroisoquinolin-7-yl)-4-methoxy-3-trifluoromethylbenzamide;

N-(4,4,8-Trimethyl-1,2,3,4-tetrahydroisoquinolin-7-yl)-3-acetyl-4-ethoxybenzamide;

N-(4,4-Dimethyl-8-ethyl-1,2,3,4-tetrahydroisoquinolin-7-yl)-3-acetyl-4-ethoxybenzamide;

N-(4,4-Dimethyl-8-ethyl-1,2,3,4-tetrahydroisoquinolin-7-yl)-3-acetyl-4-methoxybenzamide;

N-(4,4-Dimethyl-8-ethyl-1,2,3,4-tetrahydroisoquinolin-7-yl)-4-methoxy-3-propionyl benzamide;

N-(8-Chloro-4,4-dimethyl-1,2,3,4-tetrahydroisoquinolin-7-yl)-4-methoxy-3-trifluoromethylbenzamide;

N-(8-Bromo-2,3,3-trimethyl-1,2,3,4-tetrahydroisoquinolin-7-yl)-4-methoxy-3-trifluoromethyl benzamide;

N-(8-Chloro-2,3,3-trimethyl-1,2,3,4-tetrahydroisoquinolin-7-yl)-3-chloro-4-ethoxy benzamide;

N-(8-Chloro-2,3,3-trimethyl-1,2,3,4-tetrahydroisoquinolin-7-yl)-3-chloro-4-methoxy benzamide;

N-(8-Chloro-2,3,3-trimethyl-1,2,3,4-tetrahydroisoquinolin-7-yl)-3-fluoro-4-methoxy benzamide;

N-(8-Chloro-3,3-dimethyl-1,2,3,4-tetrahydroisoquinolin-7-yl)-4-methoxy-3-trifluoromethyl benzamide;

N-(5-Iodo-1,1,2-trimethyl-1,2,3,4-tetrahydroisoquinolin-7-yl)-4-methoxy-3-trifluoromethyl benzamide;

N-(5-Cyano-1,1,2-trimethyl-1,2,3,4-tetrahydroisoquinolin-7-yl)-4-methoxy-3-trifluoromethyl benzamide;

N-(8-Bromo-3,3-dimethyl-1,2,3,4-tetrahydroisoquinolin-7-yl)-4-methoxy-3-trifluoromethylbenzamide;

N-(1,1,2,5-Tetramethyl-1,2,3,4-tetrahydroisoquinolin-7-yl)-3-bromo-4-ethoxybenzamide; and;

N-(6-Bromo-2,4,4-trimethyl-1,2,3,4-tetrahydroisoquinolin-7-yl)-3-bromo-4-ethoxybenzamide, or a pharmaceutically acceptable salt thereof.

5. A pharmaceutical composition which comprises a compound as defined in claim 4, or a pharmaceutically acceptable salt or solvate thereof, and a pharmaceutically acceptable carrier.

6. A method of prophylaxis of migraine comprising administering to the sufferer in need thereof an effective prophylactic amount of a compound of formula (I) or pharmaceutically acceptable salts thereof or solvates thereof:

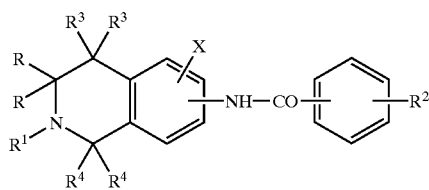

(I)

wherein:

R$^1$ is hydrogen, C$_{1-6}$ alkyl (optionally substituted by hydroxy or C$_{1-4}$alkoxy),C$_{1-6}$alkenyl, C$_{1-6}$alkynyl, C$_{1-6}$alkylCO—, formyl, CF$_3$CO— or C$_{1-6}$alkylSO$_2$—;

R$^2$ is hydrogen or up to three substituents selected from halogen, NO$_2$, CN, N$_3$, CF$_3$O—, CF$_3$S—, CF$_3$CO—, CF$_3$SO$_2$, trifluoromethyldiazirinyl, C$_{1-6}$alkyl, C$_{1-6}$alkenyl, C$_{1-6}$alkynyl, C$_{1-6}$perfluoroalkyl, C$_{3-6}$cycloalkyl, C$_{3-6}$cycloalkyl-C$_{1-4}$alkyl-, C$_{1-6}$alkylO—, C$_{1-6}$alkylCO—, C$_{3-6}$cycloalkylO—, C$_{3-6}$cycloalkylCO—, C$_{3-6}$cycloalkyl-C$_{1-4}$alkylO—, C$_{3-6}$cycloalkyl-C$_{1-4}$alkylCO—, phenyl, phenoxy, benzyloxy, benzoyl, phenyl-C$_{1-4}$alkyl-, C$_{1-6}$alkylS—; C$_{1-6}$alkylSO$_2$—; (C$_{1-4}$alkyl)$_2$NSO$_2$—,(C$_{1-4}$alkyl)NHSO$_2$—, (C$_{1-4}$alkyl)$_2$NCO—, (C$_{1-4}$alkyl)NHCO— and CONH$_2$; or —NR$^5$R$^6$ where R$^5$ is hydrogen or C$_{1-4}$ alkyl, and R$^6$ is hydrogen, C$_{1-4}$alkyl, formyl, —CO$_2$C$_{1-4}$alkyl or —COC$_{1-4}$alkyl; groups together form a carbocyclic ring that is saturated or unsaturated and unsubstituted or substituted by —OH or =O;

the two R groups, the two R$^3$ groups and the two R$^4$ groups are each independently hydrogen, C$_{1-6}$ alkyl, C$_{1-6}$ alkenyl, benzyl, or phenyl, or the two R groups and/or the two R$^3$ groups and/or the two R$^4$ groups together form a C$_{3-6}$ spiroalkyl group, provided that at least one R, R$^3$ or R$^4$ group is other than hydrogen; and X is selected from the group consisting of hydrogen, halogen, cyano, CF$_3$, alkyl, and alkoxy; provided that when X is hydrogen, the two R groups are not both hydrogen.

7. The method according to claim 6 wherein the compound of formula (I) has

R as methyl or hydrogen; and/or

R$^1$ as hydrogen or methyl; and/or

R$^2$ as methyl, ethyl, iso-propyl, methoxy, ethoxy, iso-propoxy, bromo, chloro, fluoro, iodo, cyano, acetyl, CF$_3$, or C$_2$F$_5$; and/or R$^3$ as hydrogen, methyl, or spirocyclobutyl; and/or R$^4$ as hydrogen, methyl, benzyl, allyl, phenyl, iso-butyl, or iso-propyl.

8. The method according to claim 6 wherein the compound of formula (I) is selected from the list consisting of:

N-(3,3-Dimethyl-1,2,3,4-tetrahydro-2-trifluoroacetyl-isoquinolin-7-yl)-4-methoxy-3-trifluoromethylbenzamide;

N-(3,3-Dimethyl-1,2,3,4-tetrahydro-2-trifluoroacetyl-isoquinolin-7-yl)-3-cyano-4-iso-propylbenzamide;

N-(3,3-Dimethyl-1,2,3,4-tetrahydro-2-trifluoroacetylisoquinolin-7-yl)-3-chloro-4-iso-propyloxybenzamide;

N-(3,3-Dimethyl-1,2,3,4-tetrahydro-2-trifluoroacetylisoquinolin-7-yl)-3-bromo-4-ethoxybenzamide;

N-(3,3-Dimethyl-1,2,3,4-tetrahydro-2-trifluoroacetylisoquinolin-7-yl)-3-bromo-4-iso-propyloxybenzamide;

N-(3,3-Dimethyl-1,2,3,4-tetrahydroisoquinolin-7-yl)-4-methoxy-3-trifluoromethylbenzamide;

N-(3,3-Dimethyl-1,2,3,4-tetrahydroisoquinolin-7-yl)-3-cyano-4-iso-propylbenzamide;

N-(3,3-Dimethyl-1,2,3,4-tetrahydroisoquinolin-7-yl)-3-chloro-4-iso-propyloxy-benzamide;

N-(3,3-Dimethyl-1,2,3,4-tetrahydroisoquinolin-7-yl)-3-bromo-4-ethoxybenzamide;

N-(3,3-Dimethyl-1,2,3,4-tetrahydroisoquinolin-7-yl)-3-bromo-4-iso-propyloxybenzamide;

N-(8-Ethyl-2,4,4-trimethyl-1,2,3,4-tetrahydroisoquinolin-7-yl)-3-bromo-4-ethoxybenzamide;

N-(8-Ethyl-2,4,4-trimethyl-1,2,3,4-tetrahydroisoquinolin-7-yl)-4-methoxy-3-trifluoromethylbenzamide;

N-(8-Ethyl-2,4,4-trimethyl-1,2,3,4-tetrahydroisoquinolin-7-yl)-3-bromo-4-iso-propyloxybenzamide;

N-(8-Ethyl-2,4,4-trimethyl-1,2,3,4-tetrahydroisoquinolin-7-yl)-3-cyano-4-iso-propylbenzamide;

N-(8-Ethyl-2,4,4-trimethyl-1,2,3,4-tetrahydroisoquinolin-7-yl)-3-acetyl-4-iso-propyloxybenzamide;

N-(5-Chloro-1,1,2-trimethyl-1,2,3,4-tetrahydroisoquinolin-7-yl)-3-bromo-4-ethyl benzamide;

N-(5-Chloro-1,1,2-trimethyl-1,2,3,4-tetrahydroisoquinolin-7-yl)-3-cyano-4-iso-propylbenzamide;

N-(5-Chloro-1,1,2-trimethyl-1,2,3,4-tetrahydroisoquinolin-7-yl)-4-methoxy-3-trifluoromethylbenzamide;

N-(5-Chloro-1,1,2-trimethyl-1,2,3,4-tetrahydroisoquinolin-7-yl)-3-bromo-4-ethoxybenzamide;

N-(2,3,3-Trimethyl-1,2,3,4-tetrahydroisoquinolin-7-yl)-4-methoxy-3-trifluoromethylbenzamide;

N-(2,3,3-Trimethyl-1,2,3,4-tetrahydroisoquinolin-7-yl)-3-cyano-4-iso-propylbenzamide;

N-(2,3,3-Trimethyl-1,2,3,4-tetrahydroisoquinolin-7-yl)-3-bromo-4-ethylbenzamide;

N-(2,3,3-Trimethyl-1,2,3,4-tetrahydroisoquinolin-7-yl)-3-bromo-4-ethoxybenzamide;

N-(2,3,3-Trimethyl-1,2,3,4-tetrahydroisoquinolin-7-yl)-3-chloro-4-iso-propoxybenzamide;

N-(1,1,2,5-Tetramethyl-1,2,3,4-tetrahydroisoquinolin-7-yl)-3-bromo-4-ethylbenzamide;

N-(1,1,2,5-Tetramethyl-1,2,3,4-tetrahydroisoquinolin-7-yl)-3-cyano-4-iso-propylbenzamide;

N-(1,1,2,5-Tetramethyl-1,2,3,4-tetrahydroisoquinolin-7-yl)-4-methoxy-3-trifluoromethylbenzamide;

N-(1,1,2-Trimethyl-5-trifluoromethyl-1,2,3,4-tetrahydroisoquinolin-7-yl)-4-methoxy-3-trifluoromethylbenzamide;

N-(1,1,2-Trimethyl-5-trifluoromethyl-1,2,3,4-tetrahydroisoquinolin-7-yl)-3-bromo-4-ethoxybenzamide;

N-(1,1,2-Trimethyl-5-trifluoromethyl-1,2,3,4-tetrahydroisoquinolin-7-yl)-3-cyano-4-ethoxybenzamide;

N-(8-Chloro-2,4,4-trimethyl-1,2,3,4-tetrahydroisoquinolin-7-yl)-3-bromo-4-iso-propoxybenzamide;

N-(8-Chloro-2,4,4-trimethyl-1,2,3,4-tetrahydroisoquinolin-7-yl)-4-ethyl-3-trifluoromethylbenzamide;

N-(8-Chloro-2,4,4-trimethyl-1,2,3,4-tetrahydroisoquinolin-7-yl)-3-acetyl-4-iso-propylbenzamide;

N-(8-Chloro-2,4,4-trimethyl-1,2,3,4-tetrahydroisoquinolin-7-yl)-3-cyano-4-methoxybenzamide;

N-(8-Chloro-2,4,4-trimethyl-1,2,3,4-tetrahydroisoquinolin-7-yl)-4-methoxy-3-trifluoromethylbenzamide;

N-(8-Chloro-2,4,4-trimethyl-1,2,3,4-tetrahydroisoquinolin-7-yl)-3-chloro-4-ethoxybenzamide;

N-(8-Chloro-2,4,4-trimethyl-1,2,3,4-tetrahydroisoquinolin-7-yl)-3-bromo-4-ethoxybenzamide;

N-(8-Chloro-2,4,4-trimethyl-1,2,3,4-tetrahydroisoquinolin-7-yl)-3-bromo-4-iso-propylbenzamide;

N-(8-Chloro-2,4,4-trimethyl-1,2,3,4-tetrahydroisoquinolin-7-yl)-3-cyano-4-ethylbenzamide;

N-(8-Ethyl-2,4,4-trimethyl-1,2,3,4-tetrahydroisoquinolin-7-yl)-3-bromo-4-methoxybenzamide;

N-(8-Ethyl-2,4,4-trimethyl-1,2,3,4-tetrahydroisoquinolin-7-yl)-3-chloro-4-methoxybenzamide;

N-(8-Ethyl-2,4,4-trimethyl-1,2,3,4-tetrahydroisoquinolin-7-yl)-3-chloro-4-ethoxybenzamide;

N-(8-Ethyl-2,4,4-trimethyl-1,2,3,4-tetrahydroisoquinolin-7-yl)-3-bromo-4-ethylbenzamide;

N-(8-Methyl-2,4,4-trimethyl-1,2,3,4-tetrahydroisoquinolin-7-yl)-3-bromo-4-ethoxybenzamide;

N-(8-Methyl-2,4,4-trimethyl-1,2,3,4-tetrahydroisoquinolin-7-yl)-4-methoxy-3-trifluoromethylbenzamide;

N-(8-Methyl-2,4,4-trimethyl-1,2,3,4-tetrahydroisoquinolin-7-yl)-3-chloro-4-ethoxybenzamide;

N-(8-Methyl-2,4,4-trimethyl-1,2,3,4-tetrahydroisoquinolin-7-yl)-3-cyano-4-ethylbenzamide;

N-(8-Bromo-2,4,4-trimethyl-1,2,3,4-tetrahydroisoquinolin-7-yl)-3-bromo-4-methoxybenzamide;

N-(8-Bromo-2,4,4-trimethyl-1,2,3,4-tetrahydroisoquinolin-7-yl)-4-methoxy-3-trifluoromethylbenzamide;

N-(8-Bromo-4,4-dimethyl-1,2,3,4-tetrahydroisoquinolin-7-yl)-4-methoxy-3-trifluoromethylbenzamide;

N-(4,4,8-Trimethyl-1,2,3,4-tetrahydroisoquinolin-7-yl)-4-methoxy-3-trifluoromethylbenzamide;

N-(4,4,8-Trimethyl-1,2,3,4-tetrahydroisoquinolin-7-yl)-3-bromo-4-ethoxybenzamide;

N-(4,4-Dimethyl-8-ethyl-1,2,3,4-tetrahydroisoquinolin-7-yl)-4-methoxy-3-trifluoromethylbenzamide;

N-(4,4-Dimethyl-8-ethyl-1,2,3,4-tetrahydroisoquinolin-7-yl)-3-bromo-4-ethoxybenzamide;

N-(4,4-Dimethyl-8-ethyl-1,2,3,4-tetrahydroisoquinolin-7-yl)-3-chloro-4-ethoxybenzamide;

N-(8-Cyano-2,4,4-trimethyl-1,2,3,4-tetrahydroisoquinolin-7-yl)-4-methoxy-3-trifluoromethylbenzamide;

N-(4,4,8-Trimethyl-1,2,3,4-tetrahydroisoquinolin-7-yl)-3-acetyl-4-ethoxybenzamide;

N-(4,4-Dimethyl-8-ethyl-1,2,3,4-tetrahydroisoquinolin-7-yl)-3-acetyl-4-ethoxybenzamide;

N-(4,4-Dimethyl-8-ethyl-1,2,3,4-tetrahydroisoquinolin-7-yl)-3-acetyl-4-methoxybenzamide;

N-(4,4-Dimethyl-8-ethyl-1,2,3,4-tetrahydroisoquinolin-7-yl)-4-methoxy-3-propionyl benzamide;

N-(8-Chloro-4,4-dimethyl-1,2,3,4-tetrahydroisoquinolin-7-yl)-4-methoxy-3-trifluoromethylbenzamide;

N-(8-Bromo-2,3,3-trimethyl-1,2,3,4-tetrahydroisoquinolin-7-yl)-4-methoxy-3-trifluoromethyl benzamide;

N-(8-Chloro-2,3,3-trimethyl-1,2,3,4-tetrahydroisoquinolin-7-yl)-3-chloro-4-ethoxy benzamide;

N-(8-Chloro-2,3,3-trimethyl-1,2,3,4-tetrahydroisoquinolin-7-yl)-3-chloro-4-methoxy benzamide;

N-(8-Chloro-2,3,3-trimethyl-1,2,3,4-tetrahydroisoquinolin-7-yl)-3-fluoro-4-methoxy benzamide;

N-(8-Chloro-3,3-dimethyl-1,2,3,4-tetrahydroisoquinolin-7-yl)-4-methoxy-3-trifluoromethyl benzamide;

N-(5-Iodo-1,1,2-trimethyl-1,2,3,4-tetrahydroisoquinolin-7-yl)-4-methoxy-3-trifluoromethyl benzamide;

N-(5-Cyano-1,1,2-trimethyl-1,2,3,4-tetrahydroisoquinolin-7-yl)-4-methoxy-3-trifluoromethyl benzamide;

N-(8-Bromo-3,3-dimethyl-1,2,3,4-tetrahydroisoquinolin-7-yl)-4-methoxy-3-trifluoromethylbenzamide;

N-(1,1,2,5-Tetramethyl-1,2,3,4-tetrahydroisoquinolin-7-yl)-3-bromo-4-ethoxybenzamide; and;

N-(6-Bromo-2,4,4-trimethyl-1,2,3,4-tetrahydroisoquinolin-7-yl)-3-bromo-4-ethoxybenzamide.

* * * * *